(12) United States Patent
Zhu

(10) Patent No.: US 9,482,616 B2
(45) Date of Patent: Nov. 1, 2016

(54) METHODS, KITS AND SYSTEMS FOR SIGNAL AMPLIFICATION FOR BIOASSAYS USING ZINC NANOPARTICLES

(71) Applicant: Xiaoshan Zhu, Reno, NV (US)

(72) Inventor: Xiaoshan Zhu, Reno, NV (US)

(73) Assignee: Board of Regents of the Nevada System of Higher Education, on behalf the University of Nevada, Reno, Reno, NV (US)

( * ) Notice: Subject to any disclaimer, the term of this patent is extended or adjusted under 35 U.S.C. 154(b) by 194 days.

(21) Appl. No.: 13/911,683

(22) Filed: Jun. 6, 2013

(65) Prior Publication Data

US 2013/0330743 A1 Dec. 12, 2013

Related U.S. Application Data

(60) Provisional application No. 61/656,369, filed on Jun. 6, 2012, provisional application No. 61/656,392, filed on Jun. 6, 2012, provisional application No. 61/656,410, filed on Jun. 6, 2012.

(51) Int. Cl.
*G01N 21/64* (2006.01)
*G01N 33/543* (2006.01)
(Continued)

(52) U.S. Cl.
CPC .... *G01N 21/6486* (2013.01); *G01N 33/54346* (2013.01); *G01N 33/582* (2013.01);
(Continued)

(58) Field of Classification Search
CPC .............. G01N 21/6486; G01N 33/54346; G01N 33/582; G01N 33/587; G01N 33/6887; G01N 33/6893; G01N 2800/324

USPC ............ 435/7.72, 8.5; 436/518, 525
See application file for complete search history.

(56) References Cited

U.S. PATENT DOCUMENTS

| 5,766,963 | A | * | 6/1998 | Baldwin et al. ............... 506/15 |
| 2003/0148544 | A1 | * | 8/2003 | Nie ..................... B82Y 15/00 |
| | | | | 436/524 |
| 2009/0181364 | A1 | * | 7/2009 | Gee .................................... 435/5 |

FOREIGN PATENT DOCUMENTS

CN 101672845 A * 3/2010

OTHER PUBLICATIONS

Kumar et al. "Amberlite XAD-2 functionalized with o-aminophenol synthesis and applications as extractant for copper(II), cobalt(II), cadmium(II), nickel(II), zinc(II), and lead(II)"; Talanta 51 (2000), 1187-1196.*

(Continued)

*Primary Examiner* — Mark Shibuya
*Assistant Examiner* — Pensee Do
(74) *Attorney, Agent, or Firm* — Klarquist Sparkman, LLP

(57) ABSTRACT

Disclosed herein are methods, kits and systems for signal amplification that can be used for many analytes. For example, a method of detecting an analyte in a sample includes contacting the sample containing the analyte with a detecting agent, wherein the detecting agent contains a specific binding agent that binds the analyte and zinc nanoparticles wherein the zinc nanoparticles and specific binding agent are coupled together; exposing the analyte bound to the specific binding agent which is coupled to the zinc nanoparticles to an acidic condition to release zinc ions from the zinc nanoparticles; contacting the released zinc ions with an indicator to generate a signal; and detecting the signal. The disclosed bioassay can be used in clinical and non-clinical settings. For example, the method can be used for clinical diagnosis, prognosis, and/or treatment-effectiveness or for testing for the presence of a substance like biological or chemical agents.

14 Claims, 27 Drawing Sheets

(51) Int. Cl.
G01N 33/58 (2006.01)
G01N 33/68 (2006.01)
(52) U.S. Cl.
CPC ........ *G01N33/587* (2013.01); *G01N 33/6887* (2013.01); *G01N 33/6893* (2013.01); *G01N 2800/324* (2013.01)

(56) References Cited

OTHER PUBLICATIONS

Aboulaich, A., et al., *Water-Based Route to Colloidal Mn-Doped ZnSe and Core/Shell ZnSe/ZnS Quantum Dots*, Inorg. Chem., 2010, 49:10940-01948.
Ai, J., et al., *Circulating MicroRNA-1 as a Potential Novel Biomarker for Acute Myocardial Infarction*, 2010, Biochem & BioPhys. Res. Comm., 391:73-77.
Boland, L., et al., *Occurrence of Unrecognized Myocardial Infarction in Subjects Aged 45 to 65 Years (The ARIC Study)*, Am. J. Cardiol., 2002, 90:927-931.
Braasch, D., et al., *Locked Nucleic Acid (LNA):Fine-Tuning the Recognition of DNA and RNA*, Chemistry & Biology, 2001, 8:1-7.
Bruchez, M., et al., *Semiconductor Nanocrystals as Fluorescent Biological Labels*, Science, 1998, 281:2013-2016.
Catuogno, S., et al., *Recent Advance in Biosensors for MicroRNAs Detection in Cancer*, Cancers, 2011, 3:1877-1898.
Chan, W., et al., *Luminescent Quantum Dots for Multiplexed Biological Detection and Imaging*, 2002, Curr. Opin. Biotech., 13:40-46.
Chim, St., et al., *Detection and Characterization of Placental MicroRNAs in Maternal Plasma*, 2008, Clinical Chem., 54(3):482-490.
Chittofrati, A., et al., *Uniform Particles of Zinc Oxide of Different Morphologies*, 1990, Colloids and Surfaces, 48:65-78.
Cissell, K., et al., *Bioluminescence-Based Detection of MicroRNA, miR21 in Breast Cancer Cells*, 2008, Anal. Chem., 80:2319-2325.
Cissell, K., et al., *Trends in MicroRNA Detection*, 2009, Anal. Bioanal. Chem., 394:1109-1116.
Clarke, N.J., et al., *MicroRNAs: Biology, Function, and Expression*, 2007, 1st Ed., DNA Press, Eagleville, PA.
Cottingham, K., *Quantum Dots Leave the Light On*, 2005, Anal. Chem., 77(17):354A-357A.
Cowles, C., et al., *Signal Amplification of Immunoassay Based on Fluorescence Measurement of Non-Fluorescent Zinc-Sulfide Nanoparticles*, Mar. 2011, poster presented at Pittcon2011, Atlanta, GA.
Cowles, C., et al., *Fluorescence Signal Transduction Mechanism for Immunoassay Based on Zinc Ion Release from ZnS Nanocrystals*, 2011, Analyst, 136:2975-2980.
Cowles, C., et al., *Sensitive Detection of C-Reactive Protein Using Zinc Sulfide Nanoparticles as Novel Fluorescence Signal Transducers*, Mar. 2012, poster presented at Pittcon2012, Orlando, FL.
Cowles, C., et al., *Facile Synthesis and Biological Application of Thioglycolic Acid Modified ZnO Nanoparticles*, Mar. 2012, slides from oral presentation made at Pittcon2012, Orlando, FL.
Cowles, C., et al., *Facile Synthesis and Biosensing Application of Hybrid Zinc Nanoparticles*, 2012, J. Nanosci. and Nanotech., 12:1-7.
Cowles, C., et al., *Dual Signal Amplification for Bioassays Using Ion Release of Nanolabels and Ion-Activated Enzyme Kinetics*, 2012, Analyst, 137:4815-4821.
Cowles, C., *Signal Amplification of Bioassay Using Zinc Nanomaterials*, dissertation submitted Aug. 2012, University of Nevada, Reno.
Cowles, C., et al., *MicroRNA Detection Using Magnetic Separation and Zinc-Based Nanolabels as Signal Transducers*, 2013, Anal. Methods, 5:801-804.
Das, P., et al., *Studies on Cadmium Toxicity in Plants: A Review*, 1997, Environ. Pollution, 98(1):29-36.
Devinney, M., et al., *Simultaneous Detection of Intracellular Free Calcium and Zinc Using Fura-2FF and FluoZin-3*, 2005, Cell Calcium, 37:225-232.
Du, D., et al., *Sensitive Immunosensor for Cancer Biomarker Based on Dual Signal Amplification Strategy of Graphene Sheets and Multienzyme Functionalized Carbon Nanospheres*, 2010, Anal. Chem., 82:2989-2995.
Du, E., et al., *Functionalized Graphene Oxide as a Nanocarrier in a Multienzyme Labeling Amplification Strategy for Ultrasensitive Electrochemical Immunoassay of Phosphorylated p53 (S392)*, 2011, Anal. Chem., 83: 746-752.
Edwards, K., et al., *Analysis of Liposomes*, 2006, Talanta, 68:1432-1441.
Edwards, K., et al., *Fluorescently labeled Liposomes for monitoring Cholera Toxin Binding to Epithelial Cells*, 2008, Anal. Biochem., 380:59-67.
Fang, Z., et al., *Facile Synthesis of Highly Luminescent UV-Blue-Emitting ZnSe/ZnS Core/Shell Nanocrystals in Aqueous Media*, 2009, J. Phys. Chem. C, 113:14145-14150.
Feigl, C., et al., *Safe, Stable and Effective Nanotechnology: Phase Mapping of ZnS Nanoparticles*, 2010, J. Mater. Chem., 20:4971-4980.
Fierke, C., et al., *Fluorescense-Based Biosensing of Zinc Using Carbonic Anhydrase*, 2001, BioMetals 14:205-222.
Fu, Y., et al., *Stable Aqueous Dispersion of ZnO Quantum Dots and Strong Blue Emission via Simple Solution Route*, 2007, J. Am. Chem. Soc., 129:16029-16033.
Gao, M., et al., *Strongly Photoluminescent CdTe Nanocrystals by Proper Surface Modification*, 1998, J. Phys. Chem. B, 102:8360-8363.
Gaponik, N., et al., *Thiol-Capping of CdTe Nanocrystals: An Alternative to Organometallic Synthetic Routes*, 2002, J. Phys. Chem. B, 106:7177-7185.
Gee, K., et al., *Detection and Imaging of Zinc Secretion from Pancreatic β-Cells Using a New Fluorescent Zinc Indicator*, 2002, J. Am. Chem. Soc., 124(5):776-778.
Gilad, S., et al., *Serum MicroRNAs are Promising Novel Biomarkers*, 2008) PLoS ONE 3(9):e3148.
Guo, S., et al., *Biomolucule-Nanoparticle Hybrids for Electrochemical Biosensors*, 2009, Trends in Anal. Chem., 28(1):96-109.
Guo, L., et al., *Highly Monodisperse Polymer-Capped ZnO Nanoparticles: Preparation and Optical Properties*, 2000, Appl. Phys. Lett.,76(20):2901-2903.
Hansen, J., et al., *Quantum-Don/Aptamer-Based Ultrasensitive Multi-Analyte Electrochemical Biosensor*, 2006, J. Am. Chem. Soc., 128:2228-2229.
Heidenreich, P., et al., *Forecasting the Future of Cardiovascular Disease in the United States*, 2011, Circulation, 123:933-944.
Hong, B, et al., *Biocompatible, nanogold-Particle Fluorescence Enhancer for Fluorophore Mediated, Optical Immunosensor*, 2006, Biosensors and Bioelectronics, 21:1333-1338.
Horie, M., et al., *Fluorometric Immunoassay Based on pH-Sensitive Dye-Encapsulating Liposomes and Gramicidin Channels*, 2007, Anal. Biochem., 369:192-201.
Hunt, J., et al., *A Rapid and Convenient Preparation of Apocarbonic Anhydrase*, Anal. Biochem., 1977, 79:614-617.
Jamieson, T., et al., *Biological Applications of Quantum Dots*, 2007, Biomaterials, 28:4717-4732.
Jana, N., et al., *Synthesis of Water-Soluble and Functionalized Nanoparticles by Silica Coating*, 2007, Chem. Mater., 19:5074-5082.
Kosaka, N., et al., *Circulating MicroRNA in Body Fluid: A New Potential Biomarker for Cancer Diagnosis and Prognosis*, 2010, Cancer Sci., 101(10):2087-2092.
Koshiol, J., et al., 2010, *Strengths and Limitations of Laboratory Procedures for MicroRNA Detection*, Cancer Epidemiol Biomarkers Prev., 19(4):907-911.
Kucur, E., et al., *Quantitative Analysis of Cadmium Selenide Nanocrystal Concentration by Comparative Techniques*, 2007, Anal. Chem., 79:8987-8993.
Lai, G., et al., *Dual Signal Amplification of Glucose Oxidase-Functionalized Nanocomposites as a Trace Label for Ultrasensitive*

(56) References Cited

OTHER PUBLICATIONS

*Simultaneous Multiplexed Electrochemical Detection of Tumor Markers*, 2009, Anal. Chem., 81:9730-9736.

LaVecchia, L., et al., *Cardiac Troponin I as Diagnostic and Prognostic Marker in Severe Heart Failure*, 2000, J. Heart Lung Transplant, 19(7):644-652.

Lewis, B., et al., *Conserved Seed Pairing, Often Flanked by Adenosines, Indicates that Thousands of Human Genes are MicroRNA Targets*, 2005, Cell, 120:15-20.

Li, H., et al., *Non-heavy-Metal NzS Quantum Dots with Bright Blue Photoluminescence by a One-Step Aqueous Synthesis*, 2007, Nanotechnology 18:205604.

Li, J., et al., *Detection of MicroRNA by Fluorescence Amplification Based on Cation-Exchange in Nanocrystals*, 2009, Anal. Chem., 81:9723-9729.

Li, J., et al., *Fluorescence Signal Amplification by Cation Exchange Ionic Nanocrystals*, 2009, Angew. Chem., 121:1616-1619.

Li, C., et al., *Circulating MicroRNAs as Novel and Sensitive Biomarkers of Acute Myocardial Infarction*, Clinical Biochem., 2012, 45:727-732.

Lin, H., et al., *MicroRNAs: Small RNAs with a Big Role in Gene Regulation*, 2004, Nature, 5:522-531.

Liu, G., et al., *Electrochemical Coding for Multiplexed Immunoassays of Proteins*, 2004, Anal. Chem., 76:7126-7130.

Liu, G., et al., *Nanomaterial Labels in Electrochemical Immunosensors and Immunoassays*, 2007, Talanta, 74:307-317.

Lu, L., et al., *Nanophotonic Crescent Mood Structures with Sharp Edge for Ultrasensitive Biomolecular Detection by Local Electromagnetic Field Enhancement Effect*, 2005, Nano Letters, 5(1):119-124.

Lynam, C., et al., *Carbon Nanotube-Based Transducers for Immunoassays*, 2009, Carbon, 47:2337-2343.

Malhotra, R., et al., *Ultrasensitive Electrochemical Immunosensor for Oral Cancer Biomarker IL-6 Using Carbon Nanotube Forest Electrodes and Multilable Amlification*, 2010, Anal. Chem., 82:3118-3123.

Mao, X., et al., *A Nanoparticle Amplification Based Quartz Crystal Microbalance DNA Sensor for Detection of Escherichia coli O157*:H7, 2006, Biosensors and Bioelectronics, 21:1178-1185.

McDonald, J., et al., *Analysis of Circulating MicroRNA: Preanalytical and Analytical Challenges*, 2011, Clinical Chem., 57(6):833-840.

Medintz, I., et al., *Quantum Dot Bioconjugates for Imaging, Labelling and Sensing*, 2005, Nature Matrials, 4:435-446.

Moussodia, R., et al., *Biocompatible and Stable ZnO Quantum Dots Generated by Functionalization with Siloxane-Core PAMAM Dendrons*, 2010, J. Mater. Chem., 20:1147-1155.

Murphy, C., *Optical Sensing with Quantum Dots*, 2002, Anal. Chem, 74(19):520A-526A.

Pathak, S., et al., *Hydroxylated Quantum Dots as Luminescent Probes for in Situ Hybridization*, 2001, J. Am. Chem. Soc., 123:4103-4104.

Planell-Saguer, M., et al., *Analytical Aspects of MicroRNA in Diagnostics: A Review*, 2011, Analytica Chimica Acta, 699:134-152.

Pohlmann, C., et al., *Electrochemical Detection of MicroRNAs via Gap Hybridization Assay*, 2010, Anal. Chem., 82:4434-4440.

Qavi, A., et al., *Sizing Up the Future of MicroRNA Analysis*, 2010, Anal. Bioanal. Chem., 398:2534-2549.

Qavi, A., et al., *Anti-DNA: RNA Antibodies and Silicon Photonic Microring Resonators: Increased Sensitivity for Multiplexed MicroRNA Detection*, 2011, Anal. Chem., 83:5949-5956.

Rogach, A., et al., *Aqueous Synthesis of Thiol-Capped CdTe Nanocrystals: State-of-the-Art*, 2007, J. Phys. Chem. C, 111:14628:14637.

Rosi, N., et al., *Nanostructures in Biodiagnostics*, 2005, Chem. Rev., 105:1547-1562.

Sapsford, K., et al., *Biosensing with Luminescent Semiconductor Quantum Dots*, 2006, Sensors, 6:925-953.

Sentandreu, M., et al., *A Rapid, Simple and Sensitive Fluorescence Method for the Assay of Angiotensin-I Converting Enzyme*, 2006, Food Chem., 97:546-554.

Senthilkumar, K., et al., *Preparation of ZnO Nanoparticles for Bio-Imaging Applications*, 2009, Phys. Status Solidi B, 246(4):885-888.

Sipova, H., et al., *Surface Plasmon Resonance Biosensor for Rapid Label-Free Detection of Microribonucleic Acid at Subfemtomole Level*, 2010, Anal. Chem., 82:10110-10115.

Song, S., et al., *A Fluoro-Microbead Guiding Chip for Simple and Quantifiable Immunoassay of Cardiac Troponin I (cTnI)*, 2011, Biosensors and Bioelectronics, 26:3818-3824.

Sperling, R., et al., *Surface Modification, Functionalization and Bioconjugation of Colloidal Inorganic Nanoparticles*, 2010, Phil. Trans. R. Soc. A, 368:1333-1383.

Tang, X., et al., *Synthesis of ZnO Nanoparticles with Tunable Emission Colors and Their Cell Labeling Applications*, 2010, Chem. Mater., 22:3383-3388.

Tatsu, Y., et al., *Peroxidase-Dependent Fluorescence Decrease of Carboxyfluorescein and its Enhancement by Liposome Encapsulation*, 1995, Fresenius J. Anal. Chem., 351:782-785.

Tenu, J., et al., *Kinetic Study of the Activiation Process of β-Galactosidase from Escherichia coli by Mg2+*, 1972, Eur. J. Biochem. 26:112-118.

Thaxton, C., et al., *Nanoparticle-Based Bio-Barcode Assay Redefines "Undetectable" PSA and Biochemical Recurrence After Radical Prostatectomy*, 2009, P. Natl. Acad. Sci., 106(44):18437-18442.

Van Emom, *Immunoassay and Other Bioanalytical Techniques*, Dec. 2006, CRC Press. ISBN 9780849339424.

van Rooij, E., *The Art of MicroRNA Research*, 2011, Circ. Res., 108:219-234.

Wang, J., et al., *Ultrasensitive Electrical Biosensing of Proteins and DNA: Carbon-Nanotube Derived Amplification of the Recognition and Transduction Events*, 2004, J. Am. Chem. Soc., 126:3010-3011.

Wang, J., *Nanomaterial-Based Electrochemical Biosensors*, 2005, Analyst, 130:421-426.

Wang, L., et al., *Locked Nucleic Acid Molecular Beacons*, 2005, J. Am. Chem. Soc., 127:15664-15665.

Wang, J., *Nanomaterial-Based Amplified Transduction of Biomolecular Interactions*, 2005, Small, 1(11):1036-1043.

Wang, J., et al., *Sensitive Immunoassay of a Biomarker Tumor Necrosis Factor-α Based on Poly(guanine)-Functionalized Silica Nanoparticle Label*, 2006, Anal. Chem., 78-6974-6979.

Wang, J., et al., *Sensitive Electrochemical Immunoassay for 2, 4, 6-Trinitrotoluene Based on Functionalized Silica Nanoparticle Labels*, 2008, Analytica Chimica Acta, 610:112-118.

Wang, J., et al., *Magnetic Nanoparticle Enhanced Surface Plasmon Resonance Sensing and Its Application for the Ultrasensitive Detection of Magnetic Nanoparticle-Enriched Small Molecules*, 2010, Anal. Chem., 82:6782-6789.

Wark, Al., et al., *Multiplexed Detection Methods for Profiling MicroRNA Expression in Biological Samples*, 2008, Angew. Chem. Int. Ed., 47:644-652.

Wei, J., et al., *A Novel Sandwich Immunosensing Method for Measuring Cardiac Troponin I in Sera*, 2003, Anal. Biochem., 321:209-216.

Zampetaki, A., et al., *Plasma MicroRNA Profiling Reveals Loss of Endothelial MiR-126 and Other MicroRNAs in Type 2 Diabetes*, 2010, Circ. Res., 107:810-817.

Zhang, J., et al., *Oriented Attachment Kinetics for Ligand Capped Nanocrystals: Coarsening of Thiol-PbS Nanoparticles*, 2007, J. Phys. Chem. B, 111:1449-1454.

Zhang, T., et al., *A General Approach for Transfirring Hydrophobic Nanocrystals into Water*, 2007, Nano Letters, 7(10):3203-3207.

Zhang, S., et al., *A Novel Immunoassay Strategy Based on Combination of Chitosan and a Gold Nanoparticle Label*, 2007, Talanta, 71:1530-1535.

Zhang, Y., et al., *Synthesis and Photoluminescence Properties of Hydrophilic ZnS Nanoparticles*, 2010, Mater. Letters, 64:1521-1523.

(56) References Cited

OTHER PUBLICATIONS

Zhong, W., *Nanomaterials in Fluorescence-Based Biosensing*, 2009, Anal. Bioanal. Chem., 394:47-59.

Zhou, J., et al., *Dissolving Behavior and Stability of ZnO Wires in Biofluids: A Study on Biodegradability and Biocompatibility of ZnO Nanostructures*, 2006, Adv. Mater., 18:2432-2435.

Zhu, Y., et al., *Amplification Strategy Based on Gold Nanoparticle-Decorated Carbon Nanotubes for Neomycin Immunosensors*, 2010, Biosensors and Bioelectronics, 26:1002-1008.

Zhu, X, *Dual Signal Amplification for Bioassays Using Ion Release of Nanolabels and Ion-Activated Enzyme Kinetics*, Mar. 2013, slides used in oral presentation made at Pittcon2013, Pittsburgh, PA.

\* cited by examiner

Me⁺ — Released metal ions

METHODS, KITS AND SYSTEMS FOR SIGNAL AMPLIFICATION FOR BIOASSAYS USING ZINC NANOPARTICLES

CROSS REFERENCE TO RELATED APPLICATION

This application claims the benefit of U.S. Provisional Patent Application No. 61/656,369, filed Jun. 6, 2012, U.S. Provisional Patent Application No. 61/656,392, filed Jun. 6, 2012, and U.S. Provisional Patent Application No. 61/656,410, filed Jun. 6, 2012, all of which are incorporated herein by reference in their entirety.

FIELD

This disclosure is related to bioassays and in particular, to reagents for immunoassays.

BACKGROUND

Nanotechnology based signal amplification for biosensing has been investigated over the last decade. Several categories of nanomaterials such as gold nanoparticles, magnetic oxide nanoparticles, carbon nanostructures, and semiconductor nanoparticles have seen a multitude of applications in this aspect due to their unique physical or chemical properties. For instance, gold nanoparticles have been used as substrates for surface enhanced Raman scattering (SERS) or fluorescence due to the intensified local electromagnetic fields on their surfaces. Magnetic oxide nanoparticles have been employed as signal enhancers or amplifiers in surface Plasmon resonance (SPR) or quartz crystal microbalance (QCM) biosensors due to their high refractive index and molecular weight. Carbon nanotubes and graphene oxide have been adopted as biolabels to carry more enzymes for signal amplification due to their long length or large surface area. Semiconductor nanoparticles (quantum dots) have brighter fluorescence than conventional organic fluorophores and thus have replaced organic fluorophores in various bioassays. In addition, because semiconductor nanoparticles are chemically composed of heavy metal ions such as $Cd^{2+}$, they also can release hundreds of thousands of heavy metal ions (this metal ion release is considered to be a signal amplification process). The released metal ions can be deposited on a mercury electrode for electrochemical detection, or they can bind with non-fluorescent, metal-ion sensitive dyes to generate fluorescence for signal measurement.

Most of the aforementioned approaches are single-stage signal amplification processes. Recently, several works have introduced dual signal amplification by coupling two single signal enhancement approaches in signal transduction of biosensing. Dual signal amplification is anticipated to be more efficient at improving bioassay sensitivity or lowering detection limits, because it has a higher signal gain. However, the reported dual signal amplification strategies mainly focus on applying carbon nanomaterials or gold nanoparticles. For example, some electrochemical bioassays applied carbon nanotube or graphene to not only increase sensing areas but also carry more labeling enzymes. Gold nanoparticle-based bio-barcode assays utilized gold nanoparticles to load more barcode DNA labels and additionally to catalyze silver enhancement for the detection of biomolecules.

Many of the presently available amplification processes whether signal—stage or dual-stage are inadequate. For example, many are labor intensive, have insufficient sensitivity, or utilize reagents that can be harmful to the environment. Therefore, more sensitive, cost-efficient, less toxic bioassays are needed.

SUMMARY

Disclosed herein is a zinc-nanoparticle based signal amplification methods that can be used for many analytes including, but not limited to, cells, proteins and microRNAs. It is desirable that analytical measurements have high sensitivity or lower detection limits for the analytes of interest. The disclosed signal amplification methods using Zn-nanoparticles are shown herein to have high sensitivity or lower detection limits compared to the conventional enzyme-linked immunosorbent assay (ELISA) technology. In particular, ELISA technology utilizes biological enzymes as labels for single stage signal amplification. The biological enzymes fabricated using biological methods are often expensive and need to be immobilized on antibody for assaying. The immobilization is tedious and also causes the reaction activity loss of enzymes. In addition, the biological enzymes have a limited on-shelf time. In contrast, the presently disclosed amplification methods utilize Zn-nanoparticles as labels. As shown herein, Zn-nanoparticles are easily made by one of ordinary skill in the art and not associated with any significant cost. Further, although enzymes are used in the disclosed dual amplification method, enzyme immobilization is not needed. Moreover, the enzyme (carbonic anhydrase) is inexpensive and deactivated and thus, can be stored for long periods of time. Thus, the disclosed methods, systems and kits possess a high detection resolution, and offer the advantage of straightforward operation with simple preparation of nanoparticles and does not require enzyme immobilization.

In some embodiments, a method of detecting an analyte in a sample is disclosed. In one example, the method includes contacting the sample containing the analyte with a detecting agent, wherein the detecting agent contains a specific binding agent that binds the analyte and zinc nanoparticles wherein the zinc nanoparticles and specific binding agent are coupled together; exposing the analyte bound to the specific binding agent which is coupled to the zinc nanoparticles to an acidic condition to release zinc ions from the zinc nanoparticles; contacting the released zinc ions with an indicator to generate a signal; and detecting the signal.

In some embodiments, the method further comprises contacting the released zinc ions with a basic solution to adjust the pH in the range of 5.5 to 7.0 prior to contacting the released zinc ions with an indicator to generate a signal.

In some embodiments, the zinc nanoparticles are zinc sulfide nanoparticles or zinc oxide nanoparticles.

In some embodiments, the zinc nanoparticles are conjugated to one of avidin, streptavidin, or neutravidin.

In some embodiments, the zinc nanoparticles are zinc sulfide nanoparticles and are conjugated to neutravidin.

In some embodiments, the method further comprises synthesizing the zinc nanoparticles.

In some embodiments, zinc sulfide nanocrystals are synthesized with thioacetamide as the sulfide source and zinc nitrate as the zinc source, and thioglycolic acid (TGA) as the matrix for a resultant carboxylated coating on the nanocrystal surface through the binding between a thiol group of TGA and zinc atoms on the nanocrystal surface.

In some embodiments, the zinc nanocrystals are synthesized by combining zinc nitrate and ethanolamine in an aqueous solution with thioglycolic acid (TGA), to form hybrid zinc nanoparticles (Zn—O—S—C nanoparticles) composed of zinc, oxygen, sulfur and carbon.

In some embodiments, the signal is a fluorescent signal.

In some embodiments, the method further comprises capturing the analyte from the sample prior to contacting the analyte with a detecting agent by contacting the sample containing the analyte with a capture molecule specific for the analyte.

In some embodiments, the capture molecule is conjugated to a substrate.

In some embodiments, the specific binding agent is a detection antibody capable of binding to the analyte.

In some embodiments, the detection antibody is tagged with biotin.

In some embodiments, contacting the released metal ions with an indicator to generate a signal comprises contacting the release metal ions with an apo-enzyme and a substrate to generate the signal.

In some embodiments, the apo-enzyme is apo-carbonic anhydrase and the substrate is fluorescein diacetate (FDA).

The disclosed bioassays can be used in clinical and non-clinical settings. For example, the methods can be used for clinical diagnosis, prognosis, and/or treatment-effectiveness or for testing for the presence of a substance like biological or chemical agents. Also disclosed herein are methods of diagnosing a condition utilizing the disclosed methods of detecting an analyte or a resulting bioassay thereof.

In some embodiments, the condition is myocardial infarction and the analyte is human cardiac troponin I.

In some embodiments, the analyte is microRNA.

The foregoing and other features and advantages of the disclosure will become more apparent from the following detailed description, which proceeds with reference to the accompanying figures.

SEQUENCE LISTING

Figure 1:
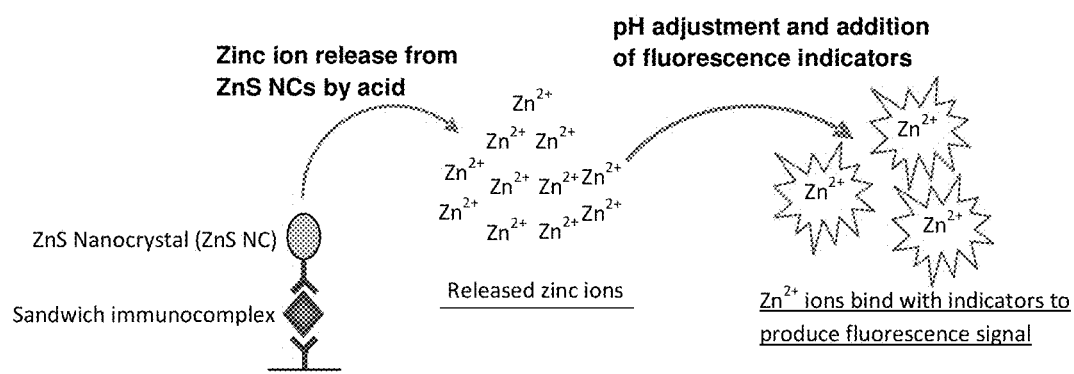
FIG. 1 is a schematic illustrating an exemplary signal transduction mechanism for an embodiment of a disclosed immunoassay.

The nucleic and amino acid sequences listed in the sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the nucleotide sequence of miRNA 2.
SEQ ID NO: 2 is a nucleic acid sequence of a locked nucleic acid (LNA) probe complimentary to miRNA-21.

DETAILED DESCRIPTION

I. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a peptide" includes single or plural peptides and can be considered equivalent to the phrase "at least one peptide."

As used herein, the term "comprises" means "includes." Thus, "comprising a peptide" means "including a peptide" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand which include a light chain and/or heavy chain immunoglobulin variable region which specifically binds an epitope of an antigen. A specific binding agent binds substantially only to a defined target. It is recognized that a minor degree of non-specific interaction may occur between a molecule, such as an antibody, and a non-target polypeptide. Nevertheless, specific binding can be distinguished as mediated through specific recognition of the antigen. Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a target polypeptide as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that can be used to determine specific immunoreactivity.

Antibodies can be composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Biomarker: Molecular, biological or physical attributes that characterize a physiological state and can be objectively measured to detect or define disease progression or predict or quantify therapeutic responses. For instance, a substance used as an indicator of a biologic state. It is a characteristic that is objectively measured and evaluated as an indicator of normal biologic processes, pathogenic processes, or pharmacologic responses to a therapeutic intervention.

Cancer: A malignant disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melanoma). It is contemplated that the disclosed nanoparticles, methods and assays can be utilized to detect cancer.

Contacting: Placement in direct physical association, which can include both in solid and liquid form. Contacting can occur in vitro with for example with samples, such as biological samples, for example isolated cells or cell free extracts, such as cell lysates, or in vivo by administering to a subject.

Control: A reference standard. In some examples, a control can be a known value indicative of a particular activity. In other examples, a control is a sample not treated with a test agent. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Complex (complexed): Two proteins, or fragments or derivatives thereof, one protein (or fragment or derivative) and a non-protein compound, are said to form a complex when they measurably associate with each other in a specific manner. In some examples, a complex is the complex formed between target molecule and an antibody that specifically binds to the target molecule.

Detect: To determine if an agent (such as a signal, such as a fluorescent signal, or particular molecule) is present or absent. In some examples, this can further include quantification. In some examples, the disclosed assays are used to detect a biomarker of interest.

Diagnosis: The process of identifying a condition or disease by its signs, symptoms and results of various tests, for example tests for the expression of a particular biomarker. The conclusion reached through that process is also called "a diagnosis." Forms of testing commonly performed include blood tests, medical imaging, urinalysis, and biopsy.

For a period of time sufficient: A phrase used to describe a period of time in which a desired activity occurs. It is appreciated that the time period can be varied based on the concentration of the reagents used and other factors.

Human Cardiac Troponin I (Human cTnI): Human cTnI is a small protein (around 24 kDa) that is considered to be a biomarker for the diagnosis of myocardial infarction (MI). Annually, 785,000 Americans will suffer a new MI and 470,000 will experience a recurrent heart attack, while an additional 195,000 are estimated to undergo an unreported silent MI. Approximately 16% of individuals experiencing a first MI die acutely and of the 84% of patients that do survive their MI, an estimated 15 years of life is lost. cTnI is highly specific for cardiac muscle damage, and its concentration in blood increases dramatically from a normal level (below 1.0 ng/mL) after the onset of a myocardial infarction. In some works, the cut-off cTnI concentration for clinical diagnosis has been reported to be 1 ng/mL (or around 40 pM) in human serum.

Label: A detectable compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule antibody or nucleic acid it specifically binds.

Linker: A compound or moiety that acts as a molecular bridge to operably link two different molecules such as two peptides, repeated sequences of a peptides or even a peptide with another molecule (such as a molecule of a solid support, for example a bead or multiwell plate or a detectable label, such as the labels described herein), wherein one portion of the linker is operably linked to a first molecule, and wherein another portion of the linker is operably linked to a second molecule and generally the linker is heterologous to the first and second molecules. In some examples, a linker is a polypeptide, such as a polypeptide that is between about two amino acid residues and about ten amino acid residues in length. In the case of peptide linker connecting two peptides, the peptide linker can be transcribed from a single piece of nucleic acid that encodes the two peptides and the linker. In some embodiments, there is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers can include, but are not limited to, homobifunctional linkers and hetero-bifunctional linkers. Hetero-bifunctional linkers, well known to those skilled in the art, contain one end having a first reactive functionality to specifically link a first molecule, and an opposite end having a second reactive functionality to specifically link to a second molecule. Depending on such factors as the molecules to be linked, and the conditions in which the method of detection is performed, the linker can vary in length and composition for optimizing such properties as flexibility, stability, and resistance to certain chemical and/or temperature parameters. In particular examples, a linker is the combination of streptavidin, avidin or neutravidin and biotin.

MicroRNAs (miRNAs): Relatively short (a few nanometers in length with 17-25 nucleotides), post-transcriptional regulators that bind to target complimentary sequences of messenger RNA (mRNA). MiRNAs are gene regulators with conserved biological functions. Currently it is believed that over 1,000 miRNAs could be encoded by the human genome and target up to 60% of the entire genome. Altered miRNA expression levels have been implicated as indicators of different disease states such as cancer, cardiac disease, and diabetes. The disclosed zinc-based nanolabels can be used to detect microRNAs.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, for example a "recombinant polypeptide." A recombinant nucleic acid may serve a non-coding function (for example a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Operably linked: A molecule is "operably linked" to another molecule when the two molecules are connected by a linker, for example a linker connecting a peptide to another molecule, such as solid support or a detectable label.

Peptide, Polypeptide, and/or Protein: Any compound composed of amino acids, amino acid analogs, chemically bound together. Amino acids generally are chemically bound together via amide linkages (CONH). Additionally, amino acids may be bound together by other chemical bonds. For example, the amino acids may be bound by amine linkages. Peptides include oligomers of amino acids, amino acid analog, or small and large peptides, including polypeptides or proteins.

Prognosis: A prediction of the course of a condition or disease. The prediction can include determining the likelihood of a subject to develop the disease, to respond to a particular therapy or combinations thereof.

Sample: A sample, such as a biological sample, is a sample that includes biological materials (such as nucleic acid and proteins). In some examples, a biological sample is obtained from an organism or a part thereof, such as an animal. In particular embodiments, the biological sample is obtained from an animal subject, such as a human subject. A biological sample can be any solid or fluid sample obtained from, excreted by or secreted by any living organism, including without limitation multicellular organisms (such as animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A biological sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific binding agent: An agent that binds substantially only to a defined target, such as a protein, enzyme, polysaccharide, oligonucleotide, DNA, RNA, miRNA, recombinant vector or a small molecule. Thus, a nucleic acid-specific binding agent binds substantially only to the defined nucleic acid, such as RNA (e.g., miRNA), or to a specific region within the nucleic acid. A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Substrate: A molecule that is acted upon by an enzyme. A substrate binds with the enzyme's active site, and an enzyme-substrate complex is formed. In some examples, the enzyme catalyses the incorporation of an atom or other molecule into the substrate.

DETAILED DESCRIPTION

Disclosed herein are methods, kits and systems for signal amplification that can be used for many analytes. In one embodiment, a first messenger is used to amplify the detectability of an analyte, such as biomarker or molecule of interest. For example, a signal transduction mechanism, such as fluorescent signal, based on cation release from ZnS nanocrystals is disclosed for a bioassay, such as an immunoassay, including a sandwich immunoassay. In this mechanism, ZnS nanocrystals are dissolved by acid to release zinc ions. After pH adjustment of the dissolving solution using a basic solution, a zinc-ion sensitive fluorescence indicator, such as Fluozin-3, is added to bind with the released zinc ions for sensitive fluorescence measurement. A disclosed immunoassay demonstrates a low detection limit around 1 pM and a detection range with two orders of magnitude (1 pM to 0.5 nM).

In other embodiments, dual signal amplification techniques for bioassays are disclosed. Embodiments of the disclosure include the release of a metal ion, such as a zinc-ion, from a nanoparticle label such as ZnS and the activation of enzyme kinetics by the released metal ions as cofactors. In the ion release process, each nanoparticle label liberates a high number of metal ions such as by acidic dissolution. After the ion release, at appropriate pH levels, the released metal ions are used as cofactors to trigger the enzymatic activity of a desired enzyme, such as carbonic anhydrase. The fluorescence produced from the activated enzyme kinetics is measured for bioassay signal quantification.

In some examples, methods of preparing nanocrystals as labels in an immunoassay are provided. In some examples, the method includes synthesizing nanocrystals, such as synthesizing zinc nanocrystals, such as zinc chalcogen nanocrystals, such as ZnS or ZnO nanocrystals. It is contemplated that nanocrystals can be synthesized by techniques known to those of skill in the art including those described herein, such as in the Examples. In one example, ZnS nanocrystals are synthesized with thioacetamide as the sulfide source and zinc nitrate as the zinc source. TGA is used in the synthesis as the matrix for a resultant carboxylated coating on the nanocrystal surface through the binding between the thiol group of TGA and zinc atoms on the nanocrystal surface. Carboxylation of nanocrystals makes their surface hydrophilic in aqueous solution and therefore enhances the colloidal stability of nanocrystals. On the other hand, the carboxyl groups on the nanocrystal surface allow conjugation with other proteins, including NeutrAvidin, through the cross linking reaction with EDC and NHS.

In some examples, hybrid zinc nanoparticles are synthesized by adding thioglycolic acid (TGA) into a ZnO-particle synthesis procedure. For example, the zinc-based nanoparticles are synthesized by adding thioglycolic acid (TGA) into a mixture of zinc nitrate and ethanolamine in an aqueous solution. Here, the nanoparticles synthesized with the addition of TGA are called or defined as the hybrid zinc nanoparticles (or Zn—O—S—C nanoparticles) since they are composed of zinc, oxygen, sulfur and carbon.

In some examples, nanocrystals are spherical with a diameter of approximately 10 to 60 nM, such as 20 to 50 nM, including 10 nM, 15 nM, 20 nM, 25 nM, 30 nM, 35 nM, 40 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, and 60 nM are used in the preparation. In some examples, zinc nanocrystals are spherical with a diameter of approximately 10 to 60 nM, such as 20 to 50 nM, including 10 nM, 15 nM, 20 nM, 25 nM, 30 nM, 35 nM, 40 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, and 60 nM are used in the preparation.

In some embodiments, preparation of nanocrystals as labels in an immunoassay comprises the following: dissolving the nanocrystals, such as zinc nanocrystals, such as zinc chalcogen nanocrystals, such as zinc sulfide (ZnS) or zinc oxide (ZnO) nanocrystals, in acid to release the metal ion, such as zinc ions; exposing the released metal ions, such as zinc ions, to a basic solution to adjust the pH in the range of 5.3 to 7.2, such as between 5.5 and 7.0, between 5.5 and 6.5, 6.0 and 7.0, including 5.3, 5.4, 5.5, 5.6, 5.7, 5.8, 5.9, 6.0, 6.1, 6.2, 6.3, 6.4, 6.5, 6.6, 6.7, 6.8, 6.9, 7, 7.1 or 7.2; contacting the resulting metal ions, such as zinc ions, with a fluorescent indicator, such as a zinc fluorescent indicator (e.g., FluoZin-3), for sensitive fluorescence measurement in which the resulting immunoassay demonstrates a low detection limit around 1 pM and a detection range with two orders of magnitude (1 pM to 0.5 nM or 10 pM to 1 nM).

In some examples, zinc concentrations are measured using fluorescent indicators nominally designed for $Ca^{2+}$ detection such as fura-2 or more recently developed indicators with greater $Zn^{2+}$ selectivity, such as FluoZin indicators from Invitrogen, including FluoZin-1 (Life Technologies Catalog Nos. F24180 and F24181), FluoZin-2 (Life Technologies Catalog No. F24189) or FluoZin-3 (Life Technologies Catalog Nos. F24194 and F24195). In some particular examples, zinc concentrations are measured using FluoZin-3.

In some examples, the method further includes conjugating nanoparticles, such as synthesized nanoparticles, so that the resulting molecules can serve as biolabels or signal transducers in a bioassay, such as an immunoassay, including, but not limited to, a sandwich immunoassay. For example, the method includes conjugating the synthesized nanoparticles with a capture moiety, such as avidin, such as Neutravidin and applying the generated bioconjugated nanoparticles as biolabels in an immunoassay.

In alternative embodiments, other ions capable of release from nanocrystals could be used as the first messenger. In addition other signal sources, such as changes in color or different forms of fluorescence, could be used as well.

In some examples, a dual signal amplification approach for detecting a marker, such as a biomarker or other material in need of detection, is disclosed. For example, in some examples, the method includes capturing a marker, such as a biomarker, or molecule of interest, with a capture molecule, such as a capture antibody specific to the marker or molecule of interest. In some examples, the capture molecule, such as the capture antibody, is conjugated to a substrate, such as a bead, such as a para-magnetic bead, or a surface of a reaction well. In some examples, the method includes exposing or contacting a sample, such a biological sample, with the capture molecule to determine if the molecule of interest, such as a biomarker, is present or altered in sample. After capture, the capture molecule/marker conjugate is exposed to a detection agent. In some examples, the detection agent includes a specific binding agent for the molecule/marker of interest and nanoparticles, such as metal nanoparticles, such as those disclosed herein. In some examples, the capture molecule/marker conjugate is first exposed to a specific binding agent for the molecule/marker of interest, wherein the specific binding agent is an antibody, such as an antibody with a tag, such as biotin, to form an immunocomplex. In this embodiment, the method includes then exposing or contacting the immunocomplexes with nanoparticles, such as metal nanoparticles, including zinc nanoparticles disclosed herein, which are conjugated to a substance capable of binding the tag, such as avidin, streptavidin or neutravidin if the tag is biotin to form a nanoparticle-immunocomplex. In some examples, the method includes one or more washing steps. In some examples, the method includes exposing or contacting the nanoparticle-immunocomplexes to conditions that result in the release of metal ions from the metal nanoparticles and enzyme kinetics are triggered by the released metal ions. When the ions are released from the nanoparticle labels, such as by using an acidic solution, each nanoparticle releases hundreds of thousands of metal ions, such as zinc ions (the first stage of signal amplification). In some examples, the method includes exposing or contacting the released metal ions with a basic solution to adjust the pH. After pH adjustment and buffering, the method includes mixing the released metal ions, as cofactors, with an metallic enzyme, such as an apo-enzyme, such as carbonic anhydrase, and a substrate, such as fluorescein diacetate (FDA) to trigger an enzyme-substrate reaction (the second stage of signal amplification). The enzyme-substrate reaction generates a signal, such as a fluorescent signal or color change, for signal measurement.

In some specific examples, the disclosed nanoparticles, such as ZnS or ZnO nanoparticles are used as the labels, an apo-E enzyme, such as a metalloenzyme, including, but not limited to, carbonic anhydrase (CA), is used as the enzyme and fluorescein diacetate (FDA) is employed as the substrate in this technique.

The disclosed methods do not require immobilization of enzymes on any surfaces.

In some examples, the disclosed methods and assay can measure zinc nanocrystals, such ZnS nanocrystals below 10 pM, such as between 20 fM and 5 pM, between 25 fM to 0.25 pM, or between 100 fM to 1 pM. In some examples, the disclosed methods and assay has a detection range between 0.5 to 50 pM.

The antibodies used in any of the disclosed methods can be labeled. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes Handbook of Fluorescent Probes and Research Chemicals* (1992-1994). The metal compounds that can be conjugated to the antibodies include, but are not limited to, zinc nanocrystals, such as zinc chalcogen nanocrystals, such as ZnS or ZnO nanocrystals. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}Tc$), $^{125}I$ and amino acids including any radionucleotides, including but not limited to, $^{14}C$, $^{3}H$ and $^{35}S$.

The presence of a marker or molecule of interest can be determined with multiple specific binding agents, such as one, two, three, or more specific binding agents. Thus, the methods can utilize more than one antibody. In some embodiments, one of the antibodies is attached to a solid support, such as a multiwell plate (such as, a microtiter plate), bead, membrane or the like. In practice, microtiter plates may conveniently be utilized as the solid phase. The surfaces may be prepared in advance, stored, and shipped to another location(s). However, antibody reactions also can be conducted in a liquid phase.

Figure 27:
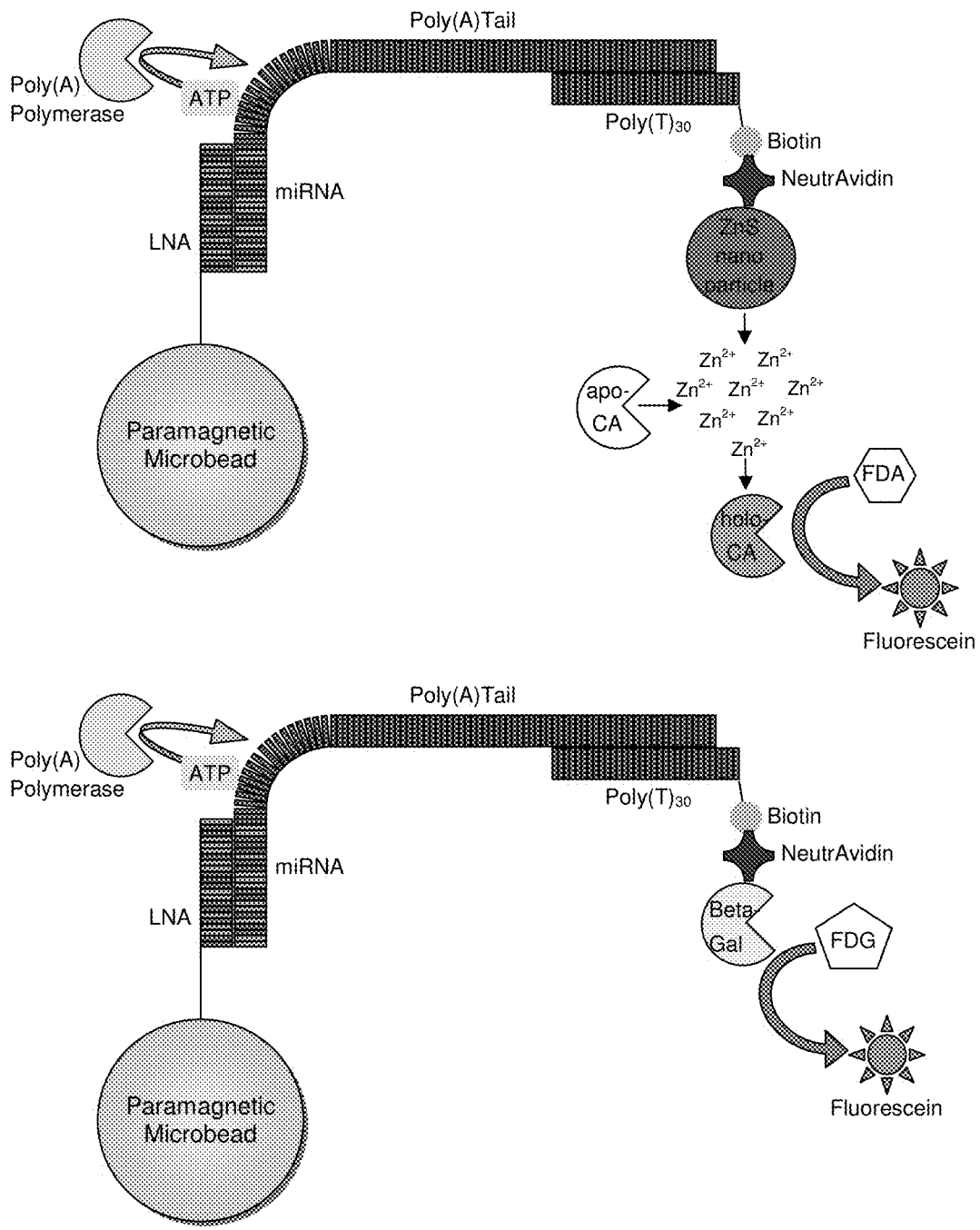
FIG. 27 is a schematic of the miRNA detection procedure: (1) magnetic microbeads as solid support carrying LNA probes to capture miRNA, (2) poly(A) polymerase reaction for polyadenylation, and (3) zinc-based nanolabels for signal transduction by releasing zinc ions to activate apo-carbonic anhydrase (top illustration) or beta-galactosidase for signal transduction (bottom illustration)

In additional embodiments, the disclosed nanoparticles are incorporated into a miRNA detection method, which combines magnetic separation, polyadenylation, and signal amplification. One particular embodiment is shown in FIG. 27 and described in detail in Example 4. In this procedure, locked nucleic acid (LNA) probes complimentary to miRNA-21 are conjugated to a paramagnetic bead and hybridization captures miRNA-21 in solution. After capture, poly(A) polymerase catalyzes a polyadenylation reaction on the 3'-OH end of the bound miRNA-21. The generation of poly(A) tails is followed by biotinylated poly(T)$_{30}$ hybridization with the poly(A) tail which specifically permits NeutrAvdin-conjugated ZnS nanoparticle labeling or streptavidin-conjugated beta-galactosidase labeling through biotin-Neutravidin chemistry. For signal transduction of the assay, two alternative approaches are the following: (1) zinc ions from the ZnS nanoparticles are released to bind with zinc-ion depleted carbonic anhydrase and activate the enzymatic kinetics of carbonic anhydrase which converts fluorescein diacetate to fluorescein, or (2) beta-galactosidase (enzyme) converts fluorescein-di-beta-D-galactopyranoside (FDG) to fluorescein.

Aspects of the disclosure are directed to diagnostic and non-diagnostic bioassays and may be embodied in a method or as a kit, system, or apparatus that practices the method. For example, the methods may be used to detect a biomarker, such as human cardiac troponin I (cTnI), from a subject, such as a biological sample, such as a serum, plasma, urine or other bodily fluids, for a clinical diagnosis of a condition, such as myocardial infarction. Embodiments of the disclosure are capable of distinguishing clinically critical levels of biomarkers indicative of a condition, such as cTnI. The diagnostic bioassay can be used to detect other conditions, such as cancers, infections, strokes, and other diseases or processes having detectable biomarkers, such that result from exposure to an exogenous agent like a drug or toxin. The bioassay can be used to detect miRNAs associated with a particular condition, such as a disease, likelihood to develop a particular disease or condition and/or severity of a particular disease or condition.

The bioassay can be used in non-clinical settings as well, such as testing for the presence of a substance like biological or chemical agents, such as in the food industry, including for food safety control.

Embodiments of the kit include reagents for practicing the method, and can include one or more of a capture molecule, such as a capture antibody, a specific binding agent, such as a detection antibody, nanoparticles conjugated to a tag, an enzyme sensitive to the metal ion of the nanoparticles, and a signal generating substrate for the enzyme. The kit may optionally include reaction wells, such as reaction plates or Eppendorf tubes and buffers, washes, and other reagents needed to practice the method. A kit may also include one or more reagents for practicing the disclosed miRNA detection procedure, such as magnetic microbeads, LNA probes, reagents and compositions for poly(A) polymerase reaction for polyadenylation, a detection antibody, nanoparticles conjugated to a tag, an enzyme sensitive to the metal ion of the nanoparticles, and a signal generating substrate for the enzyme.

Embodiments of the apparatus include structures for practicing the methods described herein, and can include reaction wells, such as reaction plates and Eppendorf tubes, as well as devices for detecting the signal from the substrate.

Embodiments of the system include structures and reagents for practicing the methods described herein. The disclosed techniques possess a high detection resolution, and offer the advantage of straightforward operation with simple preparation of nanoparticles and no enzyme immobilization.

EXAMPLES

Example 1

Fluorescence Signal Transduction Mechanism for Immunoassay Based on Zinc Ion Release from ZnS Nanocrystals This example demonstrates fluorescence signal transduction mechanism for an immunoassay based on zinc ion release from ZnS nanocrystals. In this example, a fluorescence signal transduction mechanism based on cation release from ZnS nanocrystals was developed for sandwich immunoassay. In this mechanism, ZnS nanocrystals as labels in immunoassay are dissolved by acid to release zinc ions. After pH adjustment of the dissolving solution using a basic solution, zinc-ion sensitive fluorescence indicator Fluozin-3 is added to bind with the released zinc ions for sensitive fluorescence measurement. Using mouse IgG as a model analyte, the immunoassay adopting this signal transduction mechanism demonstrates a low detection limit around 1 pM and a detection range with two orders of magnitude (1 pM to 0.5 nM).

Disease biomarkers and pathogenic biological agents are often present at ultra-low levels in samples and require highly sensitive detection methods. Immunoassay is a representative tool for this purpose. In immunoassay, the antibodies are immobilized on solid supporting materials (microplate wells or beads); after a sandwich or competitive immunoreaction, labels are attached to captured analytes or transducer surface; quantification of analytes is generally achieved by measuring the specific activity of labels, such as their redox activity or enzyme catalytic kinetics. To further improve immunoassay sensitivity or lower detection limit, many nanomaterials have been recently employed to enhance the transducing signals of antibody-antigen interactions. Typical nanomaterials for the assay signal enhancement are gold nanoparticles, carbon nanotubes, silica nanoparticles, liposome nanoparticles, and semiconductor nanocrystals. Among these nanomaterials, semiconductor nanocrystals were paid particular attentions due to their versatile optical or electrochemical properties. Some semiconductor nanocrystals are fluorescent and much brighter than conventional organic fluorophores. Therefore, they have been used as fluorophore labels for signal enhancement in immunoassay. On the other hand, semiconductor nanocrystals are chemically composed of heavy metal ions such as $Cd^{2+}$, and they can be dissolved using acid to release thousands or even millions of heavy metal ions for electrochemical detection using mercury thin film electrodes. Therefore, these semiconductor nanocrystals conjugated with antibodies are used as signal amplifiers in electrochemical immunoassay. In electrochemical immunoassay, semiconductor nanocrystals are not necessarily fluorescent, and their preparation is simplified because controlling surface defects of nanocrystals is not essential.

Recently, it has been shown that the heavy metal ions replaced from semiconductor nanocrystals using cation exchange reaction can bind with a fluorescence indicator to generate fluorescence for signal transduction. Such an approach is of significance because it takes advantages of heavy metal ion release for signal amplification, adopts sensitive fluorescent measurement, avoids highly toxic mercury thin film electrodes in sensing, and eases the nanocrystal synthesis conditions. However, alternative low toxic semiconductor nanocrystals, fluorescence indicators with high specificity to the released heavy metal ions, and simple cation release approaches are still of interest for further investigation.

In this example, the appropriate reaction conditions for zinc ion detection using Fluozin-3 were investigated, the synthesis and bioconjugation of ZnS nanocrystals were presented, the assay parameters were optimized, and the assay detection limit and detection range were characterized. The detailed methods, results and their explanation, and conclusions are presented in the following sections below.

Chemicals and Apparatus $Zn(NO_3)_2$, $ZnCl_2$, thioglycolic acid (TGA), thioacetamide, trace metal grade 12 M HCl, trace metal grade NaOH, and Tris (hydroxymethyl) aminomethane were from Sigma Aldrich (St. Louis, Mo.). $CaCl_2$, KCl, $KNO_3$, $PbCl_2$, $NaH_2PO_4$, $Na_2HPO_4$, NaCl, NaOH, $NaN_3$, $MgCl_2.6H_2O$, $Na_2S_2O_3.5H_2O$, Tween 20, HEPES (N-(2-Hydroxyethyl) piperazine-N'-2-ethanesulfonic Acid), Glacial acetic acid, Ethylenediaminetetraacetic acid (EDTA), Dimethyl sulfoxide (DMSO) and Fluorescein-di-β-D-galactopyranoside (FDG) were from Fisher Scientific (Pittsburgh, Pa.). 1-ethyl-3-(3-dimethylamino-propyl) carbodiimide (EDC), N-hydroxysuccinimide ester (NHS), NeutrAvidin, Magnabind goat anti-mouse IgG, biotinylated goat anti-mouse IgG $F(ab')_2$, whole molecule mouse IgG, and 20× borate buffer were from Pierce (Rockford, Ill.). IgG and protease free bovine serum albumin (BSA) was from Jackson ImmunoResearch (West Grove, Pa.). Fluozin-3 and streptavidin beta-galactosidase conjugate were from Invitrogen (Carlsbad, Calif.).

HEPES solution contained 0.020 M HEPES and 0.135 M NaCl with a natural pH 5.5 (in studies, when necessary, the pH of HEPES solution was adjusted using HCl or Tris base). PBS-R buffer contained 0.044 M $NaH_2PO_4$, 0.056 M $Na_2HPO_4$, 0.1 M NaCl, 1% BSA, 0.5% Tween 20 and 0.003 M $NaN_3$ in DI water with pH 7.4 (PBS-R buffer has 1% BSA unless otherwise specified). PBS-D buffer was made of 0.044 M $NaH_2PO_4$, 0.056 M $Na_2HPO_4$, 0.1 M NaCl, 0.005 M $MgCl_2.6H_2O$ and 0.003 M $NaN_3$ in DI water with pH 7.4. 50×TAE buffer was prepared by dissolving 24.2 g Tris base, 7.32 g EDTA, and 5.7 mL Glacial acetic acid into 100 mL of DI water. 0.002 M FDG solution was prepared before use by diluting 394 µL of 1 mg/mL FDG (dissolved in a mixture of ethanol and DMSO in 50%:50% volume ratio) into 2.606 mL of PBS-D buffer.

96-well microplates from Fisher Scientific and a Perkin Elmer (Waltham, Mass.) Victor 3 microplate reader with a light source (340 nm to 1000 nm) were used for fluorescence measurement. A bandpass excitation filter centered at 485 nm (bandwidth=14 nm) and a bandpass emission filter at 520 nm (bandwidth=25 nm) were used for fluorescence measurement. An UV-Vis spectrophotometer UV-2450 with a light source (190 nm to 900 nm) from Shimadzu (Kyoto, Japan) was used for absorbance measurement. Zinc sulfide nanocrystals were imaged using a Hitachi (Tokyo, Japan) S-4700 field-emission scanning electron microscope (SEM).

Zinc Ion Detection Using Fluozin-3

To investigate the potential effects of solution pH on the detection limit of the zinc ion assay using Fluozin-3, the following steps were performed. First, HEPES solution was prepared and its pH was adjusted to 2 using HCl. 0.1 g/mL Tris in DI water was then added into the solution to generate HEPES solutions with distinct pH values (3.5, 4.0, 4.5, 5.0, 5.5, 6.0, 6.5, 7.0). Second, the wells of a microplate were washed using 1×TAE buffer to remove divalent ion contaminants in the wells. After TAE wash, the wells were washed out using HEPES pH7.0 to remove residual TAE. Third, for each pH condition of HEPES solutions, 50 µL of 0 nM, 100 nM and 500 nM $ZnCl_2$ were prepared in that pH condition and added to the wells. After $ZnCl_2$ addition, 50 µL of 2.5 µM Fluozin-3 prepared in the same pH condition were added to the wells. Fourth, the microplate was vortexed for several minutes and placed in the plate reader for fluorescence measurement. During data processing, the measured fluorescence signals were plotted versus pH. The signal for 0 nM $ZnCl_2$ in each pH condition actually was the background in that pH condition. On the basis of the plot, the pH condition achieving the maximum signal/background ratio was further used as an optimized condition in all later experiments using the zinc ion and Fluozin-3 reaction.

To investigate the detection limit and the detection range of the zinc ion assay, serial dilutions (0~5 µM) of $ZnCl_2$ were prepared in HEPES solution using the optimized pH condition. 50 µL of each concentration of $ZnCl_2$ were added to the wells of a microplate. 50 µL of 2.5 µM Fluozin-3 prepared in the same HEPES solution was added to each well and reacted with $ZnCl_2$. After vortexing for several minutes, the microplate was put into the microplate reader for fluorescence measurement. The above studies were performed in triplicate.

Zinc Sulfide Nanocrystal Synthesis and Bioconjugation

Zinc sulfide nanocrystals were synthesized with a simple approach by following the reported procedures with slight modifications. Prior to the addition of any reagents, a 3-neck flask was thoroughly washed with 1×TAE and further rinsed with DI water. After the flask was washed, 0.075 g of $Zn(NO_3)_2$ were added to 50 mL of DI water in the flask under constant stifling, and then 114 µL of TGA was added into the stirred solution. 2 M NaOH prepared in DI water was dropwise added to the solution until a pH measurement of 11.5 was attained. After the pH was adjusted, the solution was deoxygenated using a slow nitrogen drip. After 15 minute of nitrogen dripping, 0.0012 g of thioacetamide dissolved in 20 mL of DI water were added to the flask. Thereafter, the flask was sealed with stoppers and the solution was continuously stirred and maintained at 50° C. overnight. After overnight growth, ZnS nanocrystals were concentrated 10 times using centrifuge at 10,000×g, and washed with 1× borate buffer.

To achieve the bioconjugation of ZnS nanocrystals with NeutrAvidin, the following steps were performed. First, 500 µL of the concentrated ZnS nanocrystals (in 1× borate buffer) were mixed with 100 µL of 20 mM EDC and 20 µL of 200 mM NHS at room temperature for 15 minutes. Second, after the mixing, the nanocrystals were washed 5 times with 1× borate buffer using centrifuge to remove excess EDC and NHS. Third, the surface activated nanocrystals were incubated with 0.5 mL of 0.25 µM NeutrAvidin at room temperature for 2 hours. During the 2-hour incubation, stable amide bonds were formed between NeutrAvidin and the nanocrystals. Fourth, the conjugated nanocrystals were washed and resuspended in 500 µL of 1× borate buffer. The conjugated nanocrystals were stored as stock at 4° C. and used within 2 weeks.

Immunoassay for Mouse IgG Using ZnS Nanocrystals as Signal Transducers

The study was performed as follows. First, the wells of a microplate were blocked overnight at 4° C. using PBS-R buffer with 5% BSA. After blocking, 5 µL of Magnabind beads coated with goat anti-mouse IgG were added to the wells and washed with 50 µL of PBS-R buffer. Second, 50 µL of mouse IgG in the concentration range from 0 to 1 nM were prepared in PBS-R buffer, added to the wells, and vortexed for 30 minutes. After mouse IgG capture by the beads, the beads were pulled down using magnets and washed 3 times using PBS-R buffer. Third, 50 μL of 30 nM biotinylated anti-mouse IgG was prepared in PBS-R buffer and then added to each well and incubated for 30 minutes. The formed sandwich immunocomplexes were washed 3 times using PBS-R buffer. Fourth, the immunocomplexes were blocked using PBS-R buffer with 5% BSA for 30 minutes. After blocking, 50 μL of NeutrAvidin conjugated ZnS nanocrystals (1000× diluted from the stock solution using HEPES pH 7 with 0.05% Tween 20) were added to each well and incubated with the beads for 5 minutes. After incubation, the beads were washed 5 times using HEPES pH 7 with 0.05% Tween 20. Fifth, further washing of the beads with 1×TAE containing 0.05% Tween 20 was performed to remove any possible free divalent ion contaminants from the beads or the microplate wells. After TAE wash, the beads were further washed using HEPES pH7 to remove residual TAE. Sixth, after the supernatant was removed from each well, 50 μL of HEPES pH 2 were added to each well to dissolve nanocrystal labels. After dissolution of nanocrystal labels, the pH of the dissolving solution in the wells was adjusted to 5.5 using HEPES pH 7 with an appropriate volume (150 μL). Finally, 20 μL of 10 μM Fluozin-3 in HEPES pH5.5 were added to each well. After vortexing the microplate for several minutes, the beads were pulled down using magnets and the supernatant was collected for fluorescence measurement. The above study was performed in triplicate.

Specificity of Fluozin-3 to Zinc Ions

A microplate was washed using 1×TAE buffer to minimize potential divalent ion contaminants in wells, and the wells were further washed using HEPES pH5.5 to remove residual TAE. Second, 10 nM $ZnCl_2$, 100 nM $NaH_2PO_4$, 100 nM $PbCl_2$, 100 nM $CaCl_2$, 100 nM $MgCl_2$, 100 nM $KNO_3$, 100 nM KCl, and 100 nM EDTA were prepared in HEPES pH5.5. Third, 50 μL of each chemical solution, including a blank (just HEPES pH5.5), were added to the wells, and sequentially 50 μL of 2.5 μM Fluozin-3 (prepared in HEPES pH5.5) were added to each well to react with chemical ions. After several minutes vortexing, the microplate was put into the microplate reader for fluorescence measurement. This study was performed in triplicate.

Figure 6:
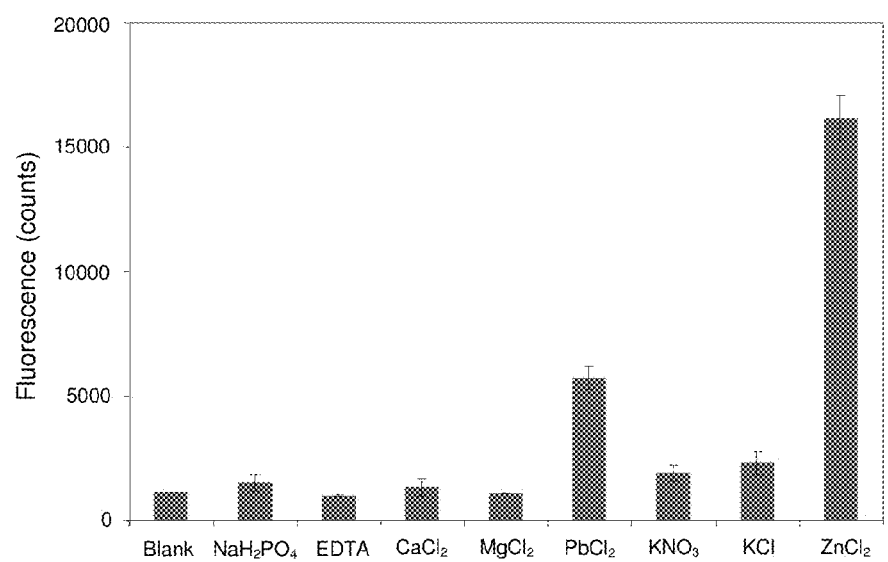
FIG. 6 is a bar graph illustrating the fluorescence signals generated from the reaction between Fluozin-3 and all tested chemicals demonstrating the potential interferences of other ions or chemicals on the reaction of zinc ion and Fluozin-3.

FIG. 6 shows the fluorescence signals generated from the reaction between Fluozin-3 and all tested chemicals.

Optimization of Detection Antibody Concentration in Immunoassay

Ten μL of Magnabind beads conjugated with goat anti-mouse IgG were added to the wells of a microplate and washed three times using PBS-R. Second, 50 μL of 1 μM mouse IgG were added to each well for 30 minute antigenic capture by the beads. After the incubation, the beads were washed using PBS-R. The bead surface in each well was saturated with mouse IgG. Third, 50 μL of detection antibody (biotinylated goat anti mouse IgG) prepared in a wide concentration range (from 0 to 1 μM) were added to the wells and incubated with the beads for 30 min, and then the beads were washed 3 times using PBS-R. Fourth, 50 μL of 0.03 mg/mL streptavidin beta-galactosidase conjugate were added to each well to bind with detection antibody for 5 minutes. The beads were washed three times with PBS-R followed by two washes using PBS-D. Fifth, the beads were re-suspended in 20 μL of PBS-D, and 100 μL of 0.2 mM FDG were added to each well for 30 second incubation. The enzyme reaction was quenched using 100 μL of 5×TAE. Finally, the beads were pulled down and 100 μL of the supernatant were transferred to each well for fluorescence measurement. This study was performed in triplicate.

Figure 7:
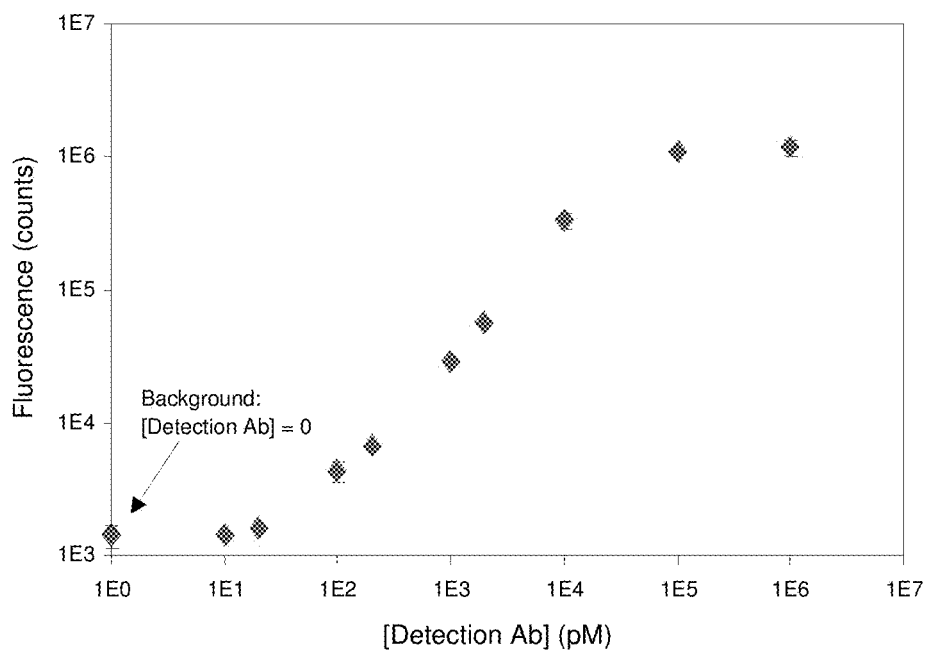
FIG. 7 is a plot to study the maximum loading of detection antibody (biotinylated goat anti mouse IgG) when beads were saturated with antigen mouse IgG

FIG. 7 shows the fluorescence signal vs. the concentration of detection antibody. In FIG. 7, the turnover point for signal saturation, which was estimated at around 30 nM, was considered as the maximum loading concentration of detection antibody on the bead surface.

Maximum Enzyme Concentration in Immunoassay

Ten μL of Magnabind beads conjugated with goat anti-mouse IgG were added to the wells of a microplate and washed three times with PBS-R. Second, 50 μL of 1 μM mouse IgG were added to each well to incubate with the beads for 30 min, and then the beads were washed three times using PBS-R. Third, 50 μL of 100 nM biotinylated detection antibody, was added to each well and incubated with the beads for 30 minutes. Fourth, after the beads were washed, 50 μL of serial dilutions of streptavidin beta-galactosidase conjugate in the concentration range of 0 to 0.1 mg/mL were added to each well and incubated with the beads for 5 min. The beads were further washed using PBS-R and PBS-D. Fifth, the beads were re-suspended in 20 μL of PBS-D, and 100 μL of 0.2 mM FDG were added to each well for 30 second incubation. Sequentially, the enzyme reaction was quenched using 100 μL of 5×TAE and 100 μL of the supernatant were transferred to new wells for fluorescence measurement. This study was performed in triplicate.

Figure 8:
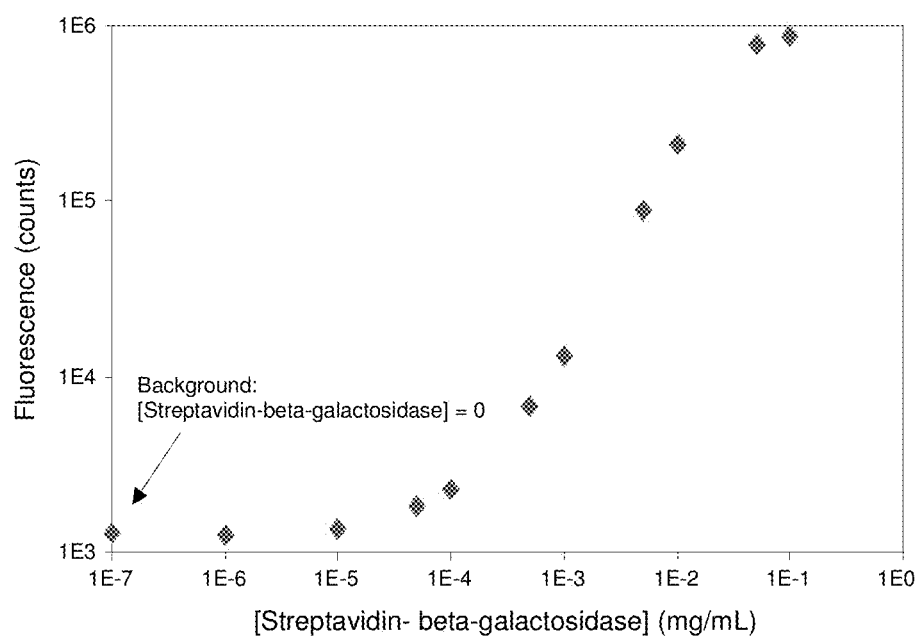
FIG. 8 is a plot to study the maximum loading of streptavidin conjugated beta-galactosidase when beads were saturated with antigen mouse IgG and biotinylated anti mouse IgG detection antibody.

FIG. 8 demonstrates the fluorescence signal vs. the concentration of enzyme. In FIG. 8, the turnover point for signal saturation, which was estimated at around 0.03 mg/mL, was considered as the maximum loading concentration of enzyme on the bead surface when saturating concentrations of capture antibody, antigen, and detection antibody were used during immunoassay.

Effects of TAE on Immunoassay

To investigate the possible negative effects of TAE on immunocomplexes (e.g., causing the dissociation of immunocomplexes), the following steps were conducted on the basis of enzyme-based immunoassay. Two identical bead sets were prepared during steps one through four. First, 10 μL of Magnabind beads conjugated with goat anti-mouse IgG were added to the wells of the plate and washed. Second, 50 μL of serially diluted mouse IgG in the concentration range of 0 to 1000 nM were added to each well and incubated with the beads for 30 minutes. After incubation, the beads were further washed. Third, 50 μL of 100 nM biotinylated detection antibody were added to each well and incubated with the beads for 30 min, and afterwards the beads were washed. Fourth, 50 μL of 0.03 mg/mL streptavidin beta-galactosidase conjugate were added to each well and incubated with the beads for 5 min, and the beads were further washed. Fifth, one set of the beads (or the immunocomplexes) prepared through the above four steps was washed with 1×TAE containing 0.05% Tween 20, and concurrently the other set of the beads was washed with PBS-R. Sixth, two sets of beads were further washed with PBS-R and then PBS-D. Each set of the beads were re-suspended in 20 μL of PBS-D, and 100 μL of 0.2 mM FDG was added to each well for 30 second incubation. The enzyme reaction was quenched with 100 μL of 5×TAE. Finally, 100 μL of the supernatant were transferred to new wells for signal measurement. This study was performed in triplicate.

Figure 9:
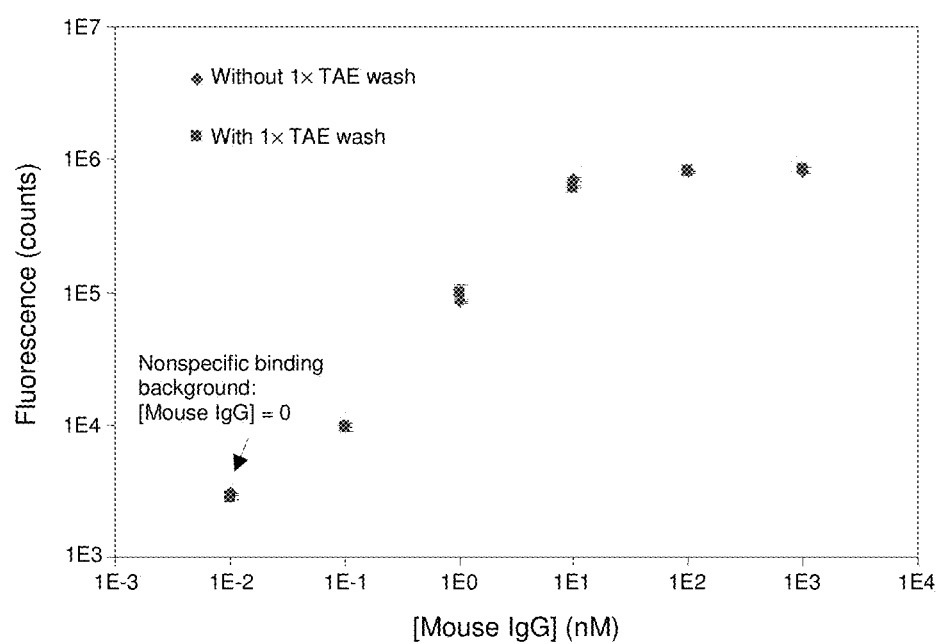
FIG. 9 illustrates the calibration curves of immunoassay on mouse IgG with the optimized concentrations of detection antibody and enzyme—the first curve (diamond) presenting the data of the assay in which immunocomplexes were not washed with TAE buffer; the second curve (square) shows the data of the assay in which immunocomplexes were washed with TAE buffer.

FIG. 9 demonstrates two assay calibration curves with and without TAE wash of immunocomplexes, respectively. It is shown that 1×TAE containing 0.05% Tween 20 did not impact the outcome of immunoassay and its potential negative effects were not relevant. FIG. 9 also shows that the maximum loading concentration of antigen on the bead surface was around 10 nM.

Zinc Ion Detection Using Fluozin-3

Figures 2A, 2B:
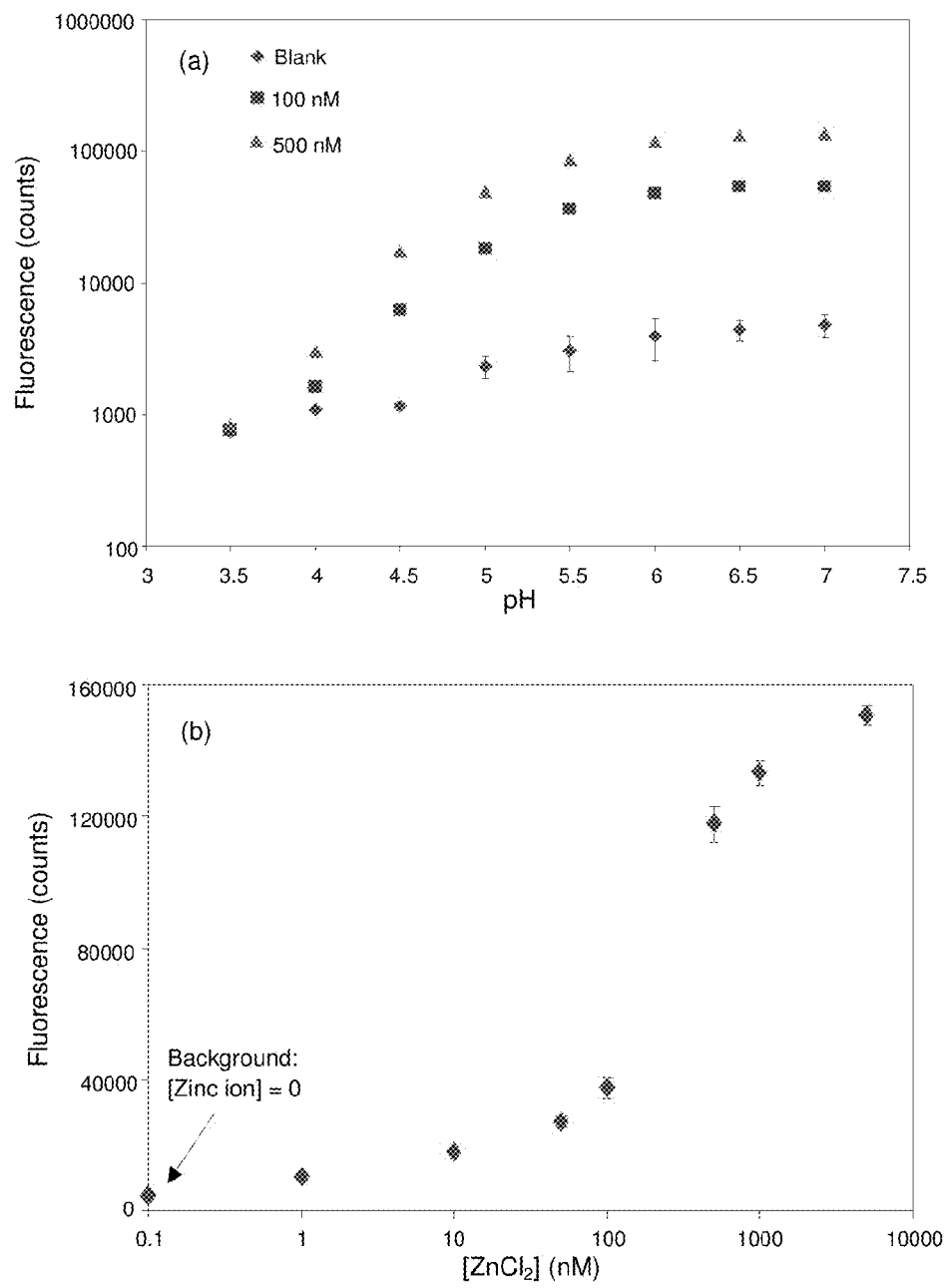
FIG. 2A illustrates the pH effect of reaction solution on the fluorescence signals generated from the reaction of zinc ion and Fluozin-3.
FIG. 2B is the calibration curve for the zinc ion detection using Fluozin-3 under the optimized pH condition (pH=5.5).

Fluozin-3 is a fluorescence indicator of zinc ions. Fluozin-3 itself has a minimal fluorescence background, but generates strong green fluorescence (emission peak at ~520 nm) when bound with free zinc ions. Optimization of the solution pH condition for the zinc ion assay using Fluozin-3 was necessary to achieve a maximum signal/background ratio, which ensured a low detection limit for zinc ions. FIG. 2A demonstrates the measured fluorescence signal versus the pH value of the reaction solution. For each $ZnCl_2$ concentration, the fluorescence signal escalated as the pH value increases from 3.5 to 5.5, but became saturated at pH 5.5 or above. Probably, under strongly acidic conditions, excessive protonation prevented the binding between zinc ions and Fluozin-3 or destroyed the molecular structure of Fluozin-3. Under each pH condition, taking the fluorescence signal of 0 nM $ZnCl_2$ as background, the signal/background ratios for 100 and 500 nM $ZnCl_2$ were calculated. It was found that the ratios show the same trend as their fluorescence signals versus the pH value. Therefore, the pH value in the range of 5.5~7.0 was selected as the optimized condition in the successive studies. However, relatively acidic conditions may prevent the binding between zinc ions and antibodies in immunoassay adopting the proposed signal transduction mechanism. Therefore, pH 5.5 was determined to be the optimized condition in this research.

To investigate the detection limit and the detection range of the zinc ion assay, serial dilutions of $ZnCl_2$ in the concentration range of 0-5000 nM were prepared and reacted with Fluozin-3 in HEPES pH 5.5. FIG. 2B shows the calibration curve of the zinc ion assay. On the basis of three times the deviation of the blank, the detection limit on zinc ions was estimated to be less than 1 nM. Considering each ZnS nanocrystal can release a high number of zinc ions, the immunoassay using ZnS nanocrystals as signal transducers achieves a lower detection limit on analytes. Furthermore, FIG. 2B demonstrates a wide zinc ion detection range from 1-5000 nM.

To verify the specificity of Fluozin-3 to zinc ions, $ZnCl_2$ and other metal ions or chemicals ($NaH_2PO_4$, $PbCl_2$, $CaCl_2$, $MgCl_2$, $KNO_3$, KCl, and EDTA) were prepared and mixed with Fluozin-3 in HEPES pH 5.5. In this study, the concentration of other metal ions or chemicals is ten times higher than that of $ZnCl_2$. The specificity data is shown in FIG. 6. As shown in FIG. 6, the signals caused by $CaCl_2$, $MgCl_2$, EDTA, and $NaH_2PO_4$ are comparable to the blank background. There was an unexpected response from the reaction of Fluozin-3 with potassium and lead ions—the fluorescence signals caused by potassium ions and lead ions were about two and six times the background, respectively. Therefore, chemicals containing potassium ions and lead ions in buffers should be avoided.

ZnS Nanocrystal Synthesis and Bioconjugation

ZnS nanocrystals were synthesized with thioacetamide as the sulfide source and zinc nitrate as the zinc source. TGA was used in the synthesis as the matrix for a resultant carboxylated coating on the nanocrystal surface through the binding between the thiol group of TGA and zinc atoms on the nanocrystal surface. Carboxylation of nanocrystals makes their surface hydrophilic in aqueous solution and therefore enhances the colloidal stability of nanocrystals. On the other hand, the carboxyl groups on the nanocrystal surface allow conjugation with NeutrAvidin (or other proteins) through the cross linking reaction with EDC and NHS.

Figure 3:
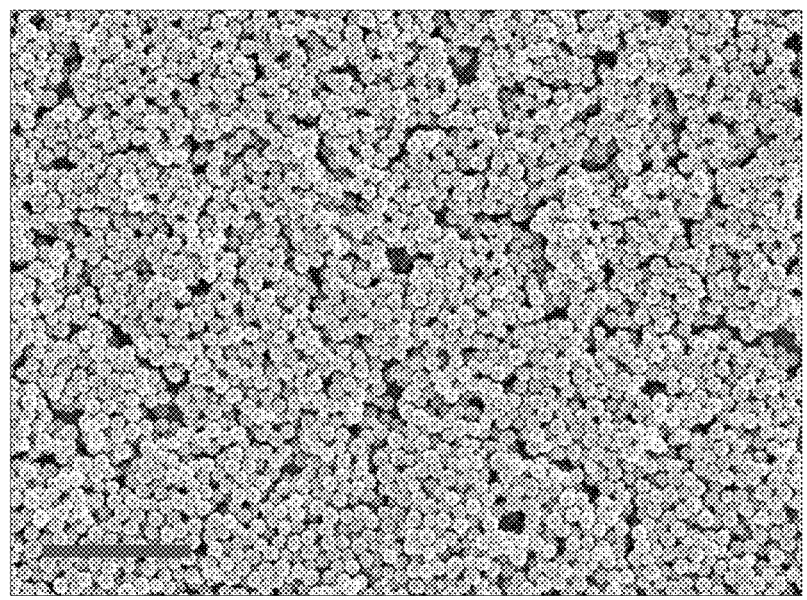
FIG. 3 is a scanning electron microscope (SEM) image of the synthesized ZnS nanocrystals with an approximate 50 nm diameter (the bar in the image is in 500 nm scale).

FIG. 3 shows the SEM image of ZnS nanocrystals with an average diameter of 50 nm prior to bioconjugation. These nanocrystals had a uniform spherical shape. To estimate the concentration of the stock ZnS nanocrystals, the stock nanocrystals (after wash using HEPES pH7) were dissolved and serially diluted in HEPES pH 2. After the pH adjustment (from pH2 to pH5.5) of the dissolving HEPES solution, Fluozin-3 was added to all zinc solutions to generate fluorescence. The resultant fluorescence responses were interpolated into a calibration curve established using $ZnCl_2$ and Fluozin-3. Through the interpolation, the concentration of zinc ions released from the stock nanocrystals was approximated. Considering possibly around two million zinc ions are contained in each ZnS nanocrystal, the concentration of the stock ZnS nanocrystals was estimated to be in the range of 1~5 nM.

Both conjugated and non-conjugated ZnS nanocrystals were monitored for colloidal stability using absorbance measurement. Non-conjugated ZnS nanocrystals stored in 1× borate buffer were found to be stable for more than two months after synthesis when stored at 4° C. However, the stability of bio-conjugated ZnS nanocrystals stored in 1× borate buffer was attained for around two weeks.

Optimization of Immunoassay Conditions

Excessive biotinylated detection antibody in immunoassay will increase the assay cost and also deteriorate the detection resolution by causing a high nonspecific binding background. It is therefore necessary to optimize the concentration of detection antibody in immunoassay. Instead of using ZnS nanocrystals as labels, enzyme (streptavidin conjugated beta-galactosidase) was used as labels in immunoassay to investigate the maximum loading of the detection antibody. FIG. 7 shows the plot to study the maximum loading of the detection antibody when 10 μL of stock Magnabind beads, 1 μM antigen mouse IgG, and 0.03 mg/mL enzyme were used in the study. In FIG. 7, the turnover point for signal saturation, which was estimated at around 30 nM, was considered as the maximum loading concentration of detection antibody in the presence of excess antigen (for 10 μL of stock beads). For immunoassay, 1 to 4 times the maximum loading concentration of detection antibody should be used.

In order to verify that the saturation fluorescence signals in FIG. 7 are not limited by the enzyme concentration (0.03 mg/mL) and the antigen concentration (1 μM), the maximum loading of antigen and the maximum loading of enzyme for 10 μL of stock beads as solid supports were also investigated. FIG. 8 presents the plot to study the maximum loading of enzyme when beads were sequentially saturated with the antigen mouse IgG and the detection antibody. From FIG. 8, the maximum loading concentration of enzyme, which was considered to be the turnover point for signal saturation, was estimated at around 0.03 mg/mL. FIG. 9 in the supplementary content shows the maximum loading of the antigen was around 10 nM.

In the immunoassay adopting the discovered signal transduction mechanism, 1×TAE containing 0.05% Tween 20 was used to wash ZnS nanocrystal labeled immunocomplexes in order to eliminate potential free zinc ion contaminants. The possible negative effects of TAE on immunocomplexes (e.g., causing the dissociation of immunocomplexes) was determined. The effects of TAE on immunocomplexes were investigated on the basis of the enzyme based immunoassay. FIG. 9 *i* shows two immunoassay calibration curves with the optimized concentrations of the detection antibody and the enzyme—the first curve presents the data of the assay in which immunocomplexes were not washed with TAE buffer; the second curve shows the data of the assay in which immunocomplexes were washed with 1×TAE containing 0.05% Tween 20 prior to further washes with PBS-R and PBS-D. Both curves overlap with each other, and therefore it was clear that 1×TAE containing 0.05% Tween 20 had no significant negative impacts on immunocomplexes.

Figure 4:
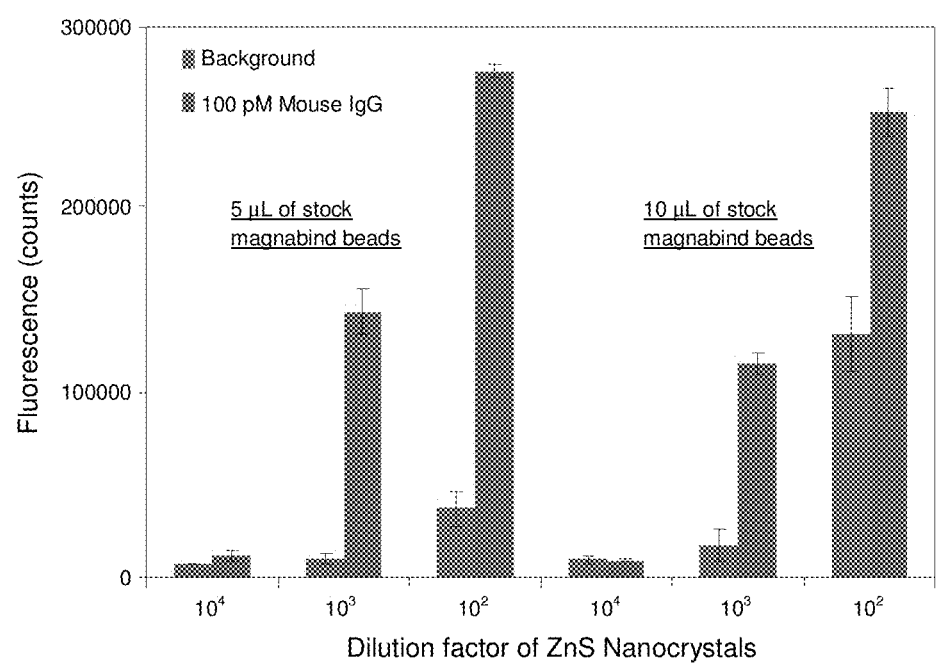
FIG. 4 is a bar graph of optimization of the concentration of ZnS nanocrystals in immunoassay to achieve a high signal/background ratio.

Similar to the detection antibody, the excessive NeutrAvidin conjugated ZnS nanocrystals can cause a high nonspecific binding background and therefore its concentration needs to be optimized. To investigate the appropriate ZnS nanocrystal concentration or dilution, an amount of stock Magnabind beads (5 or 10 µL) were sequentially incubated with 50 µL of 100 pM mouse IgG, 50 µL of 30 nM detection antibody and 50 µL of ZnS nanocrystals diluted from stock to form nanocrystal labeled immunocomplexes (bead washing was performed before each incubation step). The immunocomplexes were further mixed with 50 µL of HEPES pH2 to dissolve ZnS nanocrystal labels. After dissolution, the pH of the dissolving solution was adjusted to 5.5 using HEPES pH 7 with an appropriate volume, and 20 µL of 10 µM Fluozin-3 prepared in HEPES pH5.5 was added to the dissolving solution and reacted with the released zinc ions. The supernatant was collected for fluorescence measurement. The above experimental steps were synchronously performed for 0 pM mouse IgG without changing any other experimental conditions. The fluorescence signal measured for 0 pM mouse IgG is the nonspecific binding background. FIG. 4 shows the fluorescence signal of 100 pM mouse IgG and the background for different ZnS nanocrystal dilutions with 5 µL and 10 µL of stock Magnabind beads as solid supports, respectively. It is clear that the highest signal/background ratio was achieved under these conditions: (1) 1000× dilution of ZnS nanocrystals from stock; and (2) 5 µL of stock Magnabind beads as solid supports. These conditions were adopted for the present immunoassay using the disclosed signal transduction mechanism.

Figure 5:
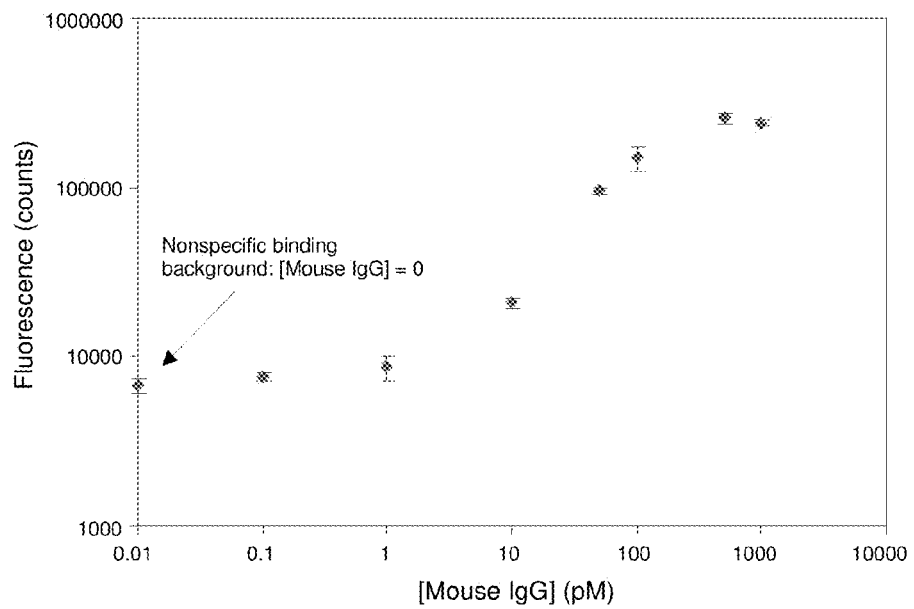
FIG. 5 is the calibration curve of immunoassay on mouse IgG using the signal transduction mechanism illustrated in FIG. 1

Calibration Characteristics of Immunoassay Using ZnS Nanocrystals as Signal Transducers To investigate the effectiveness of the proposed signal transduction mechanism for immunoassay, the immunoassay on mouse IgG was performed using the following optimized assay conditions: (1) 5 µL aliquots of $1 \times 10^8$ beads/mL (polyclonal goat anti mouse IgG conjugated Magnabind beads) as solid supports; (2) 30 nM biotinylated polyclonal anti mouse IgG as detection antibody; (3) 1000× diluted ZnS nanocrystals from stock as signal transducers; (4) HEPES pH5.5 as the reaction solution for zinc ions and Fluozin-3. FIG. 5 demonstrates the immunoassay calibration curve. On the basis of three times the deviation of the background, the detection limit of this immunoassay on mouse IgG was estimated to be around 1 pM (n=12). The immunoassay presented a maximum detection level of mouse IgG at around 0.5 nM. The detection range of this assay was of more than two orders of magnitude (1 pM to 0.5 nM).

In this example, a fluorescence signal transduction mechanism was developed for sandwich immunoassay using cation release from ZnS nanocrystals. Employing mouse IgG as a model analyte, the assay presents a detection limit around 1 pM and a detection range with more than two orders of magnitude. The signal transduction mechanism has the following merits. First, it achieved a high detection resolution. Second, it exhibited a high specificity to zinc ions and was not significantly sensitive to calcium or other common ions, and therefore alleviated the tedious work associated with buffer or reagent purification. Third, compared to electrochemistry-based signal transduction mechanisms adopting semiconductor nanocrystals (e.g., CdSe), it avoided toxic mercury electrodes for heavy metal ion detection and employed less toxic ZnS nanocrystals. Fourth, different from liposome nanoparticles, ZnS nanocrystals in this mechanism were robust and their size could be easily tuned. In addition, the acidic dissolution was a more generic approach for cation release.

Example 2

Facile Synthesis and Biosensing Application of Hybrid Zinc Nanoparticles

This example demonstrates facile synthesis and biosensing application of hybrid zinc nanoparticles. In particular, hybrid zinc nanoparticles were synthesized by adding thioglycolic acid (TGA) into a ZnO-particle synthesis procedure. Compared to the ZnO particles prepared without TGA, the hybrid nanoparticles were markedly different in their morphology, chemical composition, and growth kinetics. Moreover, they displayed colloidal stability and appropriate surface properties for bioconjugation. To demonstrate their biosensing application, the hybrid nanoparticles were conjugated and applied as biolabels or signal transducers in a sandwich immunoassay for mouse IgG. The immunoassay fluorescence signal was obtained by releasing zinc ions from these nanoparticle labels and further incubating the released zinc ions with zinc-sensitive fluorescence indicator Fluozin-3. The immunoassay disclosed herein has a dynamic detection range from 10 pM to 1 nM.

In the last decade, cadmium based semiconductor nanoparticles (e.g., CdSe, CdS, etc.) have been widely applied in biosensing. However, producing and employing cadmium-based compounds can be harmful to both humans and the environment. Thus, the search for new nanomaterials with low toxicity and versatile biosensing functionalities has become increasingly important. This work introduces the synthesis of one kind of zinc-based nanoparticles in an aqueous solution with low temperature, as well as their biosensing application. The zinc-based nanoparticles were synthesized by adding thioglycolic acid (TGA) into a mixture of zinc nitrate and ethanolamine in an aqueous solution. It is found that: without the addition of TGA, the mixture of zinc nitrate and ethanolamine produces ZnO particles; however, with the addition of TGA, the synthesized nanoparticles are markedly different from the produced ZnO particles in chemical composition, morphology, and growth kinetics. Here, the nanoparticles synthesized with the addition of TGA are called or defined as the hybrid zinc nanoparticles (or Zn—O—S—C nanoparticles) since they are composed of zinc, oxygen, sulfur and carbon. Further characterization has shown that the hybrid nanoparticles have colloidal stability and appropriate surface properties for bioconjugation. Compared to ZnO micro/nanoparticles which have poor water stability due to high water solubility and require complex surface modification before many bio-applications, the hybrid nanoparticles are of use in biosensing.

To demonstrate a biosensing application, the hybrid nanoparticles were bioconjugated and used as biolabels or signal transducers in a sandwich immunoassay for mouse IgG. Although these nanoparticle labels have fluorescence properties, an alternative signal transduction approach that releases zinc ions from these labels and further incubating the released zinc ions with a zinc-sensitive fluorophore Fluozin-3 for fluorescence measurement was found to be much more effective or sensitive in quantifying mouse IgG. In the following Example, the synthesis, characterization, and biosensing application of the hybrid nanoparticles are presented and discussed.

Chemicals and Instruments $NaH_2PO_4$, $Na_2HPO_4$, NaCl, $NaN_3$, Tween 20, HEPES (N-(2-Hydroxyethyl)piperazine-N'-2-ethanesulfonic Acid), Glacial acetic acid, ethyl alcohol, Ethylenediaminetetraacetic acid (EDTA), and Dimethyl sulfoxide (DMSO) were from Fisher Scientific (Pittsburgh, Pa.). $Zn(NO_3)_2$, Ethanolamine, Thioglycolic acid (TGA), trace metal grade 12 M HCl, trace metal grade NaOH, and Tris (hydroxymethyl) aminomethane were from Sigma Aldrich (St. Louis, Mo.). Neutravidin, 1-ethyl-3-(3-dimethylamino-propyl) carbodiimide (EDC), N-hydroxysuccinimide ester (NHS), Magnabind goat anti-mouse IgG, Biotinylated goat anti-mouse IgG F(ab')$_2$, whole molecule mouse IgG, and 20× borate buffer were from Pierce (Rockford, Ill.). IgG and protease free bovine serum albumin (BSA) was from Jackson ImmunoResearch (West Grove, Pa.). Fluozin-3 was from Invitrogen (Carlsbad, Calif.). All other chemicals were of reagent grade and used without further purification.

PBS-R buffer consisted of 44 mM $NaH_2PO_4$, 56 mM $Na_2HPO_4$, 100 mM NaCl, 1% BSA, 0.5% Tween 20 and 3 mM $NaN_3$ in DI water with pH 7.4. HEPES included of 20 mM HEPES and 135 mM NaCl, the pH of this solution is ~5.5, the pH was adjusted during experiments when necessary with HCl or Tris base. 50×TAE buffer was prepared by dissolving 24.2 g Tris base, 7.32 g EDTA, and 5.7 mL Glacial acetic acid into 100 mL of DI water.

All energy dispersive x-ray (EDX) spectra and scanning electron microscopy (SEM) images were collected using a Hitachi (Tokyo, Japan) S-4700 field-emission scanning electron microscope. An UV-Vis spectrophotometer UV-2450 with a light source (190 nm to 900 nm) from Shimadzu (Kyoto, Japan) was used for UV-Vis absorbance (UV-Vis) measurement. The fluorescence spectrum of the hybrid nanoparticles was performed using a Spex Fluorolog 3 fluorescence spectrometer (Edison, N.J.). A Perkin Elmer (Waltham, Mass.) Victor 3 microplate reader with a light source (340 nm to 1000 nm) was used for fluorescence measurements of 96-well microplates from Fisher Scientific. For measurement of hybrid nanoparticles a bandpass excitation filter centered at 355 nm (bandwidth=40 nm) and a bandpass emission filter (bandwidth=25 nm) centered at 460 nm were used. A bandpass excitation filter centered at 485 nm (bandwidth=14 nm) and a bandpass emission filter at 520 nm (bandwidth=25 nm) were used for fluorescence measurement of the reaction between Fluozin-3 and zinc ions.

Synthesis of Hybrid Nanoparticles

The preparation of the hybrid nanoparticles followed a straightforward approach. First, 50 mL of DI water were added to a 3-neck flask that had been cleaned with 1×TAE and thoroughly rinsed with DI water. The flask was placed on a hot plate and the temperature was brought to ~80° C. Afterwards, the DI water was deoxygenated using 10 minutes of nitrogen bubbling. Second, 0.023 g $Zn(NO_3)_2$ and 15.4 µL ethanolamine were dissolved in the deoxygenated DI water and stirred for about 1 min. To maintain an alkaline pH in the solution, 500 µL of 6 M NaOH were added to the flask, prior to the addition of 25 µL of TGA. Third, after the 30-min reaction, the hybrid nanoparticles were concentrated 35 times and washed 3 times in borate buffer with YM-10 centrifugal filters (Millipore) and centrifuge at 4400 rpm. The washed and concentrated hybrid nanoparticles were resuspended in 500 µL borate buffer and stored as stock at 4° C.

Bioconjugation of Hybrid Nanoparticles

50 µL of a 20 mM solution of EDC and 25 µL of a 10 mM solution of NHS were added to the washed and concentrated hybrid nanoparticles and reacted on a vortex at room temperature for 15 minutes. After EDC/NHS activation of the carboxylated surface, the activated hybrid nanoparticles were washed 5 times using borate buffer and centrifugation in a YM-10 centrifugal filter. Afterwards, the solution was resuspended in 500 µL of borate buffer and mixed with 500 µL of Neutravidin in borate buffer (1 mg/mL) on a vortex for 2 hours. After the 2 hour room temperature reaction, the bioconjugated hybrid nanoparticles were washed using centrifugation. Finally, after washing, the bioconjugated hybrid nanoparticles were resuspended in 1 mL borate buffer and stored at 4° C.

Immunoassay for Mouse IgG Using Hybrid Nanoparticles as Signal Transducers

The bioconjugated nanoparticles were applied as biolabels in a model assay of mouse IgG. The biolabels can release zinc ions to bind with zinc-sensitive fluorescence indicator Fluozin-3 for fluorescence signal transduction. To perform the immunoassay for the detection of mouse IgG, the following steps were performed. First, 300 µL of 1×TAE were added to the wells of a microtiter plate to bind any divalent metal ion contaminants in the wells. The wells were washed using DI water. After thoroughly rinsing out the wells, 2.5 µL of Magnabind magnetic beads coated with goat anti-mouse IgG were added to the wells and washed 2 times with PBS-R. 5% BSA prepared in PBS-R was added to each well to block the bead and well surfaces, and then the microplate was stored at 4° C. overnight. Second, after removing the BSA from the wells, serial dilutions of mouse IgG (1-1000 pM) were added to the wells in triplicate. The plate was placed on a vortex for 30 minutes for antigenic capture at room temperature. Third, the wells were washed 3 times with PBS-R to remove any unbound antigens. Subsequently, 50 µL of 5 µg/mL biotinylated goat anti-mouse IgG were added to the wells to form sandwich immunocomplexes. The biotinylated detection antibodies were incubated with the bead-antigen complexes for 30 minutes on a vortex at room temperature. The wells were washed with PBS-R to remove all of the excess unbound antibodies. Then, the beads in the wells were blocked using 5% BSA in PBS for 15 minutes. Fourth, the bioconjugated hybrid nanoparticles were diluted 25 times in HEPES buffer (pH 7.4) and added to all of the wells for labeling of the detection antibodies through Neutravidin-biotin binding. The bioconjugated hybrid nanoparticles were vortexed in the wells with the sandwich immunocomplexes for 5 minutes and any unbound residual hybrid nanoparticle labels were washed out using HEPES buffer (pH 7.4). Fifth, 50 µL of HEPES pH2 were added to the wells of the microplate to dissolve the hybrid nanoparticles releasing zinc ions. The pH of the dissolving solution was adjusted back to around 6 using a HEPES pH7.4 solution. After the pH adjustment, the released zinc ions were detected using 20 µL of 10 µM zinc ion specific fluorophore Fluozin-3 that was added to each well. Finally, the beads were pulled down with magnets and the supernatant was measured in the microplate reader.

Preparation and Characterization of Hybrid Nanoparticles

Figure 10A:
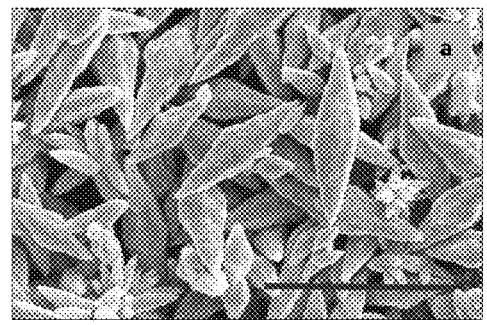
FIG. 10A is a scanning electron microscopy (SEM) image of ZnO particles synthesized with zinc nitrate and ethanolamine at pH 11.5 (bar=2 microns).
Figure 10B:
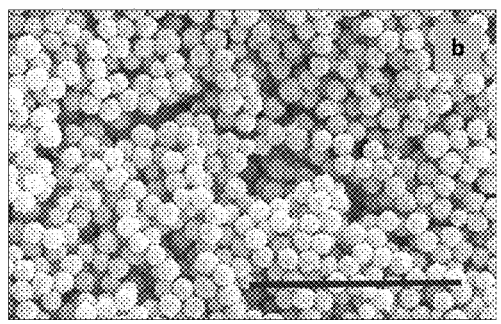
FIG. 10B is a SEM image of the hybrid nanoparticles under the same synthesis conditions as (a) but with the addition of TGA (bar=1 micron).
Figure 10C:
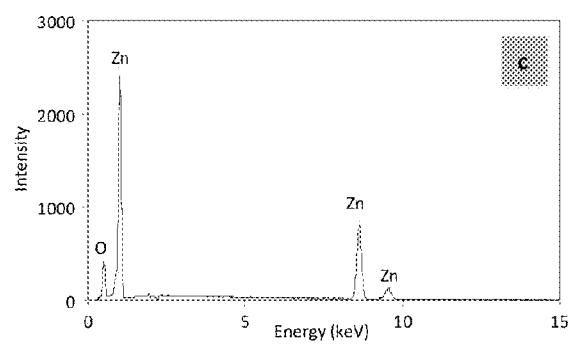
FIG. 10C is an energy dispersive X-ray (EDX) spectrum of ZnO particles.
Figure 10D:
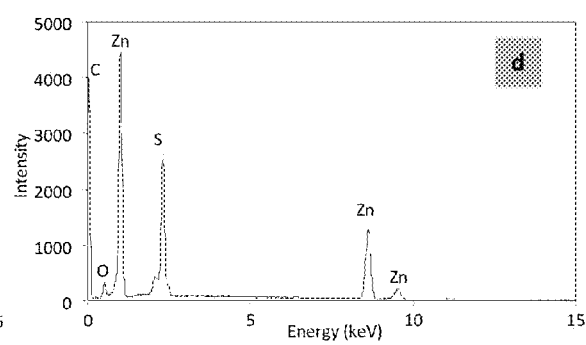
FIG. 10D is an EDX spectrum of the hybrid nanoparticles.
Figure 10E:
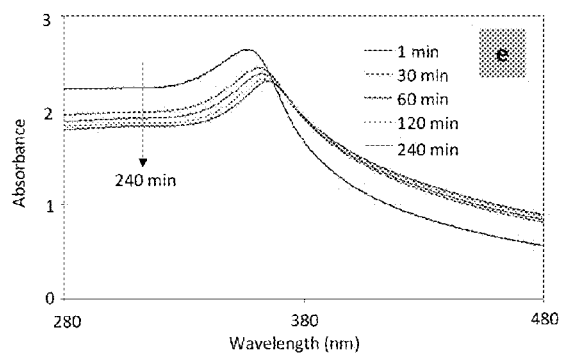
FIG. 10E is a UV-Vis absorbance spectra of ZnO particles synthesized for different time intervals.
Figure 10F:
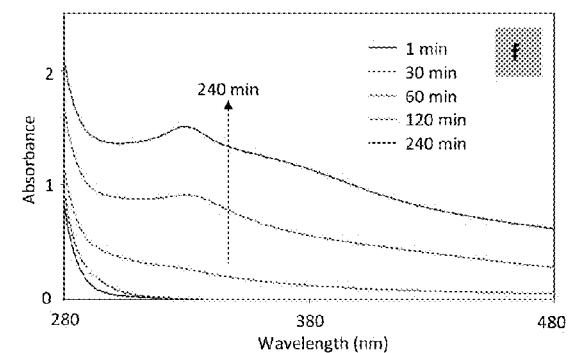
FIG. 10F is a UV-Vis absorbance spectra of the hybrid nanoparticles synthesized for different time intervals.

To investigate the role of TGA in synthesis, a comparison study was performed. In the study, ethanolamine and zinc nitrate were mixed in an aqueous solution at 80° C. for 1 minute to 240 minutes under two conditions: without TGA and with TGA. Without TGA addition, the reaction between ethanolamine and zinc nitrate was fast-white precipitates were formed within 30 minutes. With TGA addition, the reaction solution became opaque slowly. FIGS. 10A and 10B demonstrate representative SEM images of the synthesized structures under these two conditions (these structures underwent a 60-minute reaction before being collected for SEM imaging). As shown in the SEM images, the synthesized structures without TGA are of rhomboid-like shape and lack a well-defined size. However, with TGA in the reaction, the synthesized structures are nanospheres with very uniform shape and size. FIGS. 10C and 10D show the EDX spectra of the synthesized structures under the two synthesis conditions, respectively. FIG. 10C indicates that the rhomboid-like structures are ZnO particles because they contain only zinc and oxygen. The atomic percentage of Zn:O is 40%:60%. It is believed that the hydroxyl groups on the surface ZnO particles contribute more oxygen in the EDX analysis. FIG. 10D shows the EDX spectrum of the spherical nanoparticles which contain zinc, oxygen, sulfur, and carbon elements. The atomic percentage of Zn:S:O:C in the spherical nanoparticles is approximately 17%:17%:33%:33%. In addition, to better understand the particle growth kinetics without/with TGA, the reaction solution under each condition was collected at fixed time intervals during synthesis. For each time interval, the absorbance of these reaction solutions was measured using UV-Vis spectrophotometry. FIG. 10E shows that after 30 minutes of synthesis, the absorbance spectrum of the reaction solution became relatively fixed. This means that the growth of ZnO structures was rapid. On the contrary, when TGA is added to the reaction, as shown in FIG. 10F, the growth of nanoparticles was steady and easy to control.

From the data analysis above, it can be concluded that the addition of TGA to a regular ZnO synthesis procedure results in changes to the chemical composition, morphology, and growth kinetics of the synthesized structures. At the current stage, the synthesis mechanism involving TGA is being investigated. TGA and other thioacids have been used as stabilizers in the synthesis of semiconductor nanoparticles such as CdTe and PBS. Besides functioning as stabilizer, TGA was also reported to be able to react with heavy metal ions such as $Cd^{2+}$ to form a complex layer on CdTe nanoparticle surfaces. Thus, in this example, considering that zinc nitrate and ethanolamine can generate ZnO nuclei under alkaline and thermal conditions, it indicates that: (1) the thiol group of TGA could coordinate the surface of ZnO nuclei through thiol-metal binding, and thus control the shape and size of ZnO nuclei in the growth; and (2) TGA may also react with $Zn^{2+}$ in the solution generating the structure of the zinc thioglycolic acid complexes on the ZnO nuclei, and thus the synthesized products or nanoparticles are believed to be hybrid materials of zinc, oxygen, sulfur and carbon elements.

Figure 11:
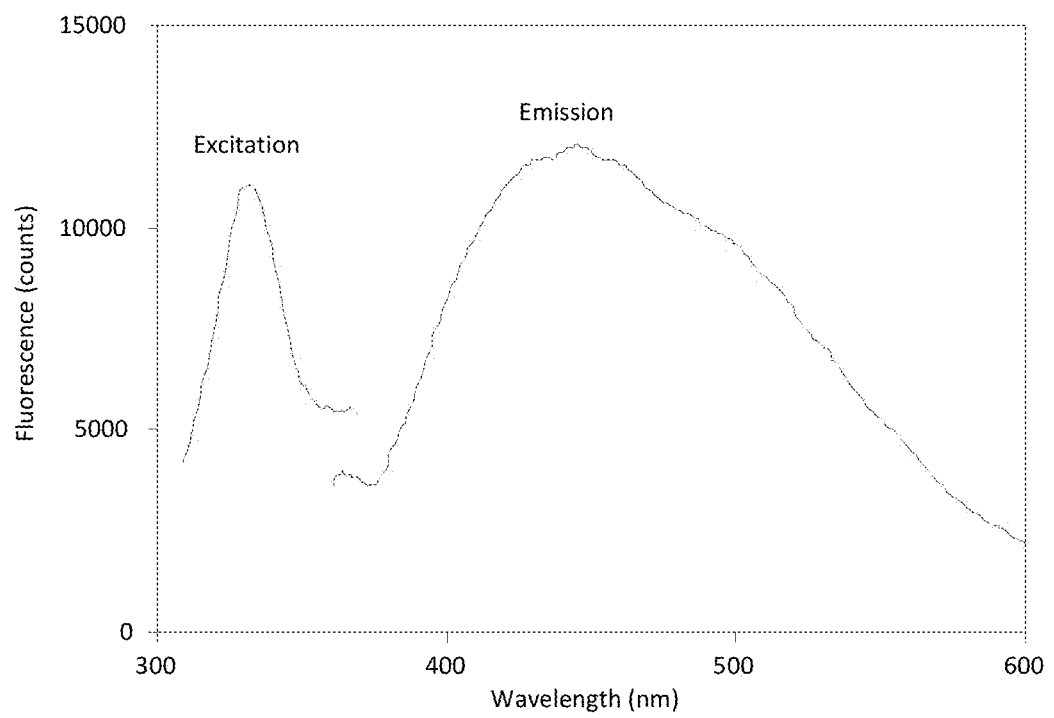
FIG. 11 includes fluorescence excitation and emission spectra for disclosed hybrid nanoparticles.

The hybrid nanoparticles were further characterized in three ways. First, the as-prepared hybrid nanoparticle were washed and incubated in borate buffer for one week, and then they were washed in ethanol and analyzed using SEM and EDX spectroscopy. The SEM image and the EDX spectrum of the incubated hybrid nanoparticles are the same as FIGS. 10B and 10D. Thus, the chemical composition of hybrid nanoparticles was found to be unchanged in borate buffer (or borate buffer would not etch hybrid nanoparticles). Second, the X-ray diffraction (XRD) analysis of hybrid nanoparticles was attempted, and no obvious XRD pattern was achieved. The reason is believed to be that the hybrid nanoparticles have low crystallinity due to the low temperature in synthesis. Third, the fluorescence properties of the hybrid nanoparticles were also investigated using a fluorescence spectrometer. FIG. 11 shows the fluorescence excitation and emission spectra of the hybrid nanoparticles. The excitation peak was in the UV range, and the emission peak is in the range of blue light. However, the observed blue emission is very weak (under 300-365 nm UV excitation), and the quantum yield of the hybrid nanoparticles was low and no more than 0.01%.

Colloidal Stability and Bioconjugation of Hybrid Nanoparticles

Figures 12A, 12B:
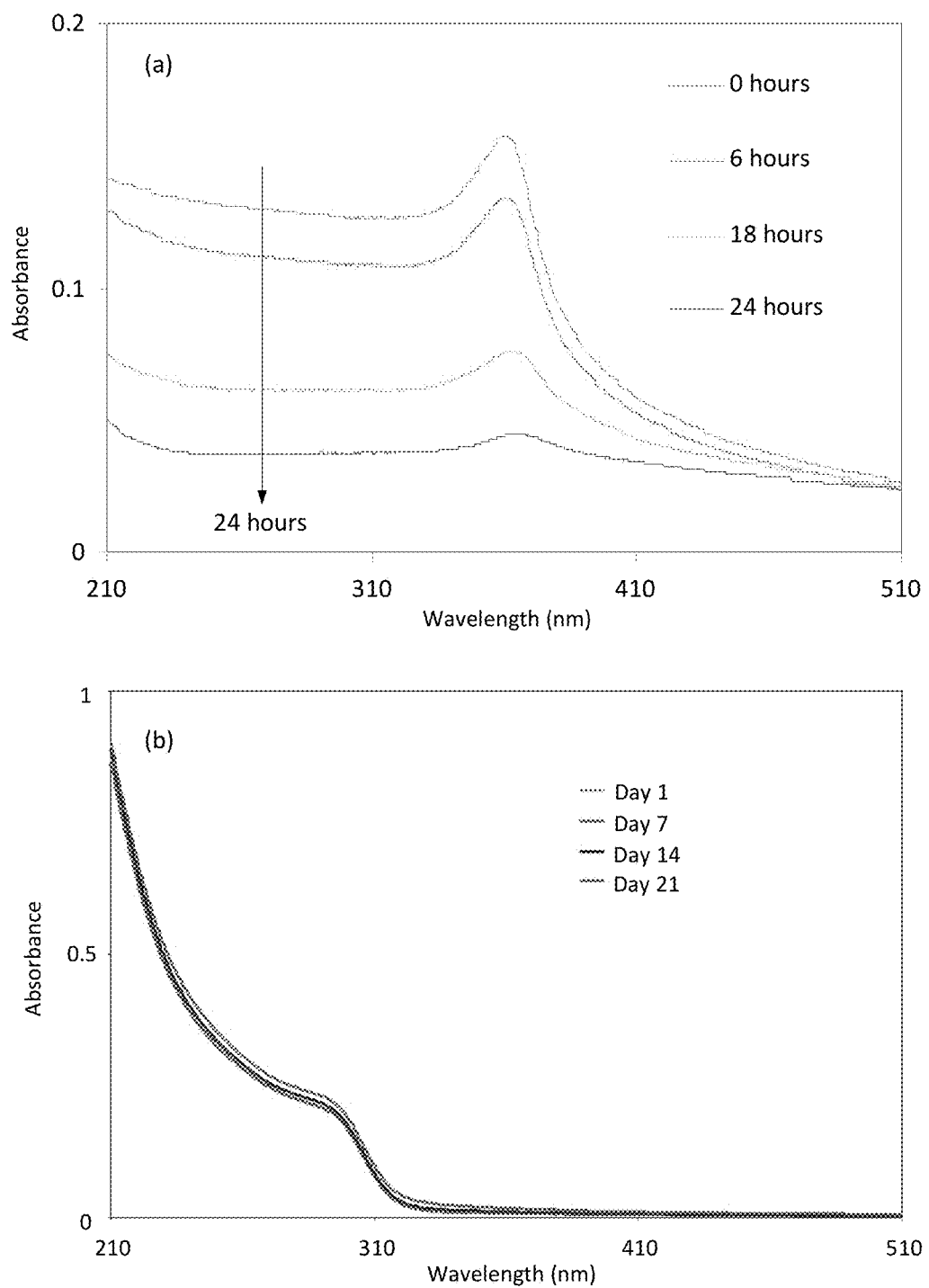
FIG. 12A is a UV-Vis absorbance of the as-prepared bare ZnO particles (without TGA in synthesis) in borate buffer versus time.
FIG. 12B illustrates colloidal stability of the hybrid nanoparticles in borate buffer by monitoring nanoparticle absorbance over 21 days.

The colloidal stability of nanoparticles refers to the balance of attractive and repulsive forces among nanoparticles. As a result, nanoparticles in solution are well dispersed, and are not apt to dissolve or aggregate. In this Example, the colloidal stability of the as-prepared nanoparticles was monitored using UV-Vis absorbance measurements. As a reference or comparison, 1 mg ZnO particles synthesized using zinc nitrate and ethanolamine were sonicated and suspended in 200 mL of borate buffer. The UV-Vis absorbance of the prepared solution was monitored for 24 hours. As shown in FIG. 12A, the absorbance of the suspended ZnO particles in borate buffer drops off versus time. Thus, the ZnO particles had no colloidal stability in borate buffer. On the contrary, FIG. 12B shows the absorbance data of the hybrid nanoparticles in borate buffer over three weeks. It can be seen that there was no significant change in absorbance, which indicates that the nanoparticles are stably dispersed in borate buffer. Since the hybrid nanoparticles were verified to be stable in borate buffer, they were prepared and stored for further bioconjugation and bioassay in this Example.

The hybrid nanoparticles were conjugated with Neutravidin using EDC/NHS cross-linking to create covalent bonds between the carboxyl groups on nanoparticle surfaces and amine groups in Neutravidin. Note that, the carboxyl groups on nanoparticle surfaces come from TGA coordinated on nanoparticle surfaces through the thiol-zinc binding, or could come from the zinc thioglycolic acid complexes formed on nanoparticle surfaces. After bioconjugation, in order to verify that Neutravidin molecules are indeed immobilized on nanoparticle surfaces, a study was performed. In the study, biotinylated magnetic microbeads were incubated with serial dilutions of Neutravidin conjugated and non-conjugated hybrid nanoparticles in a microplate. Non-conjugated hybrid nanoparticles in the study served as reference controls. After incubation, beads in the wells were thoroughly washed to remove any excess or unbound nanoparticles. An amount of HEPES pH 2 solution was added to the wells to dissolve the labels. After acidic dissolution, the pH in the wells was then adjusted to 6 using HEPES pH 7.4 solutions, and Fluozin-3 was added to each well to react with the released zinc ions for further fluorescence measurement.

Figures 13A, 13B:
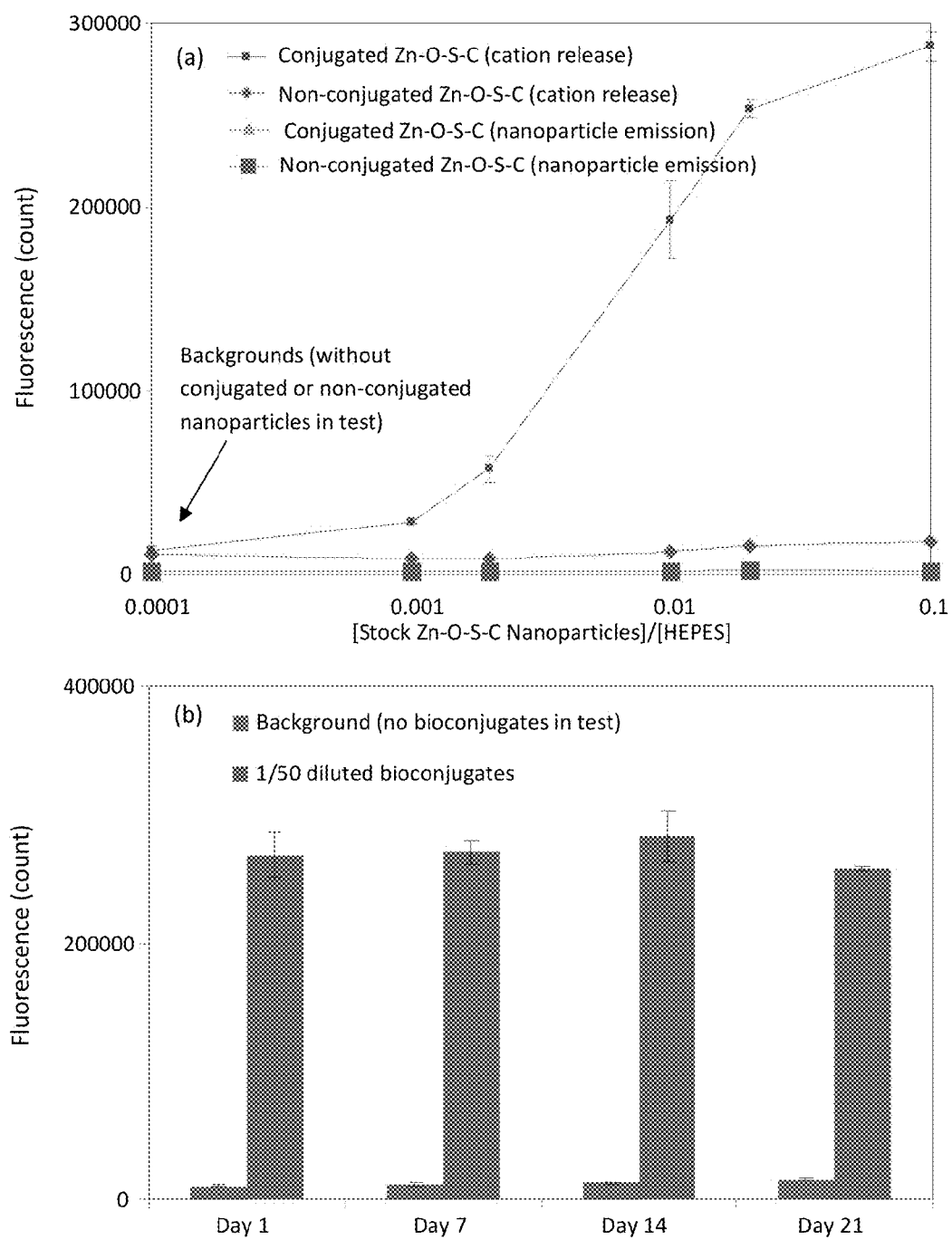
FIG. 13A provides fluorescence responses of serially diluted conjugated and non-conjugated hybrid Zn—O—S—C nanoparticles after being captured by biotinylated beads under two measurement modes: cation release (ex 488 nm, em 520 nm) and nanoparticle emission (ex 355 nm, em 460 nm).
FIG. 13B illustrates fluorescence signal stability of bioconjugated hybrid nanoparticles using cation-release based signal transduction.

FIG. 13A shows the cation-release based fluorescence signals for serially diluted conjugated and non-conjugated hybrid nanoparticles. For conjugated nanoparticles, the fluorescence response significantly escalated as the dilution factor decreases (or the nanoparticle-conjugate concentration increases). However, the fluorescence response for non-conjugated nanoparticles did not present a meaningful trend. This study verified that Neutravidin molecules were immobilized on the nanoparticle surfaces, and the specific binding between biotin and Neutravidin resulted in the fluorescence increase.

It should be noted that, in the aforementioned experiment, before the acidic solution was added to the wells to dissolve nanoparticle labels, the microplate was scanned in the reader with an excitation wavelength at 355 nm and an emission wavelength at 460 nm. This measurement was employed to directly measure fluorescence emitted from nanoparticle labels. Despite the fact that hybrid nanoparticles were found to be fluorescent using fluorescence spectrometry, it was found that neither conjugated or non-conjugated hybrid nanoparticles exhibited a distinguishable response for any concentration using a microplate reader (probably the weak blue emission of nanoparticles is overwhelmed by autofluorescence from magnetic microbeads or analytes due to UV excitation, or the photomultiplier tube in the microplate was not sensitive enough to detect the blue emission). The emission fluorescence data of hybrid nanoparticles without acidic dissolution is also presented in FIG. 14A. Comparison of fluorescence signals from the two measurement modes (cation release, and direct fluorescence emission of nanoparticles), demonstrates that the cation-release based fluorescence signal transduction is an effective approach to convert weakly fluorescent nanoparticles or nanoparticles with blue emission to sensitive signal transducers which adopt fluorescence emission with longer wavelengths for signal measurement.

To investigate whether the conjugated hybrid nanoparticles in borate buffer are reliable for efficient labeling and signal transduction for several weeks, the cation-release based signal transduction procedure was performed and repeated in a time-course study for three weeks. In each testing, conjugated hybrid nanoparticles diluted 50× were prepared from the same stock nanoparticle solution, and incubated with biotinylated magnetic microbeads; afterwards the nanoparticles captured by the microbeads were dissolved to release zinc ions for further signal transduction. FIG. 14B shows the fluorescence signal level in four tests over a three week time period. This data indicates that the bioconjugated hybrid nanoparticles exhibit a stable fluorescence signal over the testing period. It can therefore be concluded that the conjugated hybrid nanoparticles can be applied to bioassays for at least three weeks after preparation.

Bioconjugated Hybrid Nanoparticles as Signal Transducers in Bioassay

Figure 14:
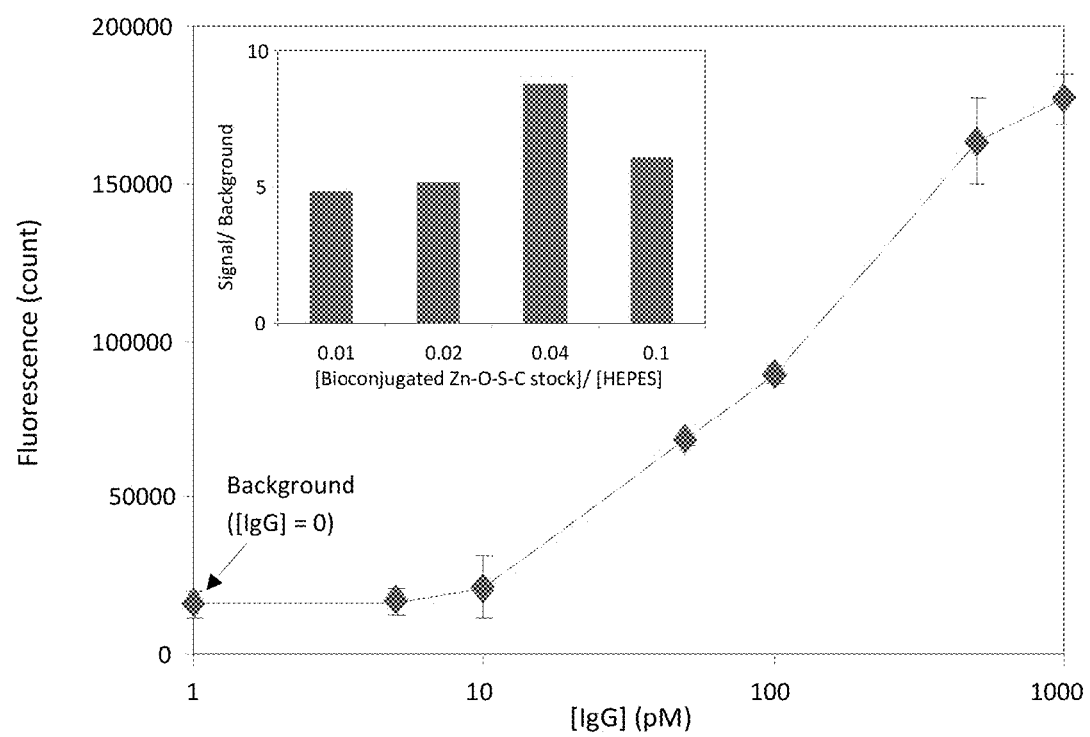
FIG. 14 is a calibration curve for IgG immunoassay using the bioconjugated hybrid nanoparticles for signal transduction (an optimized nanoparticle labeling condition is determined by the signal/noise ratio as shown in the inset).
Figure 15:
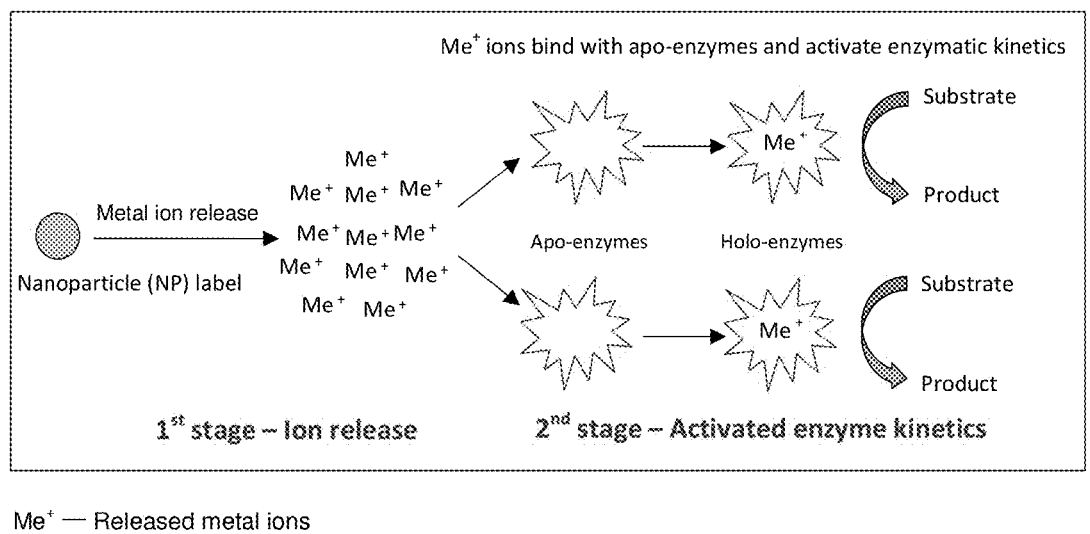
FIG. 15 is a schematic of a disclosed dual signal amplification mechanism—a high number of metal ions were released from nanoparticle labels, and sequentially enzyme kinetics was triggered by the released metal ions as enzyme cofactors (in this study, zinc sulfide nanoparticles and carbonic anhydrase are used as nanolabels and enzyme, respectively).

To apply the bioconjugated hybrid nanoparticles for immunoassay as biolabels or signal transducers, it is desirable to optimize their concentration in the assay because an excess of labeling nanoparticles could increase the background signal thereby deteriorating the sensitivity of the assay. On the other hand, if too few biolabels are used, incomplete labeling of the secondary antibody could potentially occur which might decrease the detection range of the assay. First, magnetic microbeads were used to capture 0 and 100 pM mouse IgG, and then incubated with biotinylated anti-mouse IgG to form immunocomplexes. Second, the immunocomplexes were incubated with 10, 25, 50, and 100 times diluted nanoparticles from the stock solution. Afterwards, the acidic solution (HEPES pH2) was applied to release zinc ions from the bound biolabels. After the pH of the dissolving solution was adjusted to a neutral level, Fluozin-3 was added to each well to react with the liberated zinc ions for subsequent fluorescence measurement. The study was conducted in triplicate. During data processing, 100 pM mouse IgG was used as the signal, while 0 pM IgG was used as the background for the calculation of signal to background ratio. The signal to background ratio is shown in the inset of FIG. 14. It can be seen that the highest signal to background ratio was achieved when the bioconjugated hybrid nanoparticles were diluted 25 times. Thus, the 25× dilution of the bioconjugated hybrid nanoparticles was applied in the assay.

Under the optimized conditions, the assay was performed. FIG. 14 shows the assay calibration curve. On the basis of three times the standard deviation of the background, the detection limit is found to be about 10 pM (n=9). The curve shows the detection range of the IgG assay was of around two orders of magnitude (10 pM 1000 pM). This assay presents effective analytical performance using hybrid nanoparticles as signal transducers. In addition, compared to many reported nanoparticles, these nanoparticles possess the merits of being synthesized with a bioconjugation ready surface, environmental friendliness, low cost, and fast preparation (within around two hours from the setup of experimental tools to the synthesis completion). It is believed that the hybrid nanoparticles demonstrated in this disclosure can be applied to bioassays for various analytes.

This work presents the facile synthesis of hybrid zinc-oxygen-sulfur-carbon nanoparticles in an aqueous solution at low temperature, as well as the immunoassay application of these nanoparticles. The hybrid nanoparticles as biolabels (or signal transducers) are believed to be capable of more diverse biosensing applications in clinical diagnosis, food safety control, environmental monitoring, etc.

In alternative embodiments, it is contemplated that other ions capable of release from nanocrystals could be used as the first messenger. In addition, other signal sources, such as changes in color or different forms of fluorescence, can be used as well.

Embodiments of a kit include reagents for practicing the disclosed method. The kit may optionally include reaction wells, such as reaction plates or Eppendorf tubes and buffers, washes, and other reagents needed to practice the method.

Embodiments of the apparatus include structures for practicing the methods described herein and can include reaction wells, such as reaction plates and Eppendorf tubes, as well as devices for detecting the signal form the substrate.

Embodiments of the system include structures and reagents for practicing the methods described herein.

Example 3

Dual Signal Amplification Techniques for Bioassays

This example provides dual signal amplification techniques for bioassays.

Disclosed herein is a zinc-nanoparticle based dual signal amplification method that can be used for many analytes including, but not limited to, cells, proteins and microRNAs. It is desirable that analytical measurements have high sensitivity or lower detection limits for the analytes of interest. The disclosed dual signal amplification using Zn-nanoparticles is shown herein to have high sensitivity or lower detection limits compared to the conventional enzyme-linked immunosorbent assay (ELISA) technology. In particular, ELISA technology utilizes biological enzymes as labels for single stage signal amplification. The biological enzymes fabricated using biological methods are often expensive and need to be immobilized on antibody for assaying. The immobilization is tedious and also causes the reaction activity loss of enzymes. In addition, the biological enzymes have a limited on-shelf time. In contrast, the presently disclosed dual amplification method utilizes Zn-nanoparticles as labels. As shown herein, Zn-nanoparticles are easily made by one of ordinary skill in the art and not associated with any significant cost. Further, although enzymes are used in the disclosed dual amplification method, enzyme immobilization is not needed. Moreover, the enzyme (carbonic anhydrase) is inexpensive and deactivated and thus, can be stored for long periods of time.

Chemicals and Apparatus

Carbonic anhydrase (CA) from bovine erythrocytes, $Zn(NO_3)_2$, $ZnCl_2$, dipicolinic acid (DPA), trace metal grade 12 M HCl, trace metal grade NaOH, thioglycolic acid (TGA), and thioacetamide were from Sigma Aldrich (St. Louis, Mo.). N-(2-hydroxyethyl)piperazine-N'-2-ethanesulfonic acid (HEPES), 2-amino-2-hydroxymethyl-propane-1,3-diol (Tris), 2-(N-morpholino)ethanesulfonic acid (MES), glacial acetic acid, ethanol, fluorescein, fluorescein diacetate (FDA), ethylenediaminetetraacetic acid (EDTA), dimethyl sulfoxide (DMSO), fluorescein-d-β-D-galactopyranoside (FDG), $CdCl_2 CaCl_2$, KCl, $KNO_3$, $PbCl_2$, $NaH_2PO_4$, $Na_2HPO_4$, NaCl, $NaN_3$, $MgCl_2 \cdot 6H_2O$, and Tween 20, were from Fisher Scientific (Pittsburgh, Pa.). 1-ethyl-3-(3-dimethylamino-propyl) carbodiimide (EDC), N-hydroxysuccinimide ester (NHS), NeutrAvidin, Magnabind goat anti-mouse IgG, whole molecule mouse IgG, biotinylated goat anti-mouse IgG F(ab')2, and 20× borate buffer were from Pierce (Rockford, Ill.). Bovine serum albumin (BSA) free of IgG and protease was from Jackson ImmunoResearch (West Grove, Pa.). Streptavidin conjugated beta-galactosidase was from Invitrogen (Carlsbad, Calif.). Human cardiac troponin I (cTnI), monoclonal anti-human cTnI (clone 625), and biotinylated monoclonal anti-human cTnI (clone 284) were from Meridian Life Science (Saco, Me.). cTnI depleted human serum was purchased from Fitzgerald Industries International (Acton, Mass.). Carboxyl terminated magnetic beads with 4.5 um diameter were from Spherotech (Lake Forest, Ill.).

HEPES buffer was prepared using 25 mM HEPES and 50 mM NaCl with pH 7.4 (when needed, the pH of HEPES buffer was adjusted using HCl or Tris base). PBS-R buffer consisted of 44 mM $NaH_2PO_4$, 56 mM $Na_2HPO_4$, 100 mM NaCl, 1% BSA, 0.5% Tween 20 and 3 mM $NaN_3$ in DI water with a pH of 7.4. PBS-D buffer was comprised of 44 mM $NaH_2PO_4$, 56 mM $Na_2HPO_4$, 100 mM NaCl, 5 mM $MgCl_2 \cdot 6H_2O$ and 3 mM $NaN_3$ in DI water with pH 7.4. MES buffer was made of 0.1 M MES and 0.5 M NaCl in DI water with pH 6.0. 24.2 g Tris base, 7.32 g EDTA, and 5.7 mL of Glacial acetic acid were mixed with 100 mL DI water to prepare 50×TAE. 2 mM FDG solutions were prepared before use by diluting 394 µL of 1 mg/mL FDG (dissolved in a 50:50 mixture of ethanol and DMSO) into 2.606 mL of PBS-D buffer.

5 mg carboxyl terminated magnetic beads were mixed with 4 mg NHS and 5 mg EDC in 1 mL of MES buffer for 30 min. The magnetic beads were then washed and incubated with 0.5 mg monoclonal anti-human cardiac troponin I (clone 625) for 2 hours. After the incubation, the beads were washed and re-suspended in 5 mL of PBS-R as stock and stored at 4° C.

A Perkin Elmer (Waltham, Mass.) Victor 3 microplate reader was used for fluorescence measurement of 96-well microplates from Fisher Scientific. A bandpass excitation filter centered at 485 nm (bandwidth=14 nm) and a bandpass emission filter at 520 nm (bandwidth=25 nm) were used for fluorescence measurement.

Zinc Ion Detection Using Carbonic Anhydrase

Preparation of apo-CA was performed using DPA as a chelation agent for the removal of zinc ions from the holo-CA. First, 500 µL of a 165 µM stock CA solution (prepared in 50:50 glycerol:HEPES) was mixed with 3.5 mL of DPA-Tris (50 mM DPA, 100 mM Tris, pH 7.4) for one hour on a rotation rocker. The DPA-Tris-CA solution was then added to a YM-10 centrifugal filtration unit (Pierce) and was centrifuged at 4400 rpm in an Eppendorf (Hamburg, Germany) 5702R centrifuge for 20 minutes. After the initial centrifugation, the retained CA was washed three times with 3.5 mL of DPA-Tris using the same centrifugation procedure. To remove all unreacted chemicals, the YM-10 filtration unit and the retained apo-CA was washed several times using 3.5 mL of DI water and centrifugation at 4400 rpm for 20 minutes. Finally, the apo-CA was reconstituted to 500 µL with HEPES at pH 7.4 and stored at 4° C.

For the detection of zinc ions, 50 µL of 0-10 µM $ZnCl_2$ solutions in HEPES were added to the wells of a microplate in triplicate. Next, 165 µM holo-CA was diluted to 2 uM and the recovered apo-CA was diluted the same number of times as the holo-CA. 50 µL of both diluted apo-CA and holo-CA were added to the wells and incubated with the zinc solutions for three minutes on a vortex. Finally, 50 µL of 10 µM FDA were added to all of the wells and the conversion of FDA to fluorescein was allowed to proceed for 15 minutes. The fluorescence responses of apo-CA and holo-CA to different zinc-ion concentrations were measured.

Synthesis and Bioconjugation of ZnS Nanoparticles

ZnS nanoparticles were prepared and bioconjugated. Briefly, 75 mg $Zn(NO_3)_2$ dissolved in 50 mL of DI water was mixed with 100 uL of TGA in a glass flask (washed using TAE buffer and DI to minimize divalent metal ion contaminants), and 2 M NaOH was added to the mixed solution until a pH of 11.5 was attained. The pH adjusted solution was deoxygenated using nitrogen for 15 min, and 12 mg thioacetamide were added to the solution for overnight growth at 80° C. The prepared ZnS nanoparticles were concentrated 10 times and washed using 1× borate buffer and centrifugation. For bioconjugation, 500 uL of the concentrated ZnS nanoparticles were mixed with 100 uL of 20 mM EDC and 20 uL of 200 mM NHS at room temperature for 15 minutes. After thoroughly washing, the nanoparticles were incubated with 0.5 mL of 0.25 uM NeutrAvidin at room temperature for 2 hours. The conjugated ZnS nanoparticles were washed and resuspended in 500 µL of 1× borate buffer. The conjugated nanoparticle labels were stored at 4° C. and used within two weeks.

Immunoassay Using the Dual Signal Amplification

In the model immunoassay on mouse IgG, HEPES at pH 7.4 with 0.5% BSA and 0.05% Tween 20 was used for reagent preparation, biochemical reactions, and bead washes. Otherwise, the composition of different reaction or buffer solutions will be specifically stated. The mouse IgG assay was performed as follows. First, 2.5 µL of Magnabind beads coated with goat anti-mouse IgG were added to the wells of a microplate and washed three times. Second, 50 µL of serially diluted mouse IgG (0-50 pM) were added to the wells, and vortexed for 30 minutes. After antigenic capture, the beads were washed. Third, 50 µL of 30 nM biotinylated anti-mouse IgG were added to the wells and incubated for 30 minutes, and afterwards the formed immunocomplexes were washed several times. Fourth, the immunocomplexes in each well were blocked using HEPES at pH 7.4 with 5% BSA for 30 minutes. Afterwards, Neutravidin conjugated ZnS nanoparticles were diluted 250 times and 50 µL of the ZnS nanoparticle solution was added to each well and incubated for 5 minutes to bind with biotinylated secondary antibodies. After incubation with ZnS nanoparticles, the beads in the wells were washed. Fifth, 50 µL of HEPES at pH 2 were added to the wells and incubated for several minutes on a vortex to release zinc ions. After releasing the ions, the pH was adjusted to a more neutral level using the addition of 100 µL of HEPES at pH 8. Sixth, 25 µL of 4 µM apo-CA were added to the wells of the microplate and incubated for several minutes for enzymatic activation by the zinc ions. Finally, 25 µL of 20 µM FDA were added to each well and the plate was incubated for 15 minutes on a vortex before fluorescence quantification in the wells.

The real sample assay on human cTnI adopted similar steps, but with a few different assay parameters. In the assay procedures, 2.5 uL of the beads coated with monoclonal anti-human cTnI and 50 nM biotinylated monoclonal anti-human cTnI were used. Both the model assay on mouse IgG and the real sample assay on cTnI were performed in triplicate. The average and the standard deviation of signals for each sample are presented in the data figures.

Sensitivity and Specificity of Carbonic Anhydrase (CA) to Zinc Ions

Figure 16:
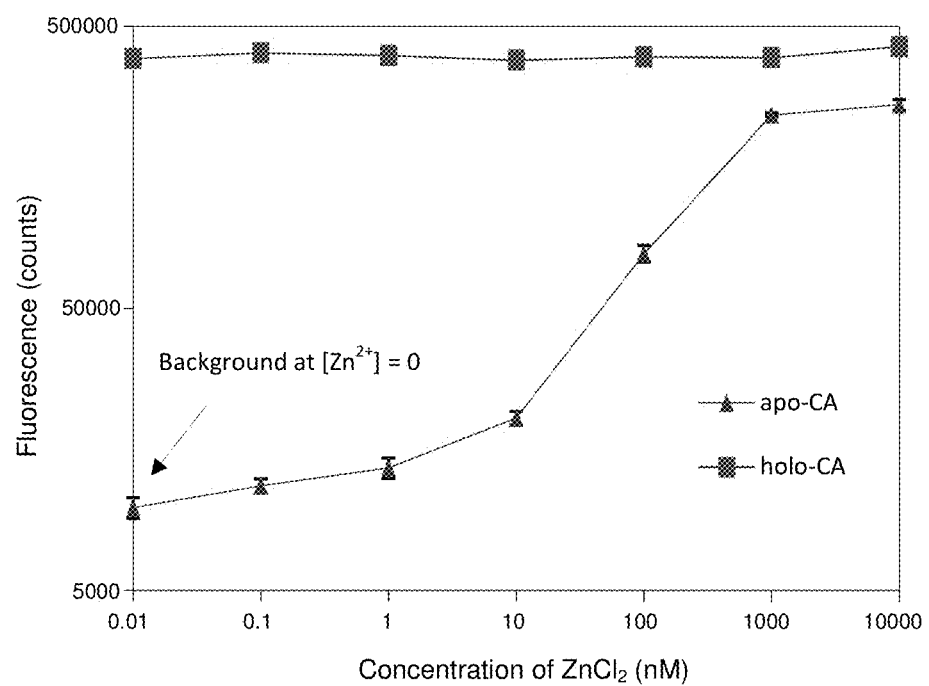
FIG. 16 illustrates zinc ion dependence of holo-carbonic anhydrase (holo-CA) and apo-carbonic anhydrase (apo-CA) on the reaction with substrate fluorescein diacetate (FDA).
Figure 17:
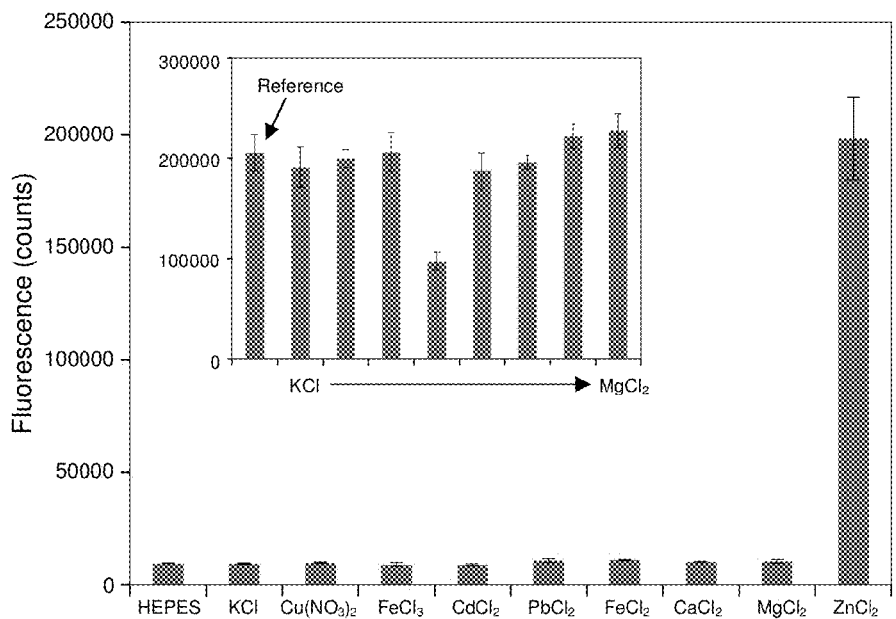
FIG. 17 shows the fluorescence response for the enzymatic reaction of 2 μM apo-CA and 10 μM FDA with two different $ZnCl_2$ concentratations.

In some enzyme-substrate systems, metal ions are required as cofactors to activate the enzyme for the conversion of substrate to product. The role of metal ions in enzyme kinetics could be one of the following—the metal ions are involved in the catalytic processes; or they assist in substrate binding; or they have an action on the conformational properties such as the tertiary or quaternary structure of the enzyme. In this Example, it was found that CA-FDA was an enzyme-substrate system where zinc ions were required as cofactors of CA to trigger enzyme kinetics. Moreover, the enzymatic activity of CA converting FDA to fluorescein was very sensitive to the concentration of zinc ions. In the study, apo-CA was prepared using DPA to remove zinc ions bound to holo-CA. 165 µM holo-CA was diluted to 2 uM, and the apo-CA recovered from the DPA treatment of holo-CA was diluted the same number of times as the holo-CA. The enzymatic activities of both diluted apo-CA and holo-CA were compared. FIG. 16 presents the fluorescence responses of apo-CA and holo-CA (in the presence of 10 uM substrate FDA) to different concentrations of zinc ions. For holo-CA (2 uM), the activity was not affected by the addition of $ZnCl_2$, seemingly because the active sites are saturated with zinc ions before the addition. However, the activity of apo-CA is clearly dependent on the concentration of zinc ions over a wide range (0.1 nM to 1 uM), as shown in FIG. 16. Thus, apo-CA can be used as an indicator to sensitively quantify zinc-ion concentrations. By comparing the fluorescence signal levels at both low and high zinc-ion concentration ends of the apo-CA activity curve, the activity of apo-CA (without zinc ions) was only around 3% of that when apo-CA was saturated with zinc ions. It can be determined that DPA is efficient at removing zinc ions from holo-CA. Moreover, at the high zinc-ion concentration end of FIG. 16, the activity of apo-CA saturated with zinc ions was only around 70% compared to that of holo-CA. This could be due to a loss of apo-CA during the treatment with YM-10 filters. Note that in this study, all enzyme reactions were developed for 15 minutes to generate a sufficient signal magnitude before quantification using the microplate reader. As shown in FIG. 17, the enzymatic reaction of 2 uM apo-CA with 10 µM FDA and 1 µM $ZnCl_2$ remained linear after a 15 minute reaction time.

Figure 18:
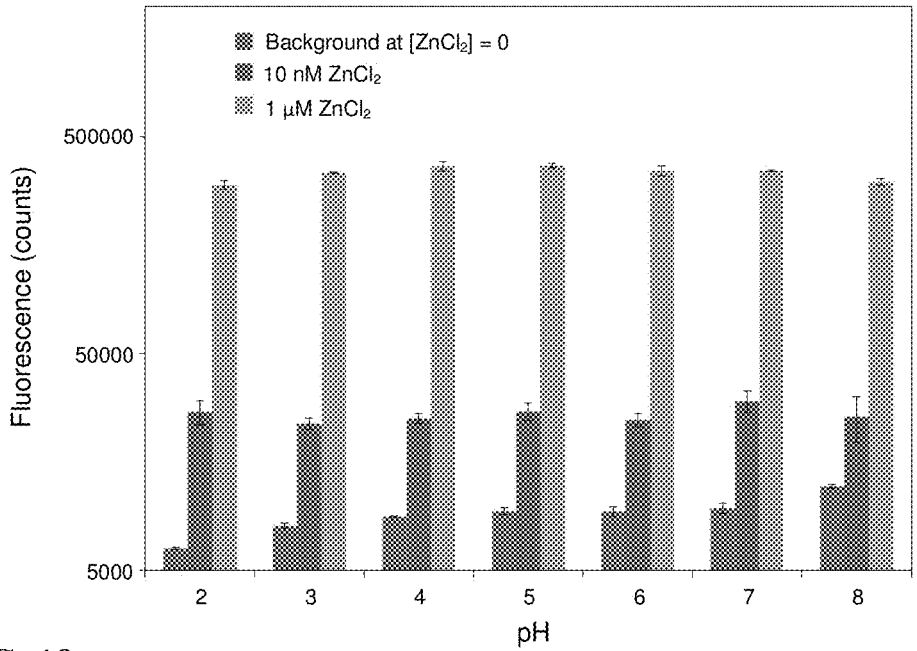
FIG. 18 shows the specificity of apo-CA to zinc ions in converting FDA to fluorescein (insert: interference of some metal ions on the reaction of apo-CA with both $ZnCl_2$ and FDA, which is marked as reference).

To investigate the specificity of apo-CA to zinc ions, 2 uM apo-CA was mixed with 1 uM KCl, $Cu(NO_3)_2$, $FeCl_3$, $CdCl_2$, $PbCl_2$, $FeCl_2$, $CaCl_2$, $MgCl_2$ and $ZnCl_2$ spiked in HEPES buffer, respectively. 10 uM FDA was then added to develop fluorescence signals. FIG. 18 demonstrates the signal response of each kind of metal ion. In this figure, the reaction signals for apo-CA with $K^+$, $Cu^{2+}$, $Fe^{3+}$, $Cd^{2+}$, $Pb^{2+}$, $Fe^{2+}$, $Ca^{2+}$, and $Mg^{2+}$ could not be distinguished from the background signal of HEPES buffer. However, the reaction of apo-CA with $ZnCl_2$ resulted in high fluorescence intensity. Therefore, apo-CA was selectively activated by zinc ions. Another concern was that the presence of non-zinc metal ions could interfere with the ability of apo-CA to react with zinc ions. Thus, an investigation of the potential interference caused by the presence of other metal ions was performed. In this study, 1 µM KCl, $Cu(NO_3)_2$, $FeCl_3$, $CdCl_2$, $PbCl_2$, $FeCl_2$, $CaCl_2$ and $MgCl_2$ were added to 2 uM apo-CA mixed with 1 µM $ZnCl_2$. Sequentially, 10 uM FDA was added to generate fluorescence signals. The inset of FIG. 18 demonstrates the results of the interference study. Most of the metal ions did not significantly interfere with the reaction between apo-CA and zinc ions, but $Cd^{2+}$ clearly quenched the reaction. Thus, in the assay procedures, $Cd^{2+}$ contamination should be avoided.

Figure 19:
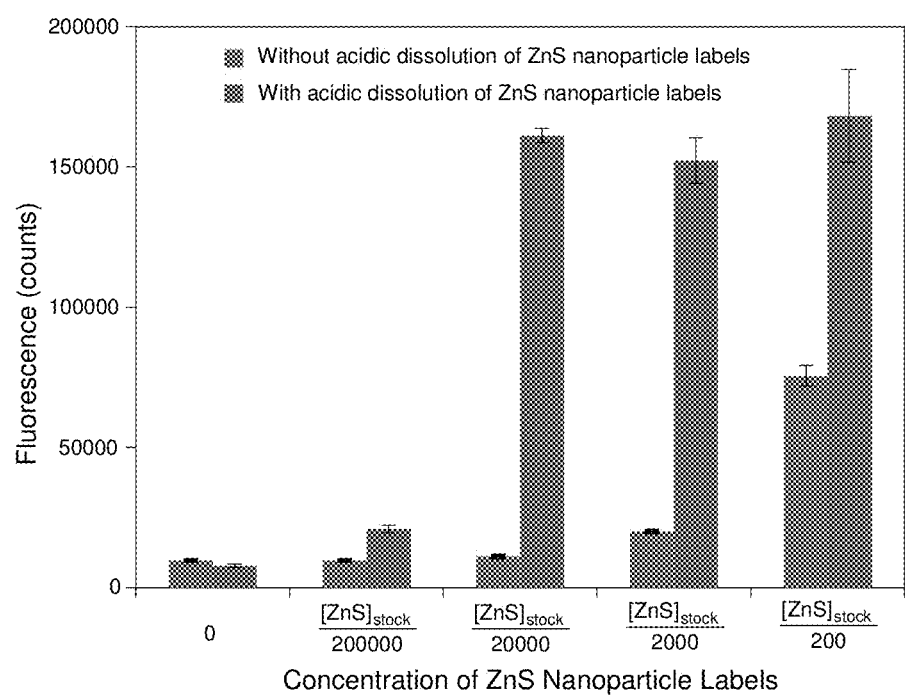
FIG. 19 illustrates the effects of pH on the reaction of apo-CA with $ZnCl_2$ and FDA (all chemicals are prepared in solutions with the same pH).

Through this study, it was demonstrated that the activity of CA in its apo-form was sensitive and specific to zinc ions. These properties of apo-CA ensured that assay reagents were easy to prepare without tedious purification steps to remove common ions such as $K^+$, $Ca^{2+}$ and $Mg^{2+}$.

pH Effects on the Reaction of Carbonic Anhydrase with Zinc Ions and Fluorescein Diacetate Enzyme activity usually is sensitive to the pH of the reaction environment. FIG. 19 shows the effects of pH on the reaction of apo-CA with $ZnCl_2$ and FDA, where $ZnCl_2$, apo-CA, and FDA were prepared in HEPES with the same pH before mixing. It can be seen that the enzyme activity was highly pH-dependent. When the pH of the reaction solution was 6, there was almost no measureable response or distinguishable difference between 0 µM $ZnCl_2$ (background) and 1 µM $ZnCl_2$ (signal). For pH levels at 7 and 8, the activity of CA is enhanced (at pH 7 both the background and the signal occur at relatively lower levels). There was a significant increase in both background and signal when the reaction was carried out at pH 9. It is believed that spontaneous hydrolysis of FDA to fluorescein occurs in alkaline solutions. A high background can deteriorate detection limits of bioassays, and thus a pH level between 7 and 8 was determined to be optimal for the enzymatic reaction.

On the other hand, in the assay procedures for mouse IgG or human cTnI, HEPES at pH 2 was used to dissolve nanoparticle labels. After acidic dissolution, the pH of the dissolving solution depends on the number of ZnS nanoparticle labels in each well. For instance, if a low number of ZnS nanoparticle labels are in the wells, only a small number of protons will react and the pH of the dissolving solution still could be close to 2. If most of the protons are consumed by ZnS nanoparticles, the pH of the dissolving solution could shift towards 7. It is therefore desirable that a neutralizing and buffering solution be applied to mix with the dissolving solution in each well, and thus adjust the pH of the solution to 7~8 for further addition of CA and FDA.

In the studies, it was found that a volume ratio of 1:2 between HEPES at pH 2 and HEPES at pH 8 can bring the pH of the mixture to around 7.4. Even though most of the protons in HEPES at pH 2 could be consumed by reacting with ZnS nanoparticles, further mixing of the dissolving solution with HEPES at pH 8 would still adjust the pH of the dissolving solution close to 8. Thus, in the assay procedures, after acidic dissolution of ZnS nanoparticle labels, a volume of HEPES at pH 8 twice that of HEPES at pH 2 was applied to mix with the dissolving solution in each well.

Figure 20:
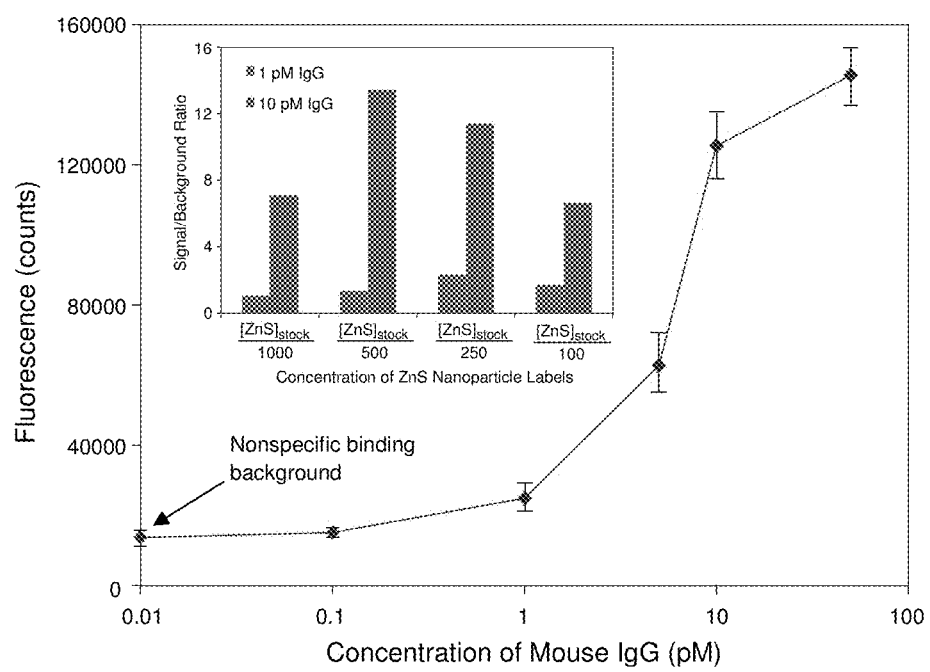
FIG. 20 illustrates the effects of pH on the reaction of apo-CA with both $ZnCl_2$ and FDA ($ZnCl_2$ solutions were prepared in HEPES solutions with different pH levels (2~8) and mixed with HEPES (pH 8) at a 1:2 volume ratio before the addition of apo-CA and FDA prepared in HEPES at pH 7.4).

A study was conducted to test the neutralizing and buffering capacity of HEPES at pH 8. In the study, $ZnCl_2$ solutions were prepared in HEPES at pH 2, 3, 4, 5, 6, 7, and 8. Then, 50 µL of $ZnCl_2$ solutions at each pH level were mixed with 100 uL of HEPES at pH 8. Sequentially, the mixture was added with 25 μL of 4 μM apo-CA followed by 25 μL of 20 μM FDA (prepared in HEPES at pH 7.4). After allowing the enzymatic reaction to proceed for 15 minutes, the fluorescence intensities were quantified. FIG. 20 shows that there is a very similar response for $ZnCl_2$ solutions prepared in HEPES at pH 2~8. The neutralizing and buffering capability of HEPES at pH 8 is sufficient to result in very similar fluorescent responses for different pH level solutions with fixed zinc-ion concentrations.

Coupling ZnS Nanoparticle Labels with Carbonic Anhydrase

Figure 21:
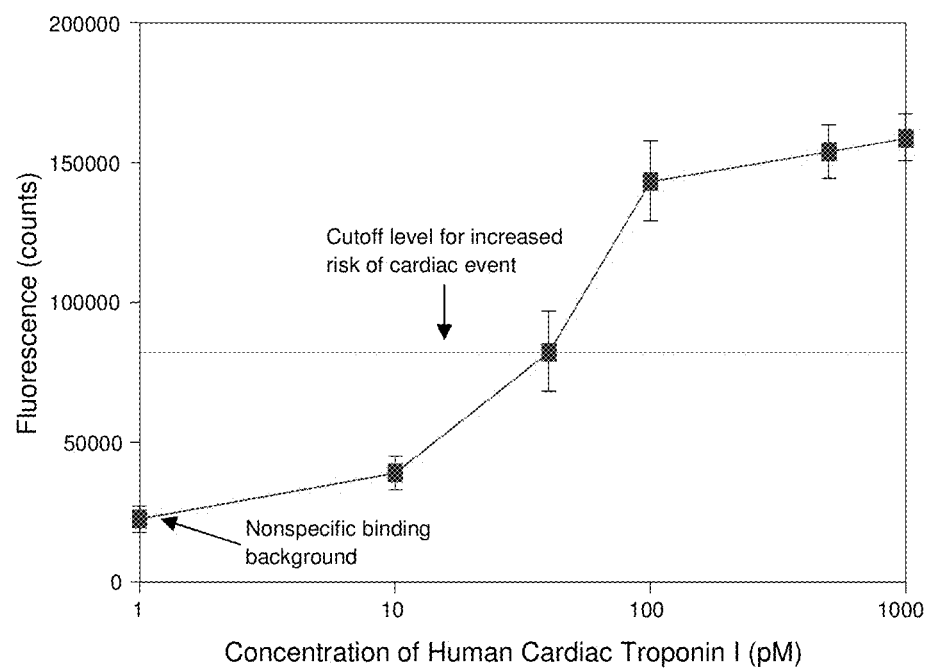
FIG. 21 is an SEM image of the prepared ZnS nanoparticles with a ~50 nm diameter (the bar in the image is in 500 nm scale).

The synthesis, characterization and bioconjugation procedures for ZnS nanoparticles have been presented previously herein. A hydrothermal reaction using zinc nitrate, thioacetamide, and thioglycolic acid in an alkaline condition was used for the synthesis of ZnS nanoparticles. Under the appropriate synthesis conditions, ZnS nanoparticles were spherical with an average diameter of 50 nm, as shown in FIG. 21. Bioconjugation of the ZnS nanoparticles with Neutravidin was performed using EDC/NHS crosslinking in borate buffer. The stock concentration of bioconjugated ZnS nanoparticles was estimated to be in the range of 5-50 nM using the interpolation approach with each nanoparticle releasing millions of zinc ions.

Figure 22:
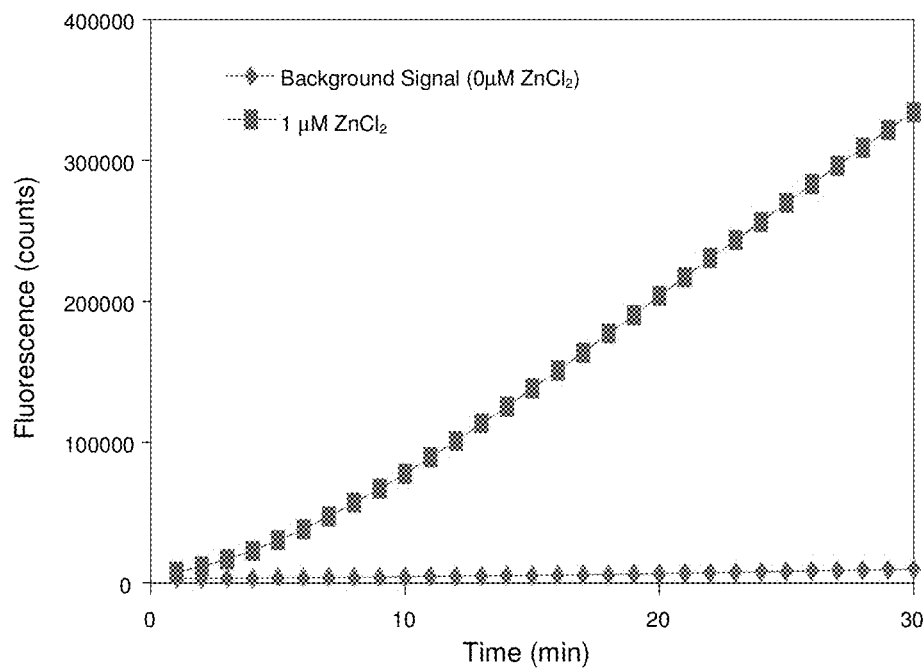
FIG. 22 illustrates the effect of acidic dissolution of ZnS nanoparticle labels on signal transduction.

In this work, zinc ions released from ZnS nanoparticle labels trigger enzyme kinetics. However, it is still possible that ZnS nanoparticle labels themselves could activate the enzymatic activity of apo-CA. Moreover, the difference between the enzyme activity triggered by ZnS nanoparticles and the released zinc ions was unknown. A study was performed to investigate this question. In the study, stock ZnS nanoparticle labels were diluted to different concentrations in either HEPES at pH 2 or HEPES at pH 7.4. 50 μL of each dilution (including ZnS nanoparticle free buffer used as a negative control) under the selected pH condition was added to the wells of a microplate in triplicate. 100 uL of HEPES at pH 8 was added to each well for further pH adjustment. 25 μL of 4 μM apo-CA and 25 μL of 20 μM FDA prepared in HEPES at pH 7.4 were then added to the wells and incubated for fluorescent product generation. The results from this study are shown in FIG. 22. They demonstrate that although enzyme activity can be triggered by ZnS nanoparticle labels present at relatively high concentrations, acidic dissolution of the ZnS nanoparticle labels achieves a much increased enzymatic activity of apo-CA. Moreover, this study also proves that ZnS nanoparticle labels can be coupled with the enzyme-substrate system for signal transduction after acidic dissolution and pH adjustment. Note that under acidic dissolution conditions, the fluorescence responses for 200×, 2000× and 20000× diluted stock ZnS nanoparticle labels occur at similar magnitudes. It is believed that the reactions for these dilutions are limited by the concentration of enzyme, and thus the fluorescence signals are present at similar levels. From FIG. 22, it also can be seen that 200000× diluted stock ZnS nanoparticle labels, which may correspond to ZnS nanoparticles in the concentration range from 25 fM to 0.25 pM (the stock ZnS nanoparticle=5-50 nM), still can be detectable under the acidic dissolution condition when compared to its background. It should be noted that under the identical optical excitation and emission conditions of microplate reader, the minimum detection concentration of the conventional organic fluorophore such as fluorescein (prepared in ethanol and diluted in HEPES buffer) was identified to be around 10 pM. The capability of the instrument to detect a lower concentration of ZnS nanoparticles is believed to be attributed to the dual signal amplification from ZnS nanoparticles.

Immunoassay for Mouse IgG Using Dual Signal Amplification

Figure 23:
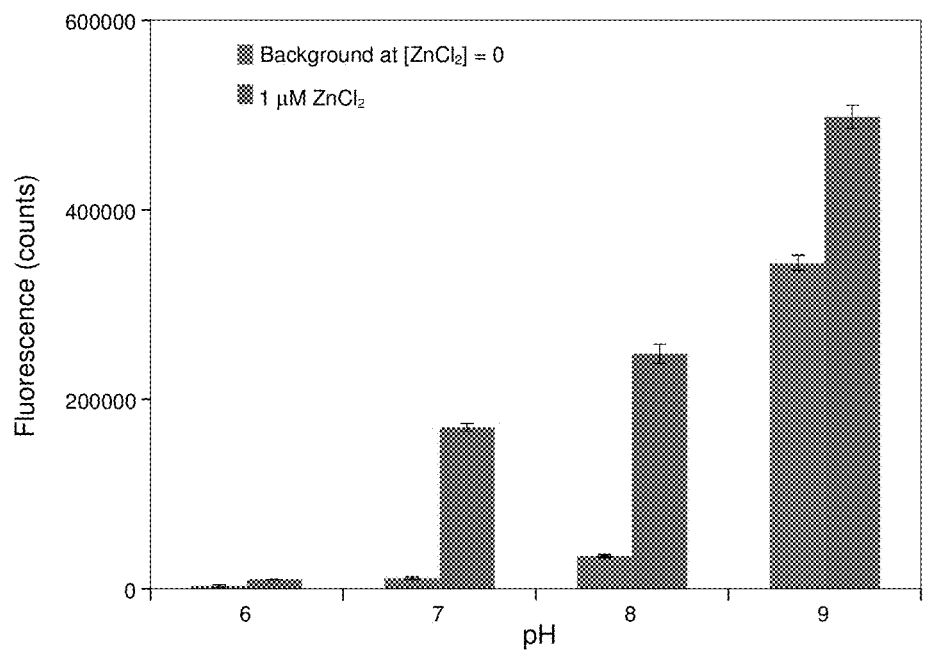
FIG. 23 is a calibration curve of mouse IgG assay using the dual signal amplification (insert: optimization of ZnS nanoparticle concentration to achieve a reasonable signal/background ratio).

The mouse IgG based model assay is an efficient and low-cost tool to study various signal transduction mechanisms, and thus it was chosen to investigate the proposed dual signal amplification strategy. To achieve a high resolution for the assay, it is desirable to determine the optimum ZnS labeling concentration (too many or too few ZnS nanoparticle labels could cause high background or insufficient labeling). To carry out the optimization study, 2.5 μL of goat-anti mouse IgG magnetic beads were incubated with 50 uL of mouse IgG at 0 (background), 1 and 10 pM concentrations. After antigenic capture, the beads were washed and 50 uL of 30 nM biotinylated detection antibody were added to each well to form sandwich immunocomplexes. Afterwards, different concentrations of bioconjugated ZnS nanoparticles were incubated with immunocomplexes for labeling. After unbound ZnS nanoparticle labels were washed out, zinc ions from the bound ZnS nanoparticle labels were released to trigger the enzyme-substrate system. The inset data in FIG. 23 show the signal to background ratio for both 1 pM and 10 pM mouse IgG. Compared to 500× dilution, 250× dilution of the stock ZnS nanoparticles caused a lower signal/background ratio at 10 pM mouse IgG, but a higher signal/background ratio at 1 pM mouse IgG. Considering a higher signal/background ratio towards a lower concentration of analytes is desirable to achieve a lower detection limit, 250× dilution condition was selected for further assay. Adopting the optimized ZnS nanoparticle labeling condition, mouse IgG was assayed and the calibration curve is shown in FIG. 23. On the basis of three times the deviation of the background, the detection limit of this model assay is estimated to be around 0.5 pM (n=9). The assay presents a wide detection range (0.5 to 50 pM).

Figure 24:
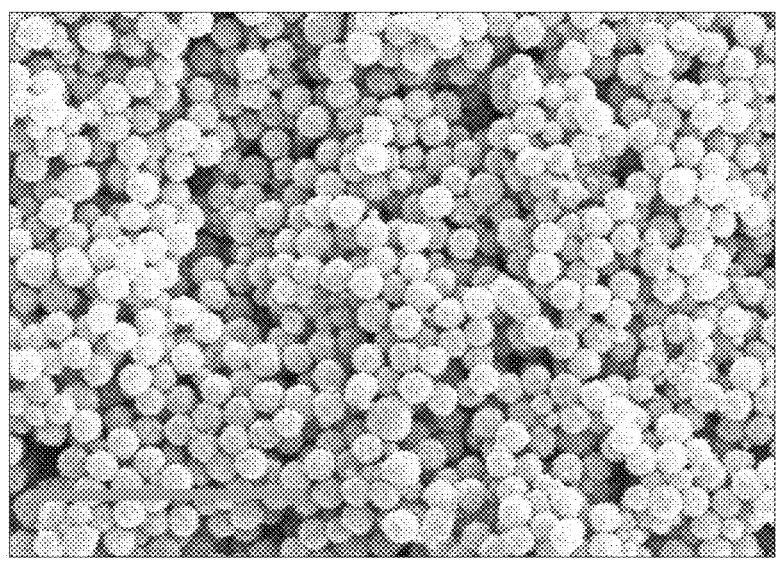
FIG. 24 illustrates the calibration of the streptavidin-beta-galactosidase based immunoassay on mouse IgG (the detection limit is around 5 pM on the basis of the three times of standard deviation of the background).

For comparison, a conventional enzyme assay on mouse IgG was performed. The enzyme-based assay adopted the same protocol as the ZnS nanoparticle based assay, but in the last assay step streptavidin conjugated enzyme was applied for signal transduction. Instead of CA, beta-galactosidase was used as the enzyme for converting FDG (prepared in PBS-D) to fluorescein for signal amplification. Beta-galactosidase was chosen because it is more sensitive than CA (the Michaelis-Menten constant $K_m$ of beta-galactosidase was measured to be at around 7 mM, ten times lower than that of CA). FIG. 24 shows the calibration curve of the enzyme-based assay, and the detection limit of this assay is around 5 pM. From the comparison of these assay results, it can be seen that the dual stage signal amplification is capable of detecting mouse IgG with a higher resolution or a lower detection limit.

Real Sample Assay on Human Cardiac Troponin I

To demonstrate a potential clinical application of the dual signal amplification, a real sample assay on human cTnI, which adopted this technique, was developed. Human cTnI is a small protein (around 24 kDa) that is considered to be one of the most important biomarkers for the diagnosis of myocardial infarction (MI). Annually, 785,000 Americans will suffer a new MI and 470,000 will experience a recurrent heart attack, while an additional 195,000 are estimated to undergo an unreported silent MI. Approximately 16% of individuals experiencing a first MI die acutely and of the 84% of patients that do survive their MI, an estimated 15 years of life is lost. cTnI is highly specific for cardiac muscle damage, and its concentration in blood increases dramatically from a normal level (below 1.0 ng/mL) after the onset of a myocardial infarction. In some works, the cut-off cTnI concentration for clinical diagnosis has been reported to be 1 ng/mL (or around 40 pM) in human serum.

Figure 25:
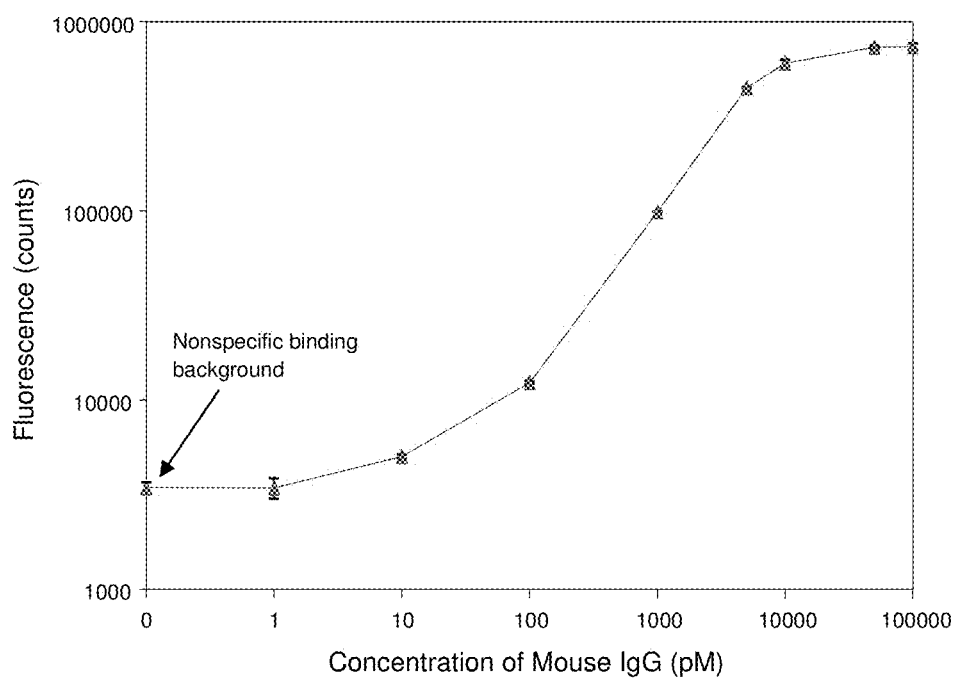
FIG. 25 Calibration curve for the assay of human cTnI in human serum using the dual signal amplification.
Figure 26:
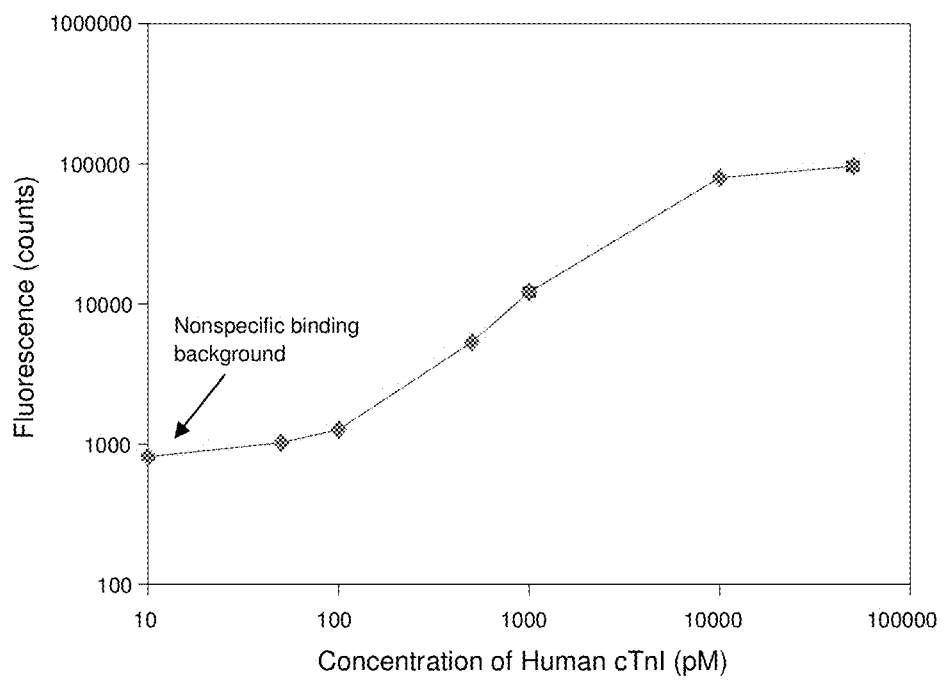
FIG. 26 provides calibration curves of the streptavidin-beta-galactosidase based immunoassay on cTnI (the detection limit is around 50 pM on the basis of the three times of standard deviation of the background).

In the development of the real sample assay, the optimum ZnS labeling concentration was studied in the same manner as that for mouse IgG. By comparing the signal (of 50 pM or 500 pM cTnI in human serum) to background ratio at different dilutions of ZnS nanoparticles, it was found that diluting 250× was the best labeling concentration for the cTnI assay. With this optimized labeling condition, the assay on cTnI was performed and the calibration curve for the assay is shown in FIG. 25. The cutoff level (40 pM) of cTnI is within the detection range. Similar to the mouse IgG assay, a beta-galactosidase based assay on cTnI was conducted as a reference. The calibration curve of the enzyme assay on cTnI is shown in FIG. 26, and the detection limit is around 50 pM. It is clear that the dual signal amplification can detect the critical level of cTnI in a real sample matrix.

In this work, the proof-of-concept of a dual signal amplification technique using ion release from nanolabels and ion-activated enzyme kinetics was demonstrated. A model bioassay on mouse IgG adopting this technique presents a detection limit around 0.5 pM and a detection range over two orders of magnitude. This technique was also successfully applied to the detection of a biomarker (cTnI) in human serum samples demonstrating a clinical diagnosis application. The developed technique has the following merits. First, it achieves a high detection resolution. Second, it is easy to operate and low cost (simple preparation of ZnS nanoparticles and apo-CA, and no enzyme immobilization). Third, it employs carbonic anhydrase, an enzyme which is insensitive to calcium or other common ions, and therefore avoids the laborious work related to buffer or reagent purification in bioassays. Fourth, compared to other conventional signal transduction mechanism using CdSe or PbS nanoparticles, it adopts less toxic ZnS nanoparticles and thus is more environmentally friendly.

The effect of some assay parameters such as the size of nanoparticles on the detection resolution of the assay adopting this technique may be adjusted to optimize the methods. More sensitive and faster enzyme-substrate systems may be employed for metal ion detection and applied for bioassays to enhance assay sensitivity and response time. The dual signal amplification technique may be used in various bioassays for clinical diagnosis, food safety control, biology study, security, biological warfare detection, and others applications. Other metal-ion nanoparticles may be used in addition to zinc-based nanoparticles, such as CuS nanoparticles, could potentially be applied in the dual signal amplification approach, as long as appropriate enzyme-substrate systems (or DNAzyme-substrate systems) that are sensitive to the released metal ions are used.

Example 4

Use of Zinc-Based Nanolabels or Beta-Galactosidase Labels for miRNA Detection

This example demonstrates the successful use of zinc-based nanolabels or beta-galactosidase labels for miRNA detection.

MicroRNAs (miRNAs) are relatively short (a few nanometers in length with 17-25 nucleotides), post-transcriptional regulators that bind to target complimentary sequences of messenger RNA (mRNA). MiRNAs were identified as key gene regulators with conserved biological functions. Currently it is believed that over 1,000 miRNAs could be encoded by the human genome and target up to 60% of the entire genome. Altered miRNA expression levels have been implicated as indicators of different disease states such as cancer, cardiac disease, and diabetes. Progress in this field of study has also revealed that the expression profiles of miRNAs found in serum, plasma, urine or other bodily fluids can be used to predict physiological or pathological conditions. Therefore, developing miRNA detection methods is a meaningful area of investigation with the potential to significantly improve clinical diagnostic procedures.

Although conventional molecule biology based methods such as miRNA cloning, northern blotting and quantitative-real time polymerase chain reaction (qRT-PCR) are the choices for miRNA detection, many nanobiosensing based miRNA detection approaches have been reported towards establishing novel and more functional detection protocols. Herein, a new miRNA detection method, which combines magnetic separation, polyadenylation, and signal amplification, is presented. FIG. 27 schematically demonstrates the procedures used for miRNA detection. In this procedure, locked nucleic acid (LNA) probes complimentary to miRNA-21 are conjugated to a paramagnetic bead and hybridization captures miRNA-21 in solution. After capture, poly(A) polymerase catalyzes a polyadenylation reaction on the 3'-OH end of the bound miRNA-21. The generation of poly(A) tails is followed by biotinylated poly(T)$_{30}$ hybridization with the poly(A) tail which specifically permits NeutrAvidin-conjugated ZnS nanoparticle labeling or streptavidin-conjugated beta-galactosidase labeling through biotin-Neutravidin chemistry. For signal transduction of the assay, there are two alternative approaches: (1) zinc ions from the ZnS nanoparticles are released to bind with zinc-ion depleted carbonic anhydrase and activate the enzymatic kinetics of carbonic anhydrase which converts fluorescein diacetate to fluorescein, or (2) beta-galactosidase (enzyme) converts fluorescein-di-beta-D-galactopyranoside (FDG) to fluorescein. The developed method has several advantages. First, it uses magnetic separation for bead washing and buffer exchange, and thus simplifies reagent handling. It also offers the potential for spatial multiplexing or high throughput testing of miRNA. Second, instead of using complementary DNA as capture probe for miRNA, LNA is adopted to ensure the assay specificity because LNA has been proved to be able to discriminate between oligonucleotides with a single base pair mismatch. Third, both zinc-based nanolabels and beta-galactosidase labels are sensitive transducers with low cost and environmental benignity. As shown in this work, the assay using zinc-based nanolabels or beta-galactosidase labels for miRNA detection is sensitive and achieves a detection limit at picomolar level (several picograms of miRNA).

Methods

MiRNA-21 (5'-rUrArGrCrUrUrArUrCrArGrArCrUr-GrArUrGrUrUrGrA-3'; SEQ ID NO: 1), amine group terminated LNA probes complimentary to miRNA-21 (5'-T+CAA+CA+T+CAGTCTGATA/iSp18//3AmMO/-3'; SEQ ID NO: 2), yeast poly(A) polymerase, adenosine triphosphate (ATP), poly(A) polymerase reaction buffer (5×), and biotinylated poly(T)$_{30}$ were from Integrated DNA Technologies (Coralville, Iowa). Carbonic anhydrase (CA) from bovine erythrocytes, Zn(NO$_3$)$_2$, ZnCl$_2$, dipicolinic acid (DPA), trace metal grade 12 M HCl, trace metal grade NaOH, thioglycolic acid (TGA), and thioacetamide were from Sigma Aldrich (St. Louis, Mo.). NaCl, NaH$_2$PO$_4$, Na$_2$HPO$_4$, N-(2-hydroxyethyl)piperazine-N'-2-ethanesulfonic acid (HEPES), 2-amino-2-hydroxymethyl-propane-1,3-diol (Tris), 2-(N-morpholino)ethanesulfonic acid (MES), glacial acetic acid, ethanol, NeutrAvidin, streptavidin conjugated DyLight 488, dimethyl sulfoxide (DMSO), fluorescein-di-β-D-galactopyranoside (FDG), and fluorescein diacetate (FDA) were from Fisher Scientific (Pittsburgh, Pa.). Streptavidin conjugated beta-galactosidase was from Invitrogen (Carlsbad, Calif.). Carboxyl terminated magnetic beads with 4.5 µm diameter were from Spherotech (Lake Forest, Ill.). All chemicals or reagents were purchased to use without any further purification. The detailed description of the reagents and procedures used to prepare apo-CA and ZnS nanoparticles (50 nm in diameter) has been presented previously. For miRNA assays, the washing and hybridization buffer consisted of 0.1 M NaCl and 0.01 M phosphate buffer with pH 7.4. PBS was made of 137 mM NaCl, 1.4 mM $NaH_2PO_4$ and 8 mM $Na_2HPO_4$ with pH 7.4. To prepare HEPES pH 2 and HEPES pH 8, 12 M HCl or Tris base were dropwise added to HEPES solutions (25 mM HEPES and 50 mM NaCl with pH 7.4). MES buffer was made of 0.1 M MES and 0.5 M NaCl in DI water with pH 6.0. PBS-D buffer was comprised of 44 mM $NaH_2PO_4$, 56 mM $Na_2HPO_4$, 100 mM NaCl, 5 mM $MgCl_2.6H_2O$ and 3 mM $NaN_3$ in DI water with pH 7.4. 2 mM FDG solutions were prepared before use by diluting 394 µL of 1 mg/mL FDG (dissolved in a 50:50 mixture of ethanol and DMSO) into 2.606 mL of PBS-D buffer.

5 mg carboxyl terminated magnetic beads were mixed with 4 mg NHS and 5 mg EDC in 1 mL of MES buffer for 30 min. The magnetic beads were then washed and incubated with 80 nmol LNA in PBS for 2 hours. After the incubation, the beads were washed and re-suspended in 5 mL of PBS as stock and stored at 4° C.

The bioassay procedures for miRNA-21 were performed as follows. First, 1.5 µL of paramagnetic beads covalently conjugated with LNA were added to a microplate and washed twice. Serial dilutions of miRNA-21 were prepared in wash/hybridization buffer and incubated with the paramagnetic beads for 1 hour at 37° C. followed by 3 washes. Second, the polyadenylation solution was prepared using 0.2 mM ATP, 120 units/well poly(A) polymerase, and 1× reaction solution in DI water. After adding the prepared polyadenylation solution to the wells, the reaction was allowed to proceed for 40 minutes at 37° C. followed by washing the wells to remove all unreacted reagents and to quench the reaction. Third, 25 nM $T_{30}$-Biotin was added to the wells to hybridize with the poly(A) tails for 30 minutes at 37° C. Afterwards, the wells were washed 3 times and 5% bovine serum albumin prepared in HEPES pH 7.4 was added to the wells for 30 minutes to block the wells, beads, and bound oligonucleotides. Fourth, Neutravidin conjugated ZnS nanoparticles were diluted 250 times to a concentration of around 4 pM and added to each well to label the bound biotinylated thymine for 5 minutes. Nanoparticles that do not specifically bind to the biotinylated thymine are washed out using 4 washes with HEPES pH 7.4. Fifth, zinc ions are released from the bound ZnS nanoparticle labels through the addition of 50 µL HEPES pH 2 followed by adjusting the pH in all of the wells to a more neutral level by adding 100 µL of HEPES pH 8. Sixth, 25 µL of 4 µM apo-CA were added to the wells for zinc activation. Finally, 25 µL of 20 µM FDA were added for conversion to fluorescein by the activated enzymes. The enzymatic reaction was allowed to proceed for 15 minutes and the fluorescence in the wells was quantified with a Perkin Elmer (Waltham, Mass.) Victor 3 microplate reader using a bandpass excitation filter centered at 485 nm (bandwidth=14 nm) and a bandpass emission filter at 520 nm (bandwidth=25 nm).

For the miRNA assay using beta-galactosidase for signal transduction, the first three steps are same as the assay using ZnS nanoparticle labels. The fourth step is 50 µL of 10 µg/mL streptavidin-beta-galactosidase are added to each well and incubated for 5 minutes and the wells are washed three times. Then, the beads are suspended in 20 µL of PBS-D. The fifth step is 50 µL of 0.1 mM FDG prepared in PBS-D is added to each well and the reaction is allowed to proceed for 15 minutes prior to fluorescence quantification in the microplate reader (the filters are set with ex/em=485/520 nm).

All studies were performed in triplicate. The average and the standard deviation of triplicate signals were calculated for data analysis.

ZnS Nanoparticles are Sensitive Labels

Figure 28:
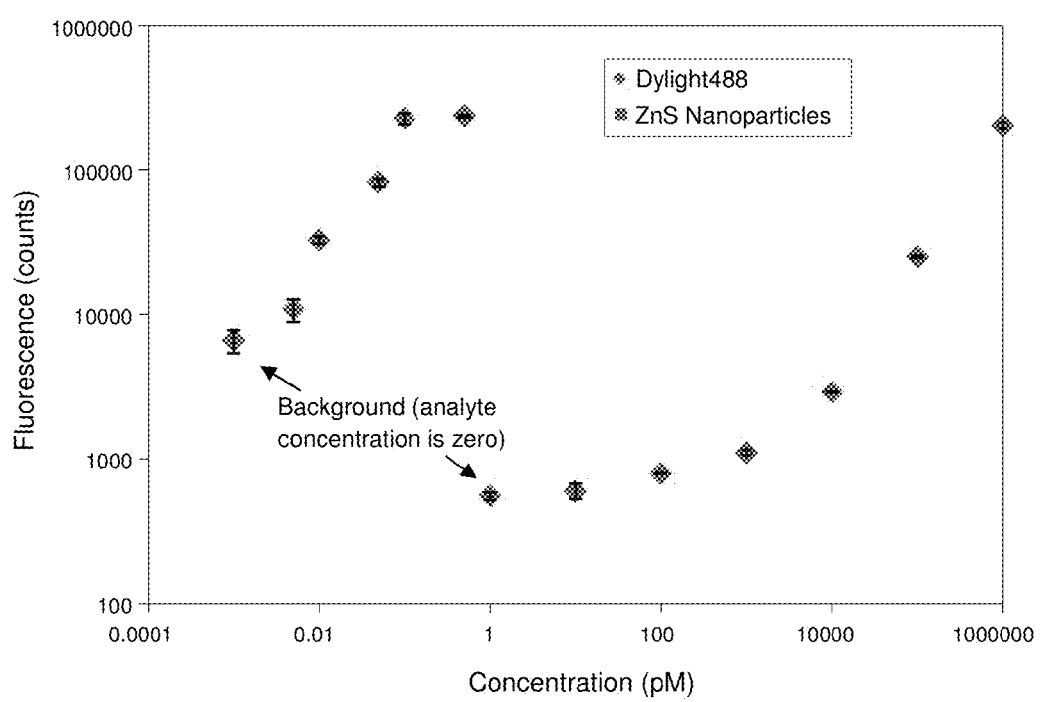
FIG. 28 shows fluorescence responses to: (1) ZnS nanoparticle concentrations using ion release and enzyme activation for signal transduction, and (2) Dylight488 concentrations.

To demonstrate that ZnS nanoparticles are sensitive labels, ZnS nanoparticles were serially diluted in HEPES pH 2, and 50 µL of each diluted solution were added to the wells followed by pH adjustment with 100 µL of HEPES pH 8. After adjusting the pH, 25 µL of apo-CA and 25 µL of 20 µM FDA were added to the wells for 15 min incubation before fluorescence measurement. In this study, ZnS nanoparticle concentrations ranging from 0-500 fM were tested. The fluorescence responses for different concentrations of ZnS nanoparticles are shown in FIG. 28. This figure demonstrates that the ZnS nanoparticle concentration as low as 5 fM can be detected using the developed enzyme-substrate system. As a comparison, Dylight488 (its excitation wavelength and emission peak wavelength are same as fluorescein) was diluted in HEPES buffer with pH 7.4 and measured under the same microplate setting. The fluorescence responses of Dylight488 are also presented in FIG. 28. It was found that the detection limit of Dylight488 was around 10 pM much higher than that of ZnS nanoparticles. A reason for the microplate reader to detect a lower concentration of ZnS nanoparticles is that ZnS nanoparticles can release high amount of zinc ions to trigger enzyme for the generation of fluorescein.

Figure 29:
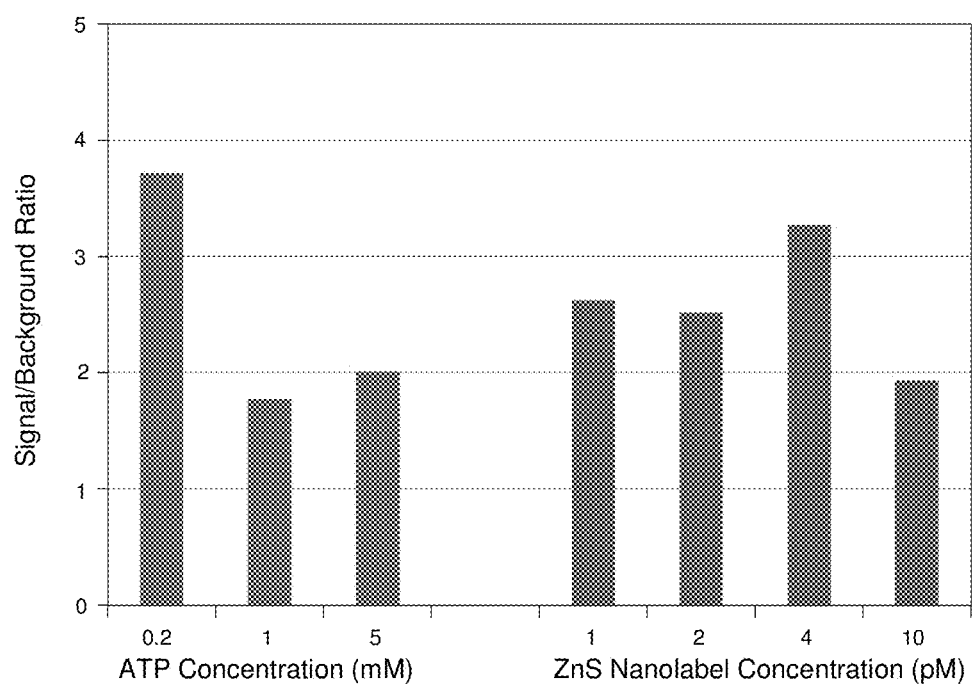
FIG. 29 shows the optimization of ATP and ZnS nanolabel concentration through comparison of fluorescence responses for 50 and 0 pM miRNA-21 to determine signal to background ratio.

In the miRNA assay, 120 U/well of poly(A) polymerase was used in order to lower the overall assay cost. Since polyadenylation only occurs on the 3' end of the captured miRNA, excessive ATP molecules in wells may block the diffusion of poly(A) polymersase to the 3' end of the captured miRNA and thus lower the efficiency of polyadenylation. Thus, it was desirable to investigate the optimized ATP concentration for polyadenylation to achieve a good assay signal/background ratio. To do so, 50 pM miRNA-21 and 0 pM (for background signal) were used to quantify the signal to background ratios under 0.2, 1, and 5 mM concentrations of ATP. As shown in FIG. 29, 0.2 mM ATP resulted in the highest signal to background ratio, and thus it was used in the assay.

The concentration of ZnS nanoparticle labels was optimized because too many or too few ZnS nanoparticle labels could cause high background or insufficient labeling. Similar to the optimization procedure of ATP, 50 pM miRNA-21 and 0 pM (for background signal) were used to determine the signal to background ratios under 1, 2, 4 and 10 pM concentrations of ZnS nanoparticle labels. The signal to background ratio for each concentration of ZnS nanoparticle labels is also demonstrated in FIG. 29. The concentration of ZnS nanoparticle labels at 4 pM was determined as the miRNA assay labeling condition. This higher signal to background ratio arose from a balance of enhanced signal and relatively low non-specific binding background compared with the other ZnS labeling concentrations.

Figure 30:
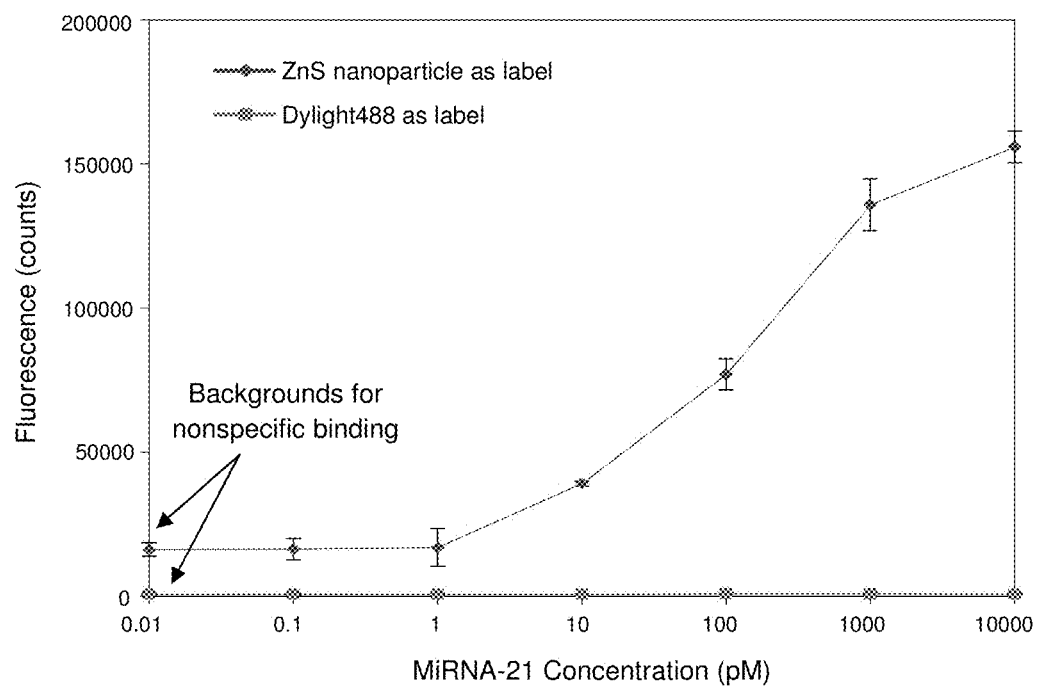
FIG. 30 is a calibration curve for miRNA-21 detection using NeutrAvidin conjugated ZnS nanoparticles with ion release and enzyme activation for signal transduction (Calibration using streptavidin conjugated Dylight 488 labels is used as a control).

Adopting the aforementioned optimized bioassay conditions, the assay on miRNA-21 using ZnS nanolabels was performed. MiRNA-21 was serially diluted in wash/hybridization buffer at concentrations ranging from 0-10 nM and incubated with paramagnetic beads immobilized with the LNA probe complimentary to miRNA-21. The calibration curve for miRNA-21 concentration versus fluorescence is demonstrated in FIG. 30. As a comparison, a conventional fluorescence assay on miRNA-21 using Dylight488 labeling was performed. The fluorescence assay adopted the same protocol as the ZnS nanoparticle based assay, but in the last assay step streptavidin conjugated Dylight488 (1 µM) was applied for signal transduction. The calibration curve of the fluorescence assay is also included in FIG. 30. Through comparing the two curves, it can be seen that ZnS nanoparticle labeling was more effective in quantifying miRNA-21 concentrations than the conventional organic fluorophore. For the ZnS nanoparticle based miRNA assay, miRNA-21 levels up to 10 nM can be quantified before the calibration curve reaches saturation and the detection limit is estimated to be around 3 pM (150 amol or 1 pg miRNA-21 considering 50 µL of reaction or hybridization volume) on the basis of three times of the blank sample standard deviation.

Figure 31:
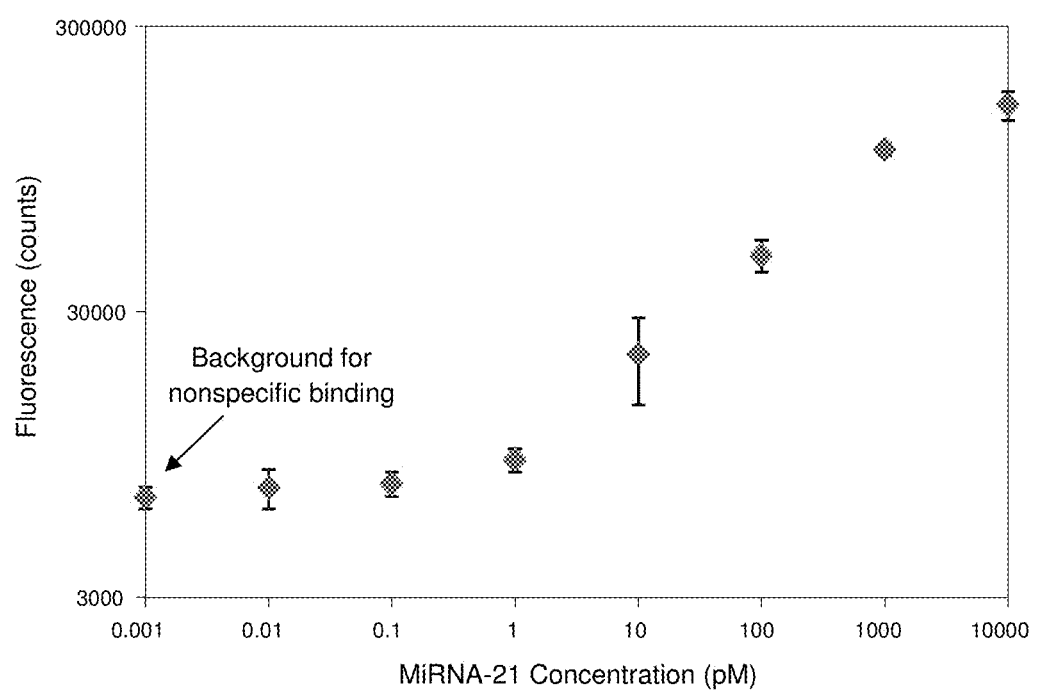
FIG. 31 is a calibration curve for miRNA-21 detection using beta-galactosidase for signal transduction.

Adopting the same optimized ATP concentration as that in the assay using ZnS nanoparticle labels, the assay on miRNA-21 using beta-galactosidase was performed. The calibration curve is shown in FIG. 31. It can be seen that the detection limit was estimated to be around 2 pM (100 amol or 0.67 pg miRNA-21 considering 50 µL of reaction or hybridization volume).

These detection limits are comparable to those of recently reported miRNA assays. In some further examples, of the disclosed assay additional blocking steps are performed to minimize background noise, such as that caused by the nonspecific binding of ZnS nanoparticle labels by interacting with molecules (e.g., poly(A) tails, LNAs) on bead surface.

In this example, a miRNA detection approach in a microplate assay format using magnetic separation, polyadenylation and signal amplification is presented. The assay is of a detection range with at least three-order magnitude and a detection limit at picaomolar level (or picogram miRNA). The disclosed miRNA assay is an efficient way for detecting miRNA by coupling with miRNA extraction/pre-concentration devices which collect miRNA from cells, tissues or body fluids. Moreover, it is contemplated that magnetic beads could be used in this assay to have an analyte enrichment function due to their flowing capture surface and magnetic separation function. It is believed that the same amount of beads can be spiked into a relative larger sample volume to achieve a lower detection limit. Magnetic microbeads coupled with microplates can also have a potential for multiplexing or high throughput sample analysis. The developed method is believed to be able to be applied for miRNA detection in a number of different environments, including clinical environments.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method of detecting an analyte in a sample, comprising:
    contacting the sample containing the analyte with a detecting agent, wherein the detecting agent comprises a specific binding agent that binds the analyte and zinc nanoparticles wherein the zinc nanoparticles and specific binding agent are coupled together, spherical and have an average diameter of 50 nm;
    exposing the analyte bound to the specific binding agent which is coupled to the zinc nanoparticles to an acidic condition to release zinc ions from the zinc nanoparticles;
    contacting the released zinc ions with an indicator to generate a signal; and detecting the signal.

2. The method of claim 1, further comprising contacting the released zinc ions with a basic solution to adjust the pH in the range of 5.5 to 7.0 prior to contacting the released zinc ions with an indicator to generate a signal.

3. The method of claim 1, wherein the zinc nanoparticles are zinc sulfide nanoparticles or zinc oxide nanoparticles.

4. The method of claim 1, wherein the zinc nanoparticles are zinc sulfide nanoparticles.

5. The method of claim 1, wherein the zinc nanoparticles are conjugated to one of avidin, streptavidin, or neutravidin.

6. The method of claim 5, wherein the zinc nanoparticles are conjugated to neutravidin.

7. The method of claim 6, wherein the zinc nanoparticles are zinc sulfide nanoparticles.

8. The method of claim 7, wherein the signal is a fluorescent signal.

9. The method of claim 8, further comprising capturing the analyte from the sample prior to contacting the analyte with a detecting agent by contacting the sample containing the analyte with a capture molecule specific for the analyte.

10. The method claim 9, wherein the capture molecule is conjugated to a substrate.

11. The method of claim 10, wherein the specific binding agent is a detection antibody capable of binding to the analyte.

12. The method of claim 11, wherein the detection antibody is tagged with biotin.

13. The method of claim 12, wherein contacting the released metal ions with an indicator to generate a signal comprises contacting the release metal ions with an apo-enzyme and a substrate to generate the signal.

14. The method of claim 13, wherein the apo-enzyme is apo-carbonic anhydrase and the substrate is fluorescein diacetate (FDA).

\* \* \* \* \*

SEQUENCE LISTING

```
<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
uagcuuauca gacugauguu ga                                              22

<210> SEQ ID NO 2
<211> LENGTH: 17
<212> TYPE: DNA
<213> ORGANISM: Artificial Sequence
<220> FEATURE:
<223> OTHER INFORMATION: nucleic acid synthetic probe complimentary to
      miRNA-21

<400> SEQUENCE: 2
tcaacatcag tctgata                                                    17
```